United States Patent [19]

Munroe

[11] Patent Number: 4,791,106

[45] Date of Patent: Dec. 13, 1988

[54] 1-CARBACEPHALOSPORIN ANTIBIOTICS

[75] Inventor: John E. Munroe, Indianapolis, Ind.

[73] Assignee: Eli Lilly and Company, Indianapolis, Ind.

[21] Appl. No.: 66,908

[22] Filed: Jun. 26, 1987

Related U.S. Application Data

[63] Continuation-in-part of Ser. No. 814,943, Dec. 30, 1985, abandoned.

[51] Int. Cl.$^4$ .................. A61K 31/435; C07D 471/04
[52] U.S. Cl. ..................................... 514/210; 540/205
[58] Field of Search ....................... 540/205; 514/210; 546/183

[56] References Cited

U.S. PATENT DOCUMENTS

| | | | |
|---|---|---|---|
| 4,174,136 | 11/1979 | Christensen et al. | 540/205 |
| 4,226,866 | 10/1980 | Christensen et al. | 514/229 |

FOREIGN PATENT DOCUMENTS

| | | | |
|---|---|---|---|
| EPO 0112481 | 7/1984 | European Pat. Off. | |
| 232623 | 8/1987 | European Pat. Off. | 540/205 |

OTHER PUBLICATIONS

Uyeo, S., et al., "Synthesis of 1-Carbacephem Derivatives", *Chem. Pharm. Bull.*, 28, 1563–1577 (1980).
Hatanaka, M., et al., *Tetrahedron Letters*, vol. 24, No. 44, pp. 4837–4838 (1983).
Hirata, T., et al., *Chem. Abst.*, 93:239247t.
EPO Search Report in applicant's EPO application corresponding to applicant's parent application Ser. No. 814,943, filed Dec. 30, 1985.

*Primary Examiner*—Donald G. Daus
*Assistant Examiner*—Cecilia Shen
*Attorney, Agent, or Firm*—William B. Scanlon; Leroy Whitaker

[57] ABSTRACT

7β-Acylamino-3-alkoxycarbonyl-(and 3-keto)-1-carba(1-dethia)-3-cephem-4-carboxylic acids and derivatives and related 3-substituted compounds are provided as antibiotics useful for treating infections in man and animals. Pharmaceutical formulations comprising the antibiotics and intermediates a process for their preparation are provided. Exemplary compounds provided are 7β-[D-(2-phenyl-2-aminoacetyl)amino]-3-methoxycarbonyl-1-carba(1-dethia)-3-cephem-4-carboxylic acid and 7β-[2-(2-aminothiazol-4-yl)-2-methoxyiminoacetamido]-3-acetyl-1-carba(1-dethia)-3-cephem-4-carboxylic acid.

56 Claims, No Drawings

1-CARBACEPHALOSPORIN ANTIBIOTICS

CROSS-REFERENCE TO RELATED APPLICATION

This application is a continuation-in part of application Ser. No. 814,943, filed Dec. 30, 1985, now abandoned.

This invention relates to 1-carba(dethia)cephalosporin antibiotics, a process and intermediates for the preparation thereof, to pharmaceutical formulations comprising the antibiotics, and to a method for the treatment of infectious diseases in man and other animals.

The 1-carba(dethia)cephalosporin antibiotics have the bicyclic ring system represented by the following formula wherein the numbering system is that commonly employed in the arbitrary cepham nomenclature system.

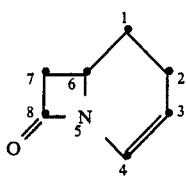

The 1-carba(1-dethia)cephalosporins are referred to herein for convenience as 1-carbacephalosporins or as 1-carba-3-cephem-4-carboxylic acids or numbered derivatives thereof.

The preparation of 1-carbacephalosporins and C-3 substituted methyl derivatives thereof is taught broadly by Christensen et al., in U.S. Pat. No. 4,226,866. Hirata et al., in U.K. patent application No. 2041923, teach a method for preparing 3-H and 3-halo 1-carbacephalosporins, while Hatanaka et al., *Tetrahedron Letters*, 24, No. 44, pp. 4837–4838 (1983) teach a method for preparing a 3-hydroxy-($\pm$)-1-carbacephalosporin.

Although many safe and potent antibiotics of the $\beta$-lactam class are known and used clinically, the research into this class continues in efforts to find antibiotics with improved efficacy, particularly against microorganisms insensitive or resistant to the known antibiotics.

7$\beta$-Acylamino-1-carba-3-cephem-4-carboxylic acids substituted in the 3-position by a carboxy group, a carboxy derivative, a keto group or a substituted keto derivative, and esters and salts thereof are broad spectrum antimicrobial compounds. The invention comprises formulations of the 1-carbacephalosporins useful in a therapeutic method for the treatment of infectious diseases of man and other animals caused by gram-positive and gram-negative bacteria.

The invention also provides a process for preparing the 1-carbacephalosporins which comprises the cycloaddition of a 3$\beta$-protected amino-4$\beta$-(2-haloethyl)-azetidin-2-one with a phenylsulfinyl-substituted or phenylsulfonyl-substituted acrylic acid ester in the presence of a strong non-nucleophilic base. Deprotection of the 7$\beta$-protected amino group of the product, reacylation of the amino group with a carboxylic acid, and deesterification of the C-4 carboxy ester provides a 1-carba-3-cephem-4-carboxylic acid antibiotic having the desired stereochemistry of the semi-synthetic cephalosporin antibiotics.

The 1-carbacephalosporins provided by this invention are represented by Formula (1):

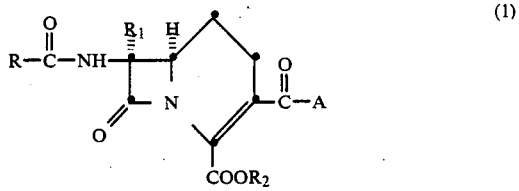

wherein R is the residue of a carboxylic acid R—COOH having from 1 to 20 carbon atoms, wherein R is hydrogen, alkyl, aryl, aralkyl, heteroaryl, heteroaralkyl, and such groups substituted by alkyl, alkoxy, amino, mono- or dialkylamino, alkanoylamino, alkanoyl, hydroxy, acyloxy, carboxy, cyano, halogen, alkylsulfonyloxy, alkylsulfonylamino, arylsulfonyloxy, or arylsulfonylamino. Preferably, RC(O) is the acyl moiety of a 7-acylamino group of the known cephalosporin antibiotics or the 6-acylamino group of the known penicillin antibiotics;

$R_1$ is hydrogen, $C_1$–$C_4$ alkoxy, $C_1$–$C_4$ alkylthio or the formamido group, —NHCHO;

$R_2$ is hydrogen, a carboxy-protecting group, or a biologically-labile ester group;

A is hydroxy, halo, azido, 2-(tri-$C_1$–$C_4$ alkylsilyl)ethoxy, $C_1$–$C_6$ alkoxy, $C_2$–$C_6$ alkenyloxy, $C_2$–$C_6$ alkynyloxy, $C_1$–$C_4$ alkoxycarbonyloxy, phenoxy, or substituted phenoxy;

or A is $C_1$–$C_6$ alkoxy substituted by one or two of the same or different groups selected from among hydroxy, amino, $C_1$–$C_4$ alkylamino, di-($C_1$–$C_4$ alkyl)amino, $C_1$–$C_4$ alkanoylamino, halo, $C_1$–$C_4$ alkoxy, $C_1$–$C_4$ alkylthio, cyano, carboxy, $C_1$–$C_4$ alkoxycarbonyl, carbamoyl, carbamoyloxy, N-($C_1$–$C_4$ alkyl)carbamoyloxy, N,N-di-($C_1$–$C_4$ alkyl)carbamoyloxy, $C_1$–$C_4$ alkoxycarbonyloxy, phenoxycarbonyloxy, $C_1$–$C_4$ alkoxycarbonylamino, phenoxycarbonylamino, N-($C_1$–$C_4$ alkyl)carbamoylamino, N,N-di-($C_1$–$C_4$ alkyl)carbamoylamino, N-phenylcarbamoylamino, anilino, substituted anilino, phenyl, substituted phenyl, or a heterocyclic amino group $R_3$NH— wherein $R_3$ is thienyl, furyl or a 5-membered nitrogen containing heterocyclic ring represented by the formulae

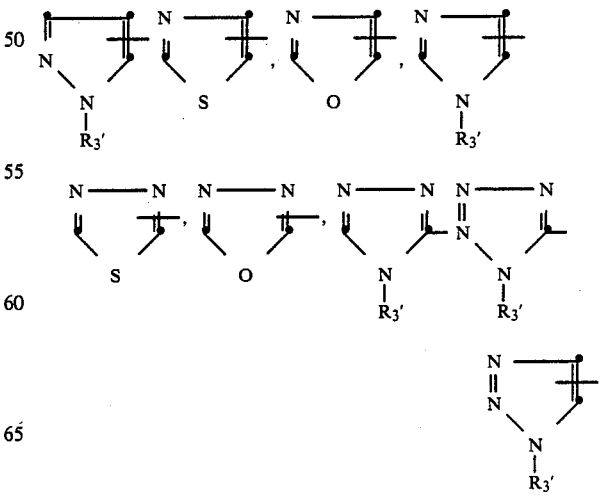

wherein $R_3'$ is hydrogen, $C_1$-$C_4$ alkyl or $C_1$-$C_4$ alkyl substituted by carboxy, sulfo, or di($C_1$-$C_4$ alkyl)amino; or $R_3$ is a 6-membered nitrogen-containing ring represented by the formulae

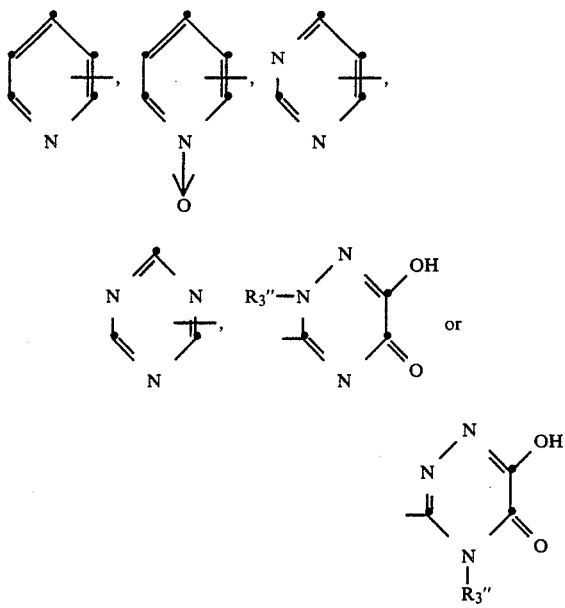

wherein $R_3''$ is hydrogen or $C_1$-$C_4$ alkyl; or a heterocyclic thio group $R_3{}^oS$— wherein $R_3{}^o$ is phenyl, substituted phenyl or $R_3$ as defined above; or a quaternary heterocyclic group $R_4{}^o{}^\oplus X^\ominus$ wherein $R_4{}^o{}^\oplus$ is a nitrogen containing heterocyclic represented by the formulae

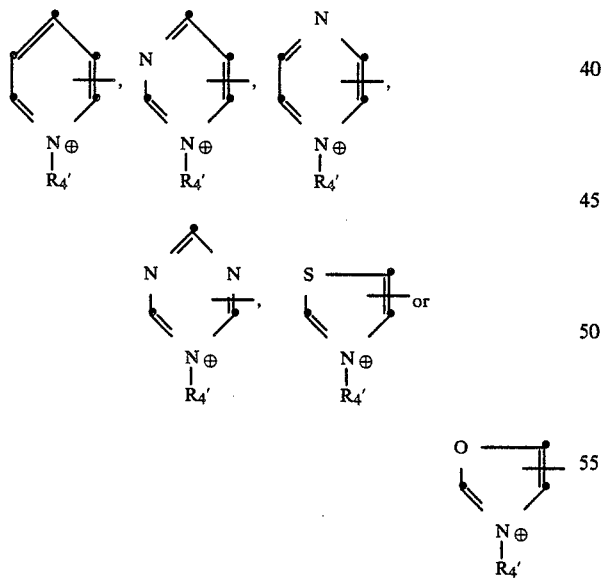

wherein $R_4'$ is $C_1$-$C_4$ alkyl, benzyl, or 13 $CH_2COOH_3$, and $X^\ominus$ is a halide, sulfate, or nitrate anion; or $R_4{}^o{}^\oplus$—S—$X^\ominus$ wherein $R_4{}^o{}^\oplus$ and $X^\ominus$ are as defined above; or $C_1$-$C_6$ alkoxy substituted by a heterocyclic group $R_3$ as defined above;
or A is an amino group represented by the formula

—N(R')(R'')

wherein R' and R'' are independently hydrogen, phenyl, substituted phenyl, $C_1$-$C_4$ alkyl, $C_1$-$C_4$ alkyl substituted by one or two of the same or different groups selected from among halo, hydroxy, $C_1$-$C_4$ alkanoyloxy, $C_1$-$C_4$ alkylsulfonyloxy, phenyl, substituted phenyl, amino, or $C_1$-$C_4$ alkanoylamino; or R' and R'' can be taken together with the nitrogen atom to which they are bonded to form a 5-7 membered ring represented by the formula

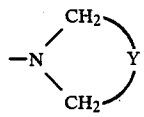

wherein Y is —$CH_2$—$_p$ or —$CH_2$—Y'—$CH_2$— wherein p is 2-4 and Y' is O, S, or NR''' wherein R''' is hydrogen or $C_1$-$C_4$ alkyl; or R' is hydrogen and R'' is $C_1$-$C_4$ alkyl substituted by a heterocyclic $R_3$, or a heterocyclic amino group $R_3NH$—, or a heterocyclic thio group $R_3S$—, or a quaternary heterocyclic group $R_4{}^o{}^\oplus X^\ominus$, wherein $R_3$, $R_4{}^o{}^\oplus$ and $X^\ominus$ have the same meaningss as defined above;

or A is heterocyclic amino group $R_3NH$— wherein $R_3$ is as defined above, phenyl, or substituted phenyl;

or A is $C_1$-$C_4$ alkyl, or $C_1$-$C_4$ alkyl substituted by hydroxy, $C_1$-$C_4$ alkanoyloxy, $C_1$-$C_4$ alkoxy, $C_1$-$C_4$ alkylthio, halogen, carboxy, cyano, amino, $C_1$-$C_4$ alkylamino, di-($C_1$-$C_4$ alkyl)amino, $C_1$-$C_4$ alkanoylamino, $C_1$-$C_4$ alkylsulfonylamino, $C_1$-$C_4$ alkylsulfonyloxy, phenyl, substituted phenyl, phenylthio, substituted phenylthio, and phenoxy, substituted phenoxy, anilino, substituted anilino, a heterocyclic group $R_3$, a heterocyclic amino group $R_3NH$, a heterocyclic thio group $R_3S$—, or a quaternary heterocyclic group $R_4{}^o{}^\oplus X^\ominus$ or $R_4{}^o{}^\oplus$—S—$X^\ominus$, wherein $R_3$, $R_4{}^o{}^\oplus$, and $X^\ominus$ are as defined above;

or A is phenyl, thienyl, furyl, pyridyl, pyrimidyl, imidazolyl, pyrazolyl, tetrazolyl, oxazolyl, thiazolyl, thiadiazolyl or oxadiazolyl, and said phenyl or heterocycle substituted by one or two of the same or different substituents selected from $C_1$-$C_4$ alkyl, $C_1$-$C_4$ alkoxy, halogen, amino, or hydroxy;

or A is a carboxy group or a derivative of a carboxy group represented by the formula —$COR_6$ wherein $R_6$ is hydrogen, hydroxy, $C_1$-$C_4$ alkoxy, phenoxy, substituted phenoxy, tri-($C_1$-$C_4$ alkyl)silyloxy, amino, $C_1$-$C_4$ alkylamino, di-($C_1$-$C_4$ alkyl)amino, phenyl, substituted phenyl, or $C_1$-$C_4$ alkyl;

or A is the group —$CH_2$—$^\oplus R_4$ wherein $^\oplus R_4$ is pyridinium, or a substituted pyridinium group substituted by one or two of the same or different groups selected from among $C_1$-$C_4$ alkyl, $C_1$-$C_4$ alkoxy, $C_1$-$C_4$ alkylthio, hydroxy, halogen trifluromethyl, cyano, carboxy, carbamoyl, amino, or $C_1$-$C_4$ alkoxycarbonyl; or the pyridinium ring is substituted on adjacent carbon atoms with a divalent alkylene group represented by the formula —$CH_2$—$_{p'}$ wherein p' is 3-5, or the divalent alkylene group is interrupted by an O, S, or one or two N atoms and in addition can contain one or two double bonds and can be substituted in either ring by one or two of the same or different substituents selected from the groups defined above when $^\oplus R_4$ is a substituted pyridine; or $^\oplus R_4$ is a thiazolium ring or a substituted thiazolium ring substituted by one or two of the same or different groups, amino, $C_1$–$C_4$ alkyl, $C_1$–$C_4$ alkylthio, $C_1$–$C_4$ alkoxy, $C_1$–$C_4$ alkyl substituted by hydroxy, $C_1$–$C_4$ alkanoyloxy, $C_1$–$C_4$ alkylsulfonyloxy, halogen, $C_1$–$C_4$ alkoxy, $C_1$–$C_4$ alkylthio, or amino, or the thiazolium ring is substituted on the adjacent carbon atoms with a divalent alkylene group represented by the formula —$CH_2$—$_{p'}$ wherein p' is 3–5; and when $R_2$ is hydrogen, the pharmaceutically acceptable non-toxic salts and biologically labile esters thereof.

The 1-carbacephalosporins represented by the above Formula (1), wherein $R_2$ is hydrogen or a biologically labile ester and the pharmaceutically acceptable salts thereof, inhibit the growth of microorganisms pathogenic to man and animals and may be used to control infectious diseases. The compounds of the invention are obtained in the process provided herein in the same stereochemical form as that of the semi-synthetic cephalosporin antibiotics.

The terms used to define the 1-carbacephalosporins represented by Formula (1) have the commonly accepted meanings as exemplified below. As used hereinabove in Formula (1), the term $C_1$–$C_4$ alkoxy refers to the lower straight and branch chain alkoxy groups such as methoxy, ethoxy, n-propoxy, isopropoxy, n-butoxy, t-butoxy, and the like; $C_1$–$C_4$ alkylthio refers to the corresponding lower alkylthio groups such as methylthio, ethylthio, n-propylthio, isopropylthio, t-butylthio, and the like; halo or halogen refer to fluoro, chloro, bromo, or iodo, preferably chloro or bromo; $C_1$–$C_6$ alkoxy refers to the straight and branched chain alkoxy groups including $C_1$–$C_4$ alkoxy as exemplified above and n-pentyloxy, n-hexyloxy, 3-methylbutyloxy, 3-methylpentyloxy, 2-ethylpropoxy, 2,2-dimethylbutoxy, 2,3-dimethylbutoxy, neopentyloxy, and the like; $C_2$–$C_6$ alkenyloxy refers to vinyloxy, allyloxy, 1-methylallyloxy, 2-butenyloxy, 3-hexenyloxy, and the like; $C_2$–$C_6$ alkynyloxy refers to alkynyloxy, 2-propynyloxy, 2-butynyloxy, 3-butynyloxy, 3-pentynyloxy, 4-pentynyloxy, 2-hexynyloxy, 5-hexynyloxy, 2-methyl-4-pentynyloxy, 1,1-dimethyl-2-propynyloxy, 1,1-dimethyl-3-butynyloxy, and the like.

Substituted $C_1$–$C_6$ alkoxy groups represented by A are exemplified by 2-hydroxyethoxy, 3-hydroxypropoxy, 3,4-dihydroxybutoxy, 2-aminoethoxy, 2-(dimethylamino)ethoxy, 4-aminopentoxy, 3-aminobutoxy, 4-(acetylamino)butoxy, 2-hydroxy-3-aminobutoxy, 3-chloropropoxy, 2-bromoethoxy, bromomethoxy, 5-chlorohexyloxy, 2-chloro-4-chlorobutoxy, 2-amino-4-fluorobutoxy, 2-fluoroethoxy, iodomethoxy, 3-hydroxy-5-fluorohexyloxy, 2-cyanoethoxy, 3-cyanopropoxy, 2-cyano-4-chlorobutyl, 3-cyano-5-aminopentoxy, 3-cyano-4-hydroxyhexyloxy, 2-methoxyethoxy, 2-ethoxybutoxy, 2,3-dimethoxybutoxy, 3-hydroxy-4-methoxypentoxy, 3-cyano-4-ethoxypentoxy, 3-amino-4-methoxybutoxy, 3-methoxy-5-aminopentoxy, 4-methylthiobutoxy, 3-ethylthiopropoxy, 3-cyano-5-methylthiohexyloxy, 2-amino-4-methylthiobutoxy, 4-carboxybutoxy, 3-amino-4-carboxybutoxy, carboxymethoxy, 2-carboxyethoxy, 2-amino-3-carboxypropoxy, 2-chloro-4-carboxypentoxy, 2-carboxy-4-fluorobutoxy, 6-carboxyhexyloxy 2-(methoxycarbonyl)ethoxy, 3-(ethoxycarbonyl)propoxy, 3-methoxy-5-(methoxycarbonyl)pentoxy, carbamoylmethoxy, 2-carbamoylethoxy, 5-carbamoylpentoxy, carbamoyloxymethoxy, 1-(carbamoyloxy)ethoxy, 2-(carbamoyloxy)ethoxy, 6-(carbamoyloxy)hexyloxy, N-methylcarbamoyloxymethoxy, N,N-dimethylcarbamoyloxymethoxy, 2-(ethoxycarbonyloxy)ethoxy, 4-(t-butyloxycarbonyloxy)butoxy, 2-(phenoxycarbonyloxy)ethoxy, p-chlorophenoxycarbonyloxyethoxy, 3-(methoxycarbonylamino)propoxy, 4-(ethoxycarbonylamino)pentoxy, 2-(phenoxycarbonylamino)ethoxy, 3-(N,N-dimethylcarbamoylamino)propoxy, 2-(N-phenylcarbamoylamino)ethoxy, benzyloxy, 3-aminobenzyloxy, 3,4-dichlorobenzyloxy, 4-methoxybenzyloxy, 4-methylbenzyloxy, 2-phenylethoxy, 2-phenylpropoxy, 4-phenylbutoxy, 2-(4-aminophenyl)ethoxy, 4-(4-fluorophenyl)butoxy, 2-thienylmethoxy, 2-(3-thienyl)ethoxy, 2-(2-furyl)ethoxy, and 4-(2-furyl)butoxy; examples of $C_1$–$C_6$ alkoxy substituted by a heterocyclic amino group $R_3NH$— are 2-(2-thienyl)aminoethoxy, 3-(2-furyl)aminopropoxy, 2-(anilino)ethoxy, 5-(anilino)hexyloxy, 3-(4-chloroanilino)butoxy, 2-[(thiazol-4-yl)amino]ethoxy, 3-[(N-methylpyrazol-5-yl)amino]propoxy, 2-[(1,3,4-thiadiazol-2-yl)amino]ethoxy, 3-[(1-carboxymethyl-1,3,4-triazol-2-yl)amino]propoxy, 2-[(pyridin-4-yl)amino]ethoxy, 2-[(pyrimidin-2-yl)amino]propoxy, and like anilino and heterocyclic amino substituted alkoxy groups; examples of $R_3{}^oS$-substituted $C_1$–$C_6$ alkoxy groups are phenylthiomethoxy, 2-phenylthioethoxy, 2-(4-chlorophenylthio)propoxy, (2-aminothiazol-4-ylthio)methoxy, 5-(pyridin-3-ylthio)pentoxy, 2-(1H-tetrazol-5-ylthio)ethoxy, 3-(pyrimidin-2-ylthio)propoxy, and the like; examples of $C_1$–$C_6$ alkoxy substituted by a quaternary heterocyclic group, $R_4{}^o{\oplus}X^{\ominus}$ are 2-(1-methylpyridinium-2-yl)ethoxy, 2-(1-methylpyridinium-2-yl)ethoxy, 2-(1-acetylmethylpyridinium-2-yl)ethoxy, 3-(1-methylpyrimidinium-4-yl)propoxy, 4-(1-ethylpyrazinium-2-yl)butoxy, 2-(3-methylthiazolium-4-yl)ethoxy, and like quaternary heterocyclic substituted $C_1$–$C_6$ alkoxy groups; and examples of $C_1$–$C_6$ alkoxy groups substituted by $R_3$ heterocyclics are, 2-thienylmethoxy, 3-thienylmethoxy, 2-(1,3,4-thiadiazol-2-yl)ethoxy, 2-(1H-tetrazol-5-yl)ethoxy, 3-(pyridin-4-yl)propoxy, 2-(2-aminothiazol-4-yl)propoxy, 2-(1-carboxymethyl-1H-tetrazol-5-yl)ethoxy, (1-methyl-5-hydroxy-1,3,4-triazin-6-one-2-yl)methoxy, pyridin-3-ylmethoxy, and like heterocyclic alkoxy groups.

Illustrative of the amino group —N(R')(R'') defined for A are amino (R'=R''=H), methylamino, dimethylamino, ethylamino, methylethylamino, di-(n-butyl)amino, N-(3-chloropropyl)amino, N-(4-bromobutyl)amino, 2-hydroxyethylamine, di-(2-hydroxyethyl)amine, di-(3-hydroxypropyl)amine, methylsulfonylamino, n-butylsulfonylamino, N-(2-acetoxyethyl)amino, N-(4-propionoxybutyl)amino, and like mono or disubstituted groups.

When in Formula (1) A is an amino group —N(R')((R'') and R' is hydrogen and R'' is $C_1$–$C_4$ alkyl substituted by a heterocyclic $R_3$, examples of such groups are 2-(2-thienyl)ethylamino, 2-thienylmethylamino, 2-pyridylmethylamino, 2-(2-aminothiazol-4-yl)ethylamino, 4-(2-furyl)butylamino, 2-(1,3,4-thiadiazol-2-yl)ethylamino, 1-methylimidazol-2-ylmethylamino, and like heterocyclicalkylamino groups; and when R'' is $C_1$–$C_4$ alkyl substituted by a heterocyclic amino group $R_3NH$— examples are 2-(2-thienylamino)ethylamino, 3-(pyrazol-5-amino)propylamino, 2-(1,3,4-thiadiazol-2-ylamino)ethylamino, 4-(1,2,3-triazol-5-ylamino)butylamino, and 3-(1-methyl-1,3,4-triazol-2-amino)propylamino; and when R'' is $C_1$–$C_4$ alkyl substituted by a heterocyclic thio group $R_3S$— examples are, 2-(1-methyltetrazol-5-ylthio)ethylamino, 3-(5-methyl-1,3,4-thiadiazol-2-ylthio)propylamino, 4-(pyrimidin-2-ylthio)butylamino, and like heterocyclicthioalkylamino groups; and when R'' is $C_1$–$C_4$ alkyl substituted by a quaternary heterocyclic group $R_4{}^\oplus X^\ominus$ examples of such quaternary groups are 2-(1-methylpyridinium-4-yl)ethylamino, 2-(1-ethylpyridinium-3-yl)ethylamino, 3-(1-methylpyrazinium-2-yl)propylamino, 2-(3-methylthiazolium-4-yl)ethylamino, 3-(1-methylpyrimidinium-2-yl)propylamino, and like groups wherein A is the group —N(R')(R").

Examples of the amide-forming groups when R' and R" are taken together to form a 5–7 membered ring are pyrrolidino, piperidino, morpholino, thiomorpholino, piperazino, 4-methylpiperazino, and 4-ethylpiperazino.

When A in Formula (1) is alkyl or a substituted alkyl group, the compounds represented are 3-keto-1-carbacephalosporins. Examples of groups forming substituted 3-keto groups when A is substituted $C_1$–$C_4$ alkyl are 2-hydroxyethyl, 3-hydroxypropyl, 4-hydroxybutyl, 2-acetoxyethyl, acetoxymethyl, 2-methoxyethyl, 3-t-butyloxypropyl, ethoxymethyl, 2-ethoxyethyl, 4-methoxybutyl, bromomethyl, chloromethyl, 3-bromobutyl, 4-iodobutyl, 2-(methylthio)ethyl, 3-(n-butylthio)butyl, methylthiomethyl, isopropylthiomethyl, 2-carboxyethyl, 4-carboxybutyl, 3-cyanopropyl, 2-cyanoethyl, 2-aminoethyl, 3-aminobutyl, 2-(dimethylamino)ethyl, 4-(diethylamino)butyl, methylaminomethyl, 2-(n-butylamino)ethyl, 2-(methylsulfonylamino)ethyl, n-propylsulfonylaminomethyl, 3-(methylsulfonyloxy)propyl, benzyl, 2-phenylethyl, 4-hydroxybenzyl, 3,4-dimethoxybenzyl, 3,4-methylenedioxybenzyl, 4-chlorobenzyl, 2-phenoxyethyl, 3-phenoxypropyl, phenoxymethyl, 2-(4-chlorophenoxy)ethyl, 2-phenylthioethyl, phenylthiomethyl, anilinomethyl, 2-anilinoethyl, 4-anilinobutyl, 4-chloroanilinomethyl, 4-ethoxyanilinomethyl, and like substituted alkyl groups A. Further, examples of A, when A is $C_1$–$C_4$ alkyl substituted by —$SR_3$ are imidazol-5-thiomethyl, 1-methylimidazol-4-thiomethyl, thiazol-4-thiomethyl, thiazol-2-thiomethyl, oxazol-4-thiomethyl, oxazol-5-thiomethyl, pyrazol-5-thiomethyl, 1-ethylpyrazol-5-thiomethyl, 1,3,4-thiadiazol-5-thiomethyl, 1,3,4-oxadiazol-5-thiomethyl, 1,3,4-triazol-5-thiomethyl, 1-carboxymethyl-1,3,4-triazol-5-thiomethyl, 1H-tetrazol-5-thiomethyl, 1-(2-carboxyethyl)-1H-tetrazol-5-thiomethyl, 1-(2-dimethylaminoethyl)-1H-tetrazol-5-thiomethyl, 1-sulfomethyl-1H-tetrazol-5-thiomethyl, pyridyl-2-thiomethyl, pyridyl-4-thiomethyl, pyridyl-3-thiomethyl, pyridyl-4-thiomethyl N-oxide, pyridyl-4-thiomethyl N-oxide, pyrimidyl-2-thiomethyl, pyrimidyl-4-thiomethyl, 1,3,5-triazin-2-ylthiomethyl, 3-methyl-5-hydroxy-6-oxo-1,3,4-triazin-2-thiomethyl, 1-methyl-5-hydroxy-6-oxo-1,3,4-triazin-2-ylthiomethyl, 2-(pyridyl-4-thio)ethyl, 3-(pyridyl-4-thio)propyl, 2-(5-methyl-1,3,4-thiadiazol-2-ylthio)ethyl, 2-(pyrimidin-4-ylthio)ethyl, 4-(1,3,4-triazol-2-ylthio)butyl, and like heterocyclic substituted alkyl groups. Further when A is $C_1$–$C_4$ alkyl substituted by a heterocyclic amino groups $R_3NH$-examples of A are 2-(2-thienylamino)ethyl, 4-(2-furylamino)butyl, 2-aminothiazol-4-ylaminomethyl, 2-(pyrimidin-2-ylamino)ethyl, and the like. Further when A is $C_1$–$C_4$ alkyl substituted by a quaternary heterocyclic examples of A are 2-(1-methylpyridinium-3-yl)ethyl, 2-(1-acetonylpyridinium-3-yl)ethyl, 2-(3-methylthiazolium-4-yl)ethyl, 3-(1-ethylpyrimidinium-4-yl)propyl, and such groups as the halide, sulfate, or nitrate.

When A in Formula (1) is a group of the formula —$CH_2$—$\oplus R_4$, examples of such groups are represented by the formula

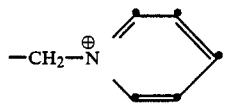

wherein the pyridinium ring can be substituted as defined hereinabove. Examples of pyridines and bicyclic pyridines which form the compounds having the —$CH_2 \oplus R_4$ pyridinium substituted 3-keto group are pyridine, 4-methylpyridine, 3-ethylpyridine, 4-hydroxypyridine, 3-hydroxypyridine, 4-carboxypyridine, 2-carboxypyridine, 3-carbamoylpyridine, 4-carbamoylpyridine, 3-chloropyridine, 4-chloropyridine, 3-chloro-4-hydroxypyridine, 3-trifluoromethylpyridine, 2-fluoropyridine, 4-fluoropyridine, 4-isopropylpyridine, 4-methoxycarbonylpyridine, 3,4-diethylpyridine, 3-methyl-4-trifluoromethylpyridine, 3-methylthiopyridine, 4-methylthiopyridine, 4-isopropylthiopyridine, 3-cyanopyridine, 3-methoxypyridine, 4-ethoxypyridine, 3-hydroxy-4-ethoxypyridine, 4-cyanopyridine, 3-aminopyridine, and like pyridines.

Examples of bicyclic pyridines forming the group —$CH_2 \oplus R_4$ as defined hereinabove are quinoline, isoquinoline, 4-hydroxyquinoline, 4-hydroxyisoquinoline, 6-hydroxyisoquinoline, 5-hydroxyisoquinoline, 7-chloroquinoline, 7-chloroisoquinoline, 8-hydroxyisoquinoline, 4-chloro-8-hydroxyisoquinoline, 4-ethylquinoline, 5-methylquinoline, 6-aminoquinoline, 4-trifluoromethylquinoline, 6,7-dimethoxyisoquinoline, 5-ethoxyquinoline, 5,6,7,8-tetrahydroquinoline, 5,6,7,8-tetrahydroisoquinoline, 2,3-cyclopentanopyridine, thieno[2,3-b]pyridine, thieno[3,2-b]pyridine, thieno[2,3-c]pyridine, thieno[3,2-c]pyridine, 2-methylthieno[3,2-c]pyridine, 2-carboxythieno[3,2-b]pyridine, furo[2,3-b]pyridine, furo[3,2-b]pyridine, furo[2,3-c]pyridine, furo[3,2-c]pyridine, thiazolopyridine, oxazolopyridine, imidazolopyridine, 2-methylthiazolopyridine, 1-methylimidazolopyridine, 2,6-naphthyridine, and like bicyclic pyridines.

Examples of thiazoles forming thiazoliummethyl substituted 3-keto-1-carbacephalosporins wherein $\oplus R_4$ is a thiazolium radical are thiazole, 2-aminothiazole, 2-methylthiothiazole, 2-methylthiazole, 2-chlorothiazole, 4-ethylthiazole, 2-chloro-4-methoxythiazole, 4,5-dimethylthiazole, 4,5-diethylthiazole, 4-ethyl-5-methylthiazole, tetrahydrobenzthiazole, 4,5-cyclopentanothiazole, 4-methyl-5-(2-hydroxyethyl)thiazole, 4-(2-hydroxyethyl)thiazole, 4-ethyl-5-(2-hydroxyethyl)thiazole, 2-methylthio-4-methyl-5-(2-hydroxyethyl)thiazole, 2-trifluoromethylthiazole, 2-methoxy-4-methylthiazole, 2-hydroxy-5-ethylthiazole, 4-carbamoylthiazole, 4-ethoxycarbonylthiazole, and like thiazoles.

Examples of A in Formula (1) when A is a heterocyclic amino group are 2-thienylamino, 2-furylamino, 2-pyrimidylamino, 2-imidazolylamino, 2-amionthiazol-4-ylamino, oxazol-2-ylamino, thiazol-2-ylamino, 1,3,4-thiadiazol-2-ylamino, and like groups.

When in Formula (1) A is a carboxy group or a derivative of a carboxy group, the 3-substituent of the 1-carbacephalosporin is represented by the formula

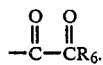

Examples of such groups are glyoxyl, —C(O)CHO, when $R_6$ is hydrogen; —C(O)COOH when $R_6$ is hydroxy; and the $C_1$–$C_4$ alkyl and phenyl esters thereof. Examples of A groups (—$COR_6$) are represented when $R_6$ is methoxy, ethoxy, phenoxy, 4-chlorophenoxy, amino, dimethylamino, trimethylsilyloxy, and like groups. Further when A is $COR_6$, $R_6$ can be phenyl or $C_1$–$C_4$ alkyl to form 3-substituents represented by the formulae —C(O)C(O)—$C_6H_5$ and —C(O)C(O)—$CH_3$.

The terms substituted phenyl, substituted phenoxy, substituted phenylthio, and substituted anilino, when used herein refer to such groups substituted on the phenyl ring by one or two of the same or different groups selected from among $C_1$–$C_4$ alkyl, $C_1$–$C_4$ alkoxy, methylenedioxy, halo, hydroxy, amino, $C_1$–$C_4$ alkylamino, di-($C_1$–$C_4$ alkyl)amino, $C_1$–$C_4$ alkanoylamino, carboxy, carbamoyl, cyano, trifluoromethyl, and $C_1$–$C_4$ alkanoyl. Examples of such substituted groups are 4-hydroxyphenyl, 4-methylphenyl, 4-chlorophenyl, 3-chloro-4-hydroxyphenyl, 4-methoxypheyl, 3,4-methylenedioxyphenyl, 3-aminophenyl, 4-chlorophenoxy, 3-ethylphenoxy, 3-hydroxyphenoxy, 2-fluorophenoxy, 4-trifluoromethylphenoxy, 2,4-dimethylphenoxy, 4-chlorophenylthio; 3,4-dichlorophenylthio, 2-methoxyphenylthio; 4-fluorophenylthio, 3-acetylaminophenylthio; 3-cyanophenylthio; 4-methylanilino, 2,4-dimethylanilino, 3-carboxyanilino, 4-methoxyanilino, 4-chloroanilino, 3-bromoanilino, 3-chloro-4-ethoxyanilino, 4-cyanoanilino, 4-carbamoylanilino, and like substituted groups.

The 1-carbacephalosporins represented by Formula (1) wherein $R_2$ is a carboxy-protecting group are intermediates useful in the preparation of antibiotic compounds wherein $R_2$ is hydrogen or a pharmaceutically acceptable salt. The carboxy group is desirably protected during the preparation of the 1-carbacephalosporins to block or prevent undesired reactions from occurring. The protecting group is a conventional carboxy-protecting group commonly used in the preparation of β-lactam antibiotic compounds such as the cephalosporin antibiotics and the penicillin antibiotics. Examples of $R_2$ carboxy-protecting groups are t-butyl, t-amyl, iodoethyl, 2,2,2-trichloroethyl, 2,2,2-tribromoethyl, phenacyl, chlorophenacyl, benzyl, p-nitrobenzyl, p-methoxybenzyl, diphenylmethyl, 4-methoxydiphenylmethyl, 4,4'-dimethoxydiphenylmethyl, trialkylsilyl esters such as trimethylsilyl, triethylsilyl, t-butyldimethylsilyl, β-(trimethylsilyl)ethyl, and like protecting groups. As noted above, the function of the protecting group is to block the otherwise reactive acidic carboxy group from participating in reactions in competiton with a desired reaction at another site in the molecule. Such groups are used for the temporary blocking function during the preparation of intermediates and final products as described hereinafter.

The 1-carbacephalosporins provided herein can be esterified with a biologically labile group to form esters which form the free acid antibiotic form in vivo. When in Formula (1) $R_2$ is a biologically labile ester, $R_2$ is an acyloxymethyl group represented by the formula

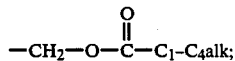

an acyloxyalkyl group represented by the formulae

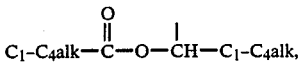

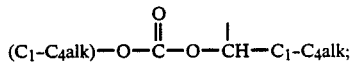

an acyloxyalkyl group represented by the above formula wherein $C_1$–$C_4$alk is substituted by amino; substituted amino, e.g., diethylamino or morpholino; an alkylamido group represented by the formula

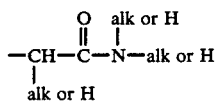

wherein alk is $C_1$–$C_6$ alkyl or $C_1$–$C_6$ alkyl substituted by amino; a dialkyl ether group represented by the formula

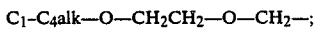

phthalidyl, indanyl, or the 5-methyl-2-oxo-1,3-dioxolen-4-methyl-4'-ylcyclocarbonate group represented by the formula

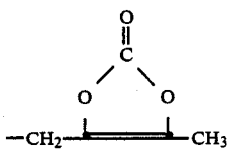

Examples of acyloxymethyl groups, $R_2$, are acetoxymethyl, propionoxymethyl and pivaloyloxymethyl. acyloxyalkyl groups are exemplified by 1-acetoxyethyl, 1-acetoxypropyl, 1-acetoxy-3-aminopropyl and 1-propionoxybutyl. Examples of alkylamido ester residues are carbamoylmethyl, 1-carbamoylethyl, 1-carbamoylpropyl, 1-(N-methycarbamoyl)ethyl, and 1-(N,N-diethylcarbamoyl)ethyl. Examples of dialkyl ether ester groups are β-methoxyethoxymethyl, β-ethoxyethoxymethyl, and β-t-butyloxyethoxymethyl.

Further examples of biologically-labile esters of the present invention include those provided in European Patent Application Nos. 159,899, 134,132, 128,029, 128,027, and 128,028, incorporated herein by reference.

The biologically labile esters of the 1-carbacephalosporins can be used as pro-drugs and can provide ease of formulation and administration of the antibiotic.

The 1-carbacephalosporins represented by Formula (1) can be prepared in the process of this invention with a 3β-protected amino-4β-(2-substituted-ethyl)azetidin-2-one represented by Formula (AA):

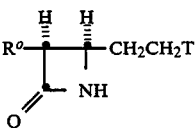
(AA)

wherein $R^o$ represents an amino group substituted by a conventional amino-protecting group, and T is a leaving group such as bromo, iodo, methanesulfonyloxy, trifluoromethylsulfonyloxy, or p-toluenesulfonyloxy. The azetidine (AA) is condensed with a phenylsulfinyl or phenylsulfonyl substituted acrylic acid ester represented by Formula (BB):

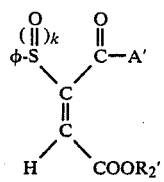
(BB)

wherein A' is defined hereinafter, k is 1 or 2, and $R_2'$ is a carboxy-protecting group, to provide a 7β-protected amino-1-carba-3-cephem ester represented by Formula (2):

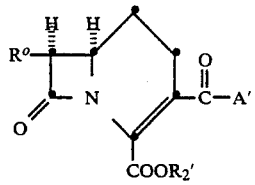
(2)

The condensation of (AA) with (BB) is preferably carried out in an inert aprotic solvent under substantially anhydrous conditions at a temperature between about −90° C. and about −45° C. with a strong non-nucleophilic base.

Inert aprotic solvents which can be used are aprotic organic solvents, for example, tetrahydrofuran, tetrahydropyran, dioxane, acetonitrile, diethyl ether, dimethylformamide, dimethylacetamide, 1,2-dimethoxyethane, and like solvents. Mixtures of such solvents may be used.

Non-nucleophilic bases which can be used include the silylated lithium amides such as bis(tri-$C_1$-$C_4$ alkylsilyl)lithium amides, e.g., bis-(trimethylsilyl)lithium amide, lithium diisopropylamide (LDA), sodium or potassium hexamethyldisilazide, and like bases.

For best results the base, the acrylic acid ester (BB) and the 4-(2-substituted-ethyl)azetidinone (AA) are used in about equimolar amounts.

The process is carried out by first adding the non-nucleophilic base to a cold solution of (AA), in an inert solvent. The solution is stirred in the cold for a time sufficient to allow generation of the anion formed with the base and the azetidinone nitrogen. Generally, the mixture is stirred in the cold for about 20 minutes to about one hour. Next, the phenylsulfinyl acrylic acid ester (BB), or a solution thereof in an inert aprotic solvent is added to the cold basic solution. The reaction mixture is stirred for a short time in the cold and then is allowed to warm slowly to room temperature. Prior to warming, the addition of a small amount of DMPU (approximately 20 mole percent) (1,3-dimethyl-3,4,5,6-tetrahydro-2(1H)pyrimidinone) to the reaction mixture appears to enhance the yield of the product. Stirring is continued for about 30 minutes to about one hour after the mixture has warmed to room temperature to complete the condensation.

The 7β-protected amino-1-carba-3-cephem ester, (2), is recovered from the reaction mixture by extraction into a water immiscible organic solvent. The solution is evaporated and the reaction product mixture dissolved in toluene, a higher boiling glycol ether, chlorobenzene or other inert solvent having a suitable boiling point, and heated at a temperature above about 85° C., preferably above 100° C., for about 15 minutes to about 4 hours to complete the elimination of the phenylsulfinic acid residue, or the phenylsulfonic acid residue. The solvent is removed and the product is purified by chromatography over a suitable adsorbent such as silica gel. When the process is carried out on a small scale, the product may be purified by HPLC or by preparative thick layer chromatography.

The 7β-protected amino-1-carba-3-cephem ester product (2) is then deprotected and N-acylated with the desired carboxylic acid, RCOOH, or an active derivative thereof, to provide the compound represented by the formula 1 wherein $R_2$ is a carboxy-protecting group.

A' in the above Formula (BB) has the same meanings as defined for radical A in Formula (1), except that A'0 is other than hydroxy, halo, a quaternary heterocyclic as defined above, a group containing $SR^3$ of the group —$CH_2 \oplus R_4$, and when A' contains a free amino or free carboxy substituent, the substituent is blocked with a conventional protecting group.

Following the cyclocondensation described above, the product (Formula (2)) is converted to the compound of Formula (1). For instance, when A' is a group other than a group as defined for A (Formula (1)), A' is converted to A, the 7-amino-protecting group is removed, and the 7-amino substituted intermediate is N-acylated with the desired carboxylic acid RCOOH or an active derivative thereof to provide the 7-acylamino-1-carba-3-cephem represented by Formula (1). For example, when A' in Formula (BB) is an acyloxymethyl group such as —$CH_2OCOCH_3$, the cyclocondensation product (2) is further reacted with a thiol, such as 1H-tetrazole-5-thiol to form the intermediate wherein A' is the group —$CH_2$—S—$R_3$. Likewise, the acetoxymethyl group may be reacted with a pyridine or a substituted pyridine to form the group —$CH_2 \oplus R_4$. Upon removal of the protecting group of $R^o$ and N-acylation, a compound of Formula (1) is obtained.

The amino-protected-azetidin-2-one (AA) is prepared as shown below in Scheme 1 by the cycloaddition of the imine (formed with benzylamine and 3-t-butyldimethylsilyloxy)propionaldehyde) with the chiral auxiliary 4(S)-phenyl-1,3-oxazolidin-2-one-3-ylacetyl chloride (step 1). (For a description of the preparation of this chiral auxiliary, see Evans and Sjogren, *Tetrahedron Letters*, Vol. 26, No. 32, pp. 3783–3786, 1985.) The imine is formed in dry toluene in the presence of a drying agent such as molecular sieves or via azeotropic distillation of water. The chiral oxazolidinone acetyl chloride then is allowed to react with the previously prepared imine in methylene chloride at a temperature between about −80° C. and about −15° C. in the presence of a tertiary amine such as triethylamine. The cycloaddition product (a), N-benzyl-3β-[(4S)-phenyl-1,3-oxazolidin-2-one-3-ylacetylamino]-4β-(2-t-butyldimethylsilyloxyethyl)azetidin-2-one, is reduced with lithium in ammonia containing t-butyl alcohol (step 2) to remove the chiral auxiliary and the N-benzyl group to provide (b) the 3β-amino-4β-(2-t-butyldimethylsilyloxyethyl)azetidin-2-one. The β-amino group is protected (step 3) with a suitable conventional amino-protecting group such as the t-butyloxycarbonyl group (tBOC). The amino-protected azetidinone (c) is reacted (step 4) in an inert solvent at a temperature of about 0° C. to about room temperature with tetra(n-butyl)ammonium fluoride to cleave the silyl ether and form 3β-protected amino-4β-(2-hyroxyethyl)azetidin-2-one (d).

The hydroxy group is converted in step 5 to the mesylate, triflate, or tosylate ester (e) with methanesulfonyl chloride, trifluoromethylsulfonyl chloride, or tosychloride in the presence of a tertiary amine such as triethylamine or pyridine. In step 6 the ester is reacted in acetone at room temperature with sodium iodide or sodium bromide to form the 2-haloethylazetidin-2-one (AA) (T=Cl or Br). Preferably the 2-iodoethylazetidinone is employed in the process for preparing compounds represented by Formula (2).

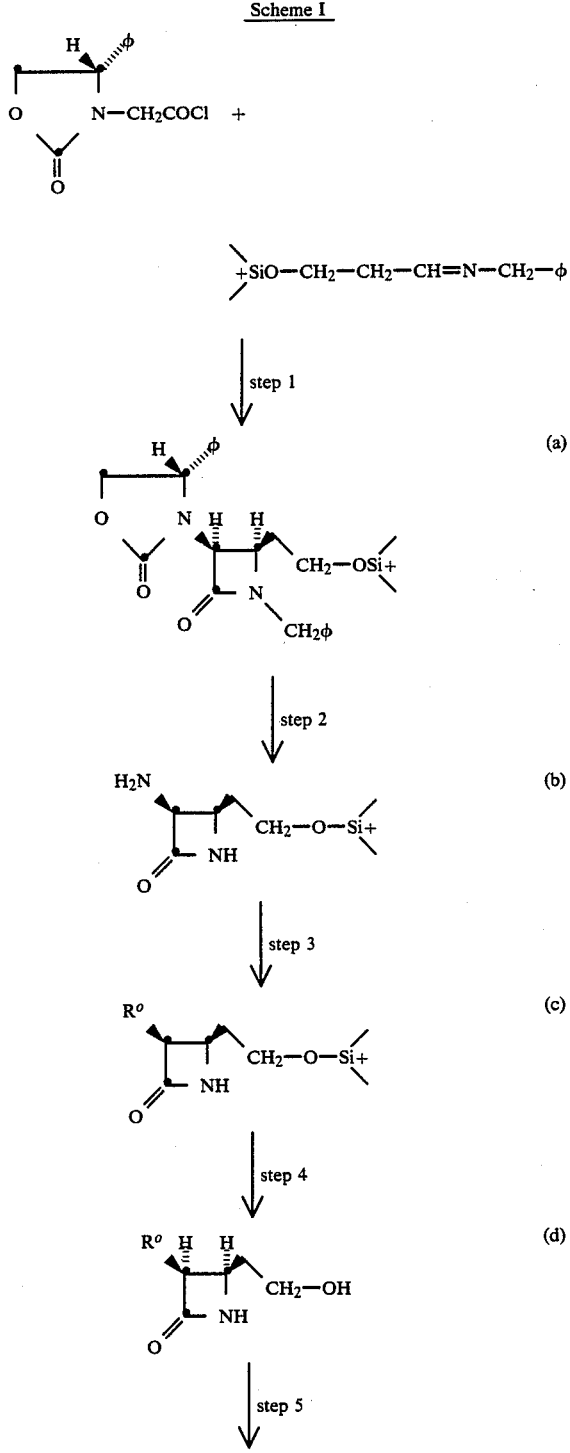

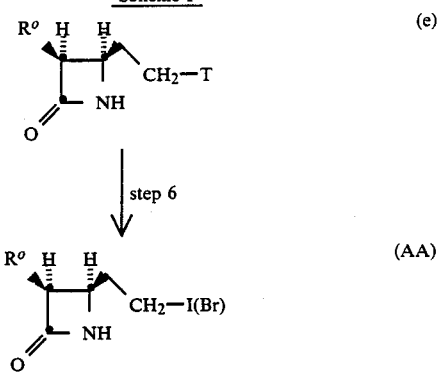

In Scheme 1, φ is phenyl; R⁰ is protected amino; and

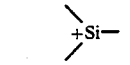

is t-butyldimethylsilyl.

The phenylsulfinyl-substituted or phenylsulfonyl-substituted acrylic acid ester represented by the foregoing Formula (BB) is prepared as shown below in Scheme 2.

In general, an ester of phenylmercaptoacetic acid or a phenylthiomethylketone is alkylated (step 1) with a haloacetic acid ester to form a 3-phenylthio-3-substituted propionic acid ester (aa). Chlorination (step 2) of (aa) with N-chlorosuccinimide in carbon tetrachloride-THF at the reflux temperature provides the 3-chloro-3-phenylthio-3-substituted propionic acid ester (bb).

Dehydrohalogenation (step 3) of (bb) with a strong non-nucleophilic base such as DBU forms the 3-phenylthio-3-substituted acrylic acid ester (cc) as a mixture of the two geometric isomers. For purposes of preparing the 1-carba-3-cephem compounds of the formula 1, the mixture need not be separated into the individual isomers.

In step 4 the phenylthio group of (cc) is oxidized in methylene chloride at room temperature or below with a peracid such as peracetic acid to provide (BB).

The oxidation can be carried out in an inert organic solvent such as methylene chloride. Peracetic acid is best used in preparing the phenylsulfinyl intermediates (Formula (BB), k=1) whereas m-chloroperbenzoic acid can be used to prepare the phenylsulfonyl intermediates (BB) wherein k is 2.

The phenylsulfinyl-substituted intermediates represented by Formula (BB) wherein k is 1 are preferred intermediates in the preparation of 1-carbacephalosporins.

Scheme 2

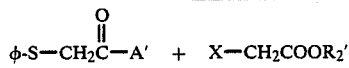

-continued
Scheme 2

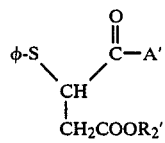

↓ step 2

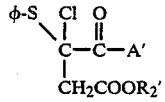

↓ step 3

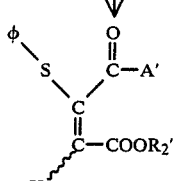

↓ step 4

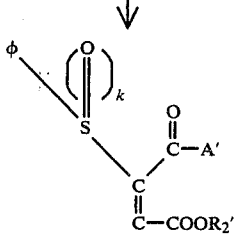

In Scheme 2, φ-phenyl; X is chloro, bromo, or iodo; R₂' is a carboxy-protecting ester group; and A' is a group represented by A in Formula (1) other than groups that are incompatible in the reaction steps outlined in Scheme 2, e.g., groups that will undergo mild peracid oxidation, chlorination with a positive chlorination reagent such as N-chlorosuccinimide, or that are incompatible in the alkylation or dehydrohalogenation steps. For example, A' is A as defined above except when A is hydroxy, halogen, azido, $C_2$–$C_6$ alkenyloxy, $C_2$–$C_6$ alkynyloxy, or $C_1$–$C_4$ alkyl, or $C_1$–$C_4$ alkoxy substituted by the group —SR₃. It will be recognized that when A' contains a group reactive under the conditions in Scheme 2 for preparing (BB), that such group can be temporarily protected or blocked with a conventional blocking group to prevent its reaction in competition with the desired reaction. For example, when A' is a group containing a free amino or free carboxy substituent, these groups can be protected with a conventional protecting group.

In an example of the preparation of the 3-substituted acrylate (BB) via Scheme 2, methyl phenylmercaptoacetate is alkylated with t-butyl bromoacetate to form t-butyl 3-phenylthio-3-methoxycarbonylpropionate. The diester is chlorinated with N-chlorosuccinimide and the chloro product is reacted with the base DBU to form the unsaturated diester represented by the formula (aa)

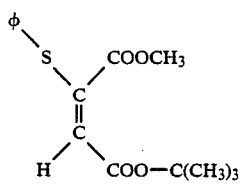

Oxidation of the diester with peracetic acid yields the corresponding phenylsulfinyl ester represented by the above Formula (BB) wherein A' is methoxy and R₂' is t-butyl.

The diester described above is a versatile intermediate which can be converted to a variety of other intermediates represented by (BB). Thus, the t-butyl group can be selectively removed with trifluoroacetic acid (TFA) in the cold to form the mono ester and the free carboxy group re-esterified to form a different mixed diester. For example, the mixed methyl t-butyl diester of the above formula is treated with TFA to form the mono ester of the formula (bb)

(cc)

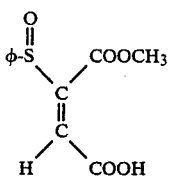

(BB)

The monoester is then esterified with the desired ester forming group to form a different mixed diester. For example, the free acid is esterified with allyl bromide in the presence of triethylamine to form the mixed methyl allyl diester represented by the formula

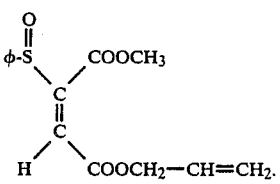

The methyl ester group of the above mixed methyl t-butyl diester sulfide likewise can be selectively deesterified to the mono t-butyl ester and the free carboxy group reesterified to a different mixed diester. Alternatively, the free carboxy group can be converted to another carboxy derivative represented by (A), e.g., an amide, and then used in the cyclization reaction with the intermediate of Formula (AA) to form the corresponding 1-carba-3-cephem represented by Formula (1) wherein R₂ is the carboxy-protecting group R₂' of (BB). Accordingly, the mixed methyl t-butyl diester represented by the formula

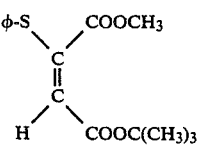

prepared via steps 1 through 3 of Scheme 2 is treated in THF with an equimolar amount of lithium hydroxide to form the mono t-butyl ester represented by the formula

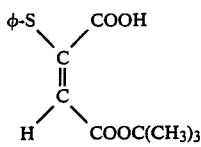

The carboxy group can be reesterified with the desired ester forming reagent or converted to another carboxy derivative such as an acid halide, azide, or amide. Following the reesterification or conversion to a carboxy derivative, the product is oxidized with a peracid to the corresponding phenylsulfinyl or phenylsulfonyl derivative (BB).

In another example of the preparation of a 3-phenylsulfinyl-3-substituted-acrylate (BB), the ketone, phenylthioacetone is alkylated in THF with t-butyl bromoacetate and sodium hydride to yield t-butyl 3-phenylthio-4-oxopentanoate. The keto ester is chlorinated in THF with N-chlorosuccinimide to the 3-chloro keto ester and the latter dehydrohalogenated to t-butyl 3-phenylthio-4-oxopent-2-eneoate. The unsaturated keto ester is then oxidized in methylene chloride with peracetic acid to (BB) wherein A' is methyl and $R_2'$ is t-butyl as represented by the following formula

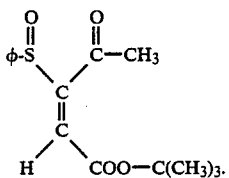

Examples of substituted acrylate esters represented by Formula (BB) which can be obtained by the above-described methods as shown in the following Table 1.

TABLE I

| A' | $R_2'$ |
|---|---|
| —$C_2H_5$ | t-butyl |
| —$OCH_3$ | t-butyl |
| —$CH_2C_6H_5$ | t-butyl |
| —$C_6H_5$ | pMB[1] |
| —$NH_2$ | $C_2H_5$ |
| —OH | $CH_3$ |
| —$OCH_2CH_2OH$ | t-butyl |
| —$OCH_2CH_2$—$SCH_3$ | benzyl |
| —$N(CH_3)_2$ | $(CH_3)_3Si$ |
| —$NHC_2H_5$ | benzyl |
| —$NHCOCH_3$ | t-butyl |
| —$C(O)OCH_3$ | pNB[2] |
| —$OCH_2C_6H_5$ | pNB[2] |
| —$CH_2$—$CH_2N(CH_3)_2$ | pNB[2] |
| —$C_4H_9$ | $(CH_3)_3Si$ |
| —$C(O)NH_2$ | benzyl |
| 2-thienyl | benzyl |
| 2-furyl | t-butyl |
| imidazol-2-yl | t-butyl |
| thiazol-4-yl | t-butyl |
| oxazol-2-yl | $CH_3$— |
| pyrimidin-2-yl | $CCl_3CH_2$— |
| pyrrolidino | $CCl_3CH_2$— |
| piperidino | allyl |
| morpholino | allyl |
| N—ethylpiperazino | allyl |
| —$CH_3$ | benzyl |
| —$CH_2NHC_6H_5$ | benzyl |
| —O—$CH_2CH_2NH$pyridyl | t-butyl |
| —O—$CH_2CH_2$—1-methyl-pyridinium | t-butyl |
| —NH—$CH_2CH_2$—NH—pyrimidin-2-yl | allyl |
| —$C(O)NHCH_3$ | allyl |
| —$C(O)H$ | allyl |
| —$C(O)C_6H_5$ | t-butyl |
| —$CH_2OC(O)NH_2$ | benzyl |
| —O—$(CH_2)_3$—$OC(O)NH_2$ | allyl |

[1]p-methoxybenzyl
[2]p-nitrobenzyl

Certain of the 1-carba-3-cephem compounds represented by Formula (1) can be obtained by further derivatization or substitution following the formation of the 1-carba-3-cephem with intermediates (AA) and (BB). Likewise, the amino-protected 1-carbacephalosporin represented by Formula (2) above can be substituted, deblocked, and N-acylated to provide a compound represented by Formula (1) as is shown below

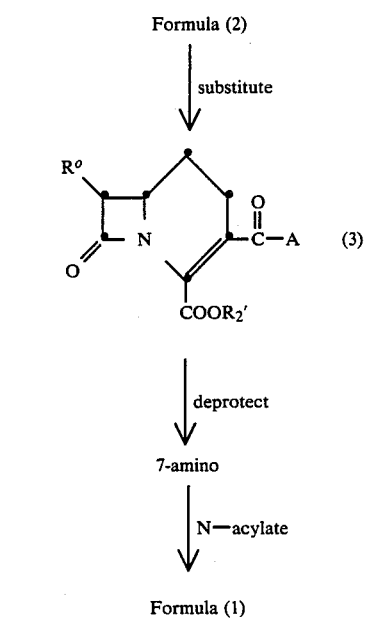

For example, a 7β-amino-protected-3-acetyl-1-carba-3-cephem ester represented by the formula

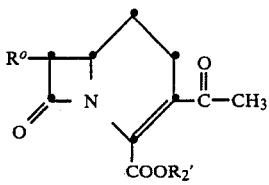

wherein $R^o$ and $R_2'$ have the above-defined meanings, which is prepared with intermediate (BB) wherein $A'$ is methyl, is reacted with bromine in the presence of a strong non-nucleophilic base such as LDA (lithium diisopropyl amide) to form the 3-bromoacetyl derivative represented by the formula

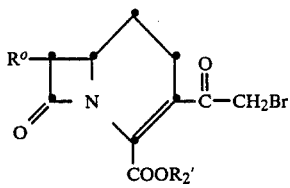

Likewise, the compound represented by the formula 2 wherein $A'$ is $C_1$–$C_4$ alkyl is converted to the bromo derivative via the silylated enol represented by the formula

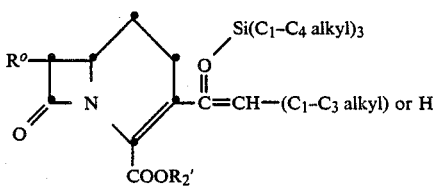

The bromination is best carried out with an N-bromoimide such as N-bromosuccinimide to form the 3-bromoacyl compound represented by the partial formula

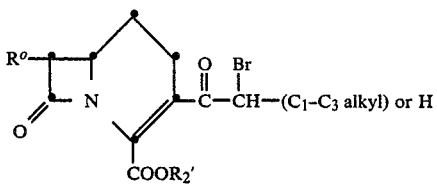

The silylated enol is prepared with the compound 2 wherein $A'$ is $C_1$–$C_4$ alkyl by treatment with a base such as 2,6-lutidine and a trialkylsilyl triflate, e.g., dimethyl-t-butylsilyl triflate or trimethylsilyl triflate. For example, an amino-protected 7β-amino-3-acetyl-1-carba-3-cephem-4-carboxylic acid ester is treated in methylene chloride with 2,6-lutidine followed by t-butyldimethylsilyl triflate. The t-butyldimethylsilylated enol [3-(1-hydroxyethene)] is isolated by extraction, purified by chromatography, and reacted in an inert solvent such as THF with N-bromosuccinimide to provide the 7β-protected amino-3-bromoacetyl-1-carba ester. The 3-bromoacetyl ester is reacted with an O, S, or N nucleophile to provide a 3β-protected amino 1-carba-3-cephem ester and the latter is deprotected and N-acylated to a compound of Formula (1). For example, the 3-bromoacetyl ester can be reacted with a 5- or 6-membered nitrogen containing heterocyclic thiol or an alkali metal salt thereof to form the compound wherein A is the group —$CH_2SR_3$. Removal of the amino-protecting group of $R^o$ and N-acylation with the desired carboxylic acid, RCOOH, provides the corresponding 3-substituted ester represented by the Formula (1). Deesterification provides (1) wherein $R_2$ is hydrogen.

Likewise, the 3-bromoacetyl ester can be reacted with pyridine, a substituted pyridine, or other nitrogen heterocyclic represented by $R_4$ in Formula (1) to provide the quaternary bromide salt represented by Formula (3) wherein A is the group —$CH_2^{\oplus}R_4X^{\ominus}$. For example, t-butyl 3β-t-butyloxycarbonylamino-3-bromoacetyl-1-carba-3-cephem-4-carboxylate is treated in an inert solvent such as THF, acetone, or acetonitrile with 1.1 equivalents of pyridine to form t-butyl 3β-t-butyloxycarbonylamino-3-pyridiniummethylcarbonyl-1-carba-3-cephem-4-carboxylate bromide represented by the formula

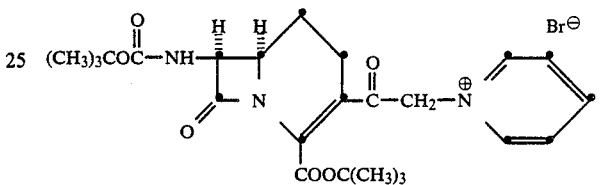

In an alternative method for preparing the compounds represented by Formula (3) wherein A is —$CH_2^{\oplus}R_4X^{\ominus}$, the 3-bromoacetyl ester is reacted with an alkali metal carboxylate such as sodium acetate in an aqueous medium containing a water miscible organic solvent to provide the corresponding 3-acetoxymethylcarbonyl-1-carba ester as shown below.

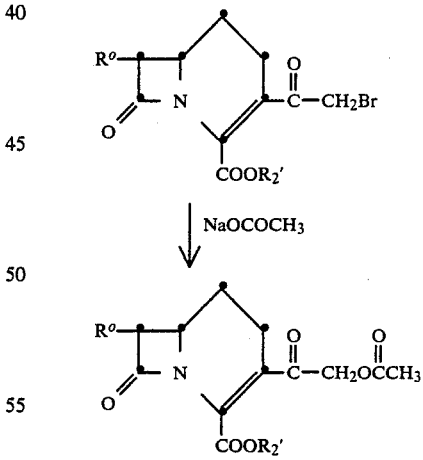

The acetoxy group can be displaced in aqueous acetone with warming to about 60° C. with an $R_4$ nitrogen heterocycle such as pyridine to provide the corresponding 3-pyridiniummethyl-1-carba-3-cephem ester represented by Formula (3) wherein A is pyridiniummethyl.

The amino-protecting group is removed from the 3β-amino group of the above pyridinium product and the free amino group is N-acylated with the desired carboxylic acid, RCOOH, or a carboxy-activated derivative thereof, to provide (1) as an ester.

The above derivative-forming reactions also can be carried out on a compound of Formula (1) wherein A is methyl as shown in the following scheme.

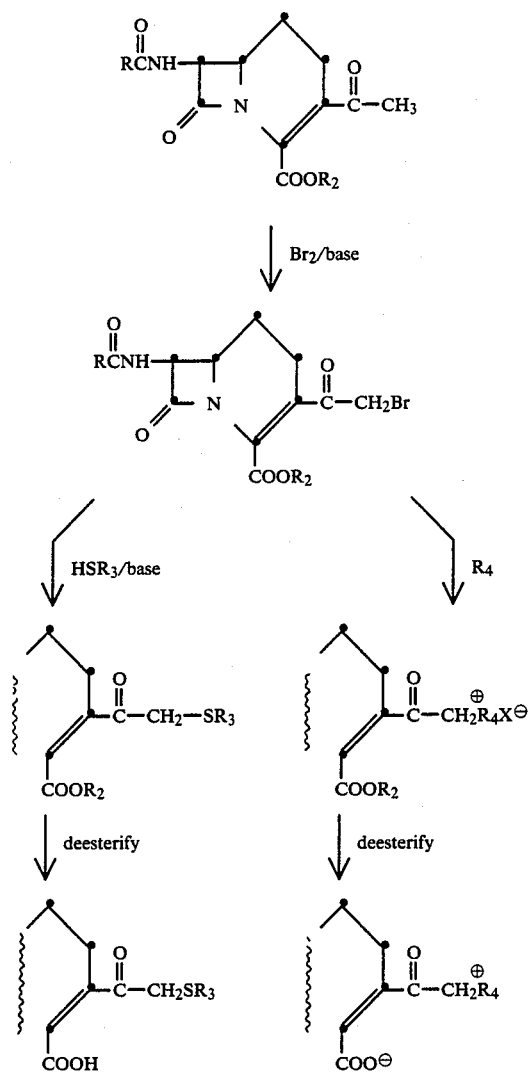

The 7β-acylamino-7α-substituted-1-carbacephalosporins represented by Formula (1) wherein $R_1$ is $C_1$-$C_4$ alkoxy are prepared according to the method described by Koppel, U.S. Pat. No. 3,994,885. Preferably, compounds of Formula (1) wherein $R_1$ is $C_1$-$C_4$ alkoxy, are prepared by the method outlined in the scheme below:

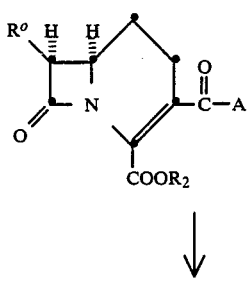

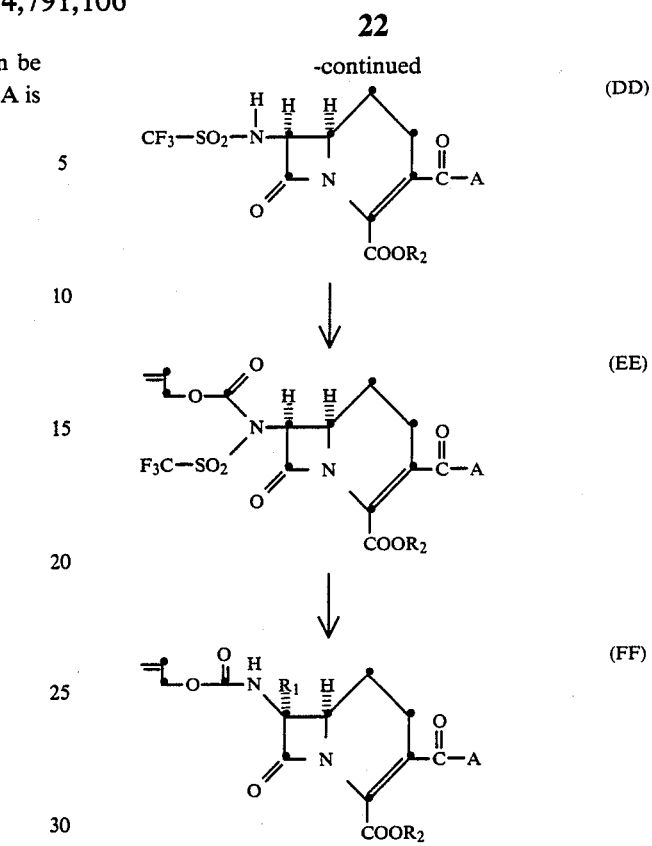

In the above scheme, if $R^o$ is an amino group substituted by the t-butoxycarbonyl protecting group, (CC) is treated with p-toluenesulfonic acid in ethanol at approximately 45° C. Once the t-butoxycarbonyl group removal is complete, the product is taken up into toluene and concentrated to dryness. The tosylate salt is then treated with trifluoromethanesulfonic anhydride and N-methyl morpholine to provide (DD). (DD) is then treated with allyloxycarbonyl chloride in $CH_2Cl_2$ in the presence of base to provide (EE).

The compounds of the invention wherein $R_1$ is $C_1$-$C_4$ alkoxy are then provided by reacting a compound of Formula (EE) with a $C_1$-$C_4$ alcohol in $CH_2Cl_2$, in the presence of a base.

The 7α-formamido substituted compounds wherein $R_1$ is —NHCHO are obtained by the method described by Millner, U.S. Pat. No. 4,539,159. According to this method, a 7β-acylamino- or 7β-protected amino-7β-methylthio-substituted 1-carbacephalosporin is reacted with anhydrous ammonia or an ammonium salt in the presence of mercuric acetate to form the corresponding 7α-amino derivative. The latter is formylated to the 7α-formamido derivative.

In the description of the preparation of the 1-carbacephalosporins provided herein the term amino-protecting group refers to the conventional amino-protecting groups commonly used in the β-lactam art for the temporary protection of the amino group. These protecting or blocking groups mask the amino group while reactions at other sites in the molecule are carried out. Numerous amino-protecting groups are known and are commonly used in the preparation of the β-lactam antibiotics. Examples of such groups are the alkyl(or alkenyl)oxycarbonyl and aryloxycarbonyl groups, e.g., ethoxycarbonyl, 2,2,2-trichloroethoxycarbonyl, cyclopentyloxycarbonyl, allyloxycarbonyl, benzyloxycarbonyl, p-nitrobenzyloxycarbonyl, t-butyloxycarbonyl, and t-amyloxycarbonyl; the enamine-protected amino groups such as those formed with the β-keto esters and the amino group, e.g., methyl or ethyl acetoacetate; 2,4-dinitrophenylsulfenyl, acetyl, chloroacetyl, dichloroacetyl, 4-methoxy-2,3,6-trimethylbenzenesulfonyl, trityl, and like amino-protecting groups.

The protected amino groups $R^o$ is distinguished from the 7-acylamino group R of Formula (1) in that the former are used during synthesis while the latter form part of the antibiotic compound.

The 1-carba(1-dethia)cephalosporins of this invention (Formula (1)) possess the 7-position side chain of a known cephalosporin or the 6-position side chain of a known penicillin antibiotic. Preferred compounds of the invention are represented by Formula (1) where, in the 7-position acyl group RC(O)—, R is hydrogen; $C_1$-$C_6$ alkyl, $C_1$-$C_6$ alkyl substituted by cyano, carboxy, halogen, amino, $C_1$-$C_4$ alkoxy, $C_1$-$C_4$ alkylthio, or trifluoromethylthio;

a phenyl or substituted phenyl group represented by the formula

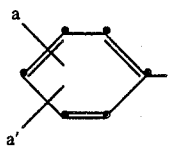

wherein a and a' independently are hydrogen, halogen, hydroxy, $C_1$-$C_4$ alkoxy, $C_1$-$C_4$ alkanoyloxy, $C_1$-$C_4$ alkyl, $C_1$-$C_4$ alkylthio, amino, $C_1$-$C_4$ alkanoylamino, $C_1$-$C_4$ alkylsulfonylamino, carboxy, carbamoyl, aminosulfonyl, hydroxymethyl, aminomethyl, or carboxymethyl;

a group represented by the formula

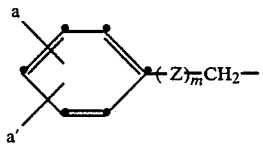

wherein a and a' have the same meanings as defined above, Z is O or S, and m is 0 or 1;

a heteroarylmethyl group represented by the formula

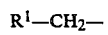

wherein $R^1$ is thienyl, furyl, benzothienyl, benzofuryl, pyridyl, 4-pyridylthio pyrimidyl, pyridazinyl, indolyl, pyrazolyl, imidazolyl, triazolyl, tetrazolyl, oxazolyl, thiazolyl, oxadiazolyl, thiadiazolyl, and such heteroaryl groups substituted by amino, hydroxy, halogen, $C_1$-$C_4$ alkyl, $C_1$-$C_4$ alkoxy, $C_1$-$C_4$ alkylsulfonylamino;

a substituted methyl group represented by the formula

wherein $R^2$ is cyclohex-1,4-dienyl, or a phenyl group or substituted phenyl group represented by the formula

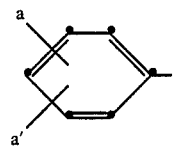

wherein a and a' have the above defined meanings, or $R^2$ is $R^1$ as defined above, and Q is hydroxy, $C_1$-$C_4$ alkanoyloxy, carboxy, sulfo, amino, sulfoamino or a substituted amino group represented by the formula

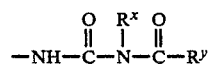

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group

wherein $R^x$ is hydrogen or $C_1$-$C_3$ alkyl, and $R^z$ is hydrogen, $C_1$-$C_3$ alkylsulfonyl, $C_1$-$C_3$ alkyl, or $C_1$-$C_4$ alkanoyl; or Q is a substituted amino group represented by the formula

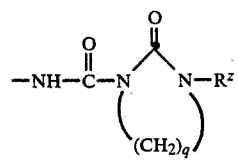

wherein $R^z$ has the same meanings as defined above and q is 2 or 3; or Q is a substituted amino group represented by the formula

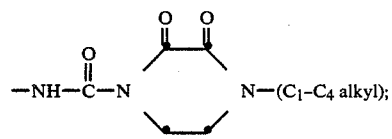

a benzamido group represented by the formula

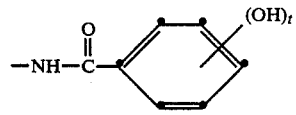

wherein t is 1 to 3; a pyridone or hydroxy-substituted pyridone group represented by the formula

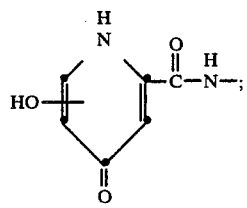

a pyridyl group represented by the formula

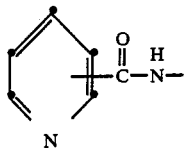

and such pyridyl group substituted by $C_1$-$C_4$ alkyl, amino, carboxy, hydroxy or halogen; an imidazoyl or pyrazolyl group represented by the formulae

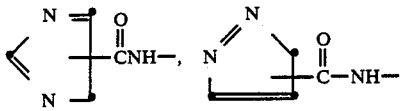

and such groups substituted by $C_1$-$C_4$ alkyl, carboxy, amino or halogen; a benzpyridazin-4-one-3-ylcarbonylamino group represented by the formulae

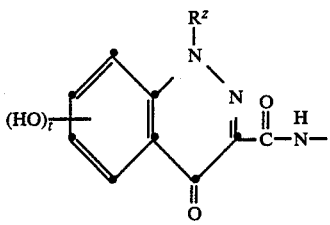

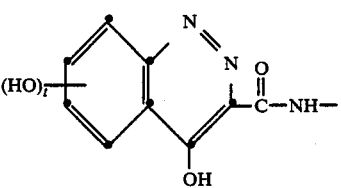

wherein $R^z$ is hydrogen or $C_1$-$C_4$ alkyl; and t is 1-3; or Q is a substituted amino group represented by the formula

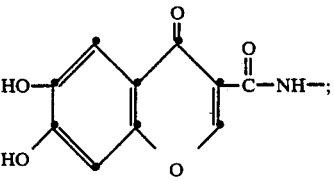

or R is a keto group or an oximino-substituted group represented by the formulae

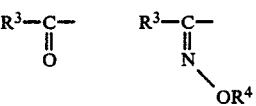

wherein $R^3$ is $R^1$ or $R^2$ as defined above and $R^4$ is hydrogen, $C_1$-$C_4$ alkyl, $C_1$-$C_4$ alkyl substituted by halogen, a carboxy-substituted alkyl or cycloalkyl group represented by the formula

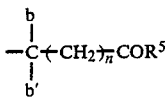

wherein
b and b' independently are hydrogen, or $C_1$-$C_3$ alkyl, n is 0, 1, 2, or 3; and b and b' when taken together with the carbon to which they are bonded form a 3- to 6-membered carbocyclic ring, and $R^5$ is hydroxy, $C_1$-$C_4$ alkoxy, amino, $C_1$-$C_4$ alkylamino, or di($C_1$-$C_4$ alkyl)amino;

or $R^4$ is $C_1$-$C_4$ substituted by phenyl or phenyl substituted by one or two of the same or different groups selected from among $C_1$-$C_4$ alkyl, hydroxy, halogen, carboxy or protected carboxy;

or $R^4$ is $C_1$-$C_4$ alkyl substituted by amino or protected amino;

or $R^4$ is $C_2$-$C_4$ alkenyl;

or $R^4$ is a cyclic lactam represented by the formula

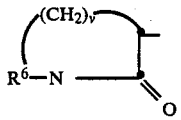

wherein
v is 2, 3, or 4; and $R^6$ is hydrogen or $C_1$-$C_3$ alkyl;

or $R^4$ is a heteroarylmethyl group represented by the formula

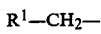

wherein $R^1$ has the same meanings as defined hereinabove.

In the above definition of the preferred compounds represented by Formula (1), $C_1$-$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups; $C_1$-$C_6$ alkyl substituted by cyano refers to cyanomethyl, cyanoethyl, 4-cyanobutyl, and the like; $C_1$-$C_6$ alkyl substituted by carboxy refers to such groups as carboxymethyl, 2-carboxyethyl, 2-carboxypropyl, 4-carboxybutyl, 5-carboxypentyl, and the like; $C_1$-$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$-$C_6$ alkyl substituted by amino refers to such groups as 2-aminoethyl, aminomethyl, 3-aminopropyl and 4-aminobutyl; $C_1$-$C_6$ alkyl substituted by $C_1$-$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like groups; $C_1$-$C_6$ alkyl substituted by $C_1$-$C_4$-alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$-$C_6$ alkyl substituted by trifluoromethyl is exemplified by 2,2,2-trifluoroethyl, 3,3,3-trifluoropropyl, 4,4,4-trifluorobutyl, and the like; and $C_1$-$C_6$ alkyl substituted by trifluoromethylthio refers to, for example, trifluoromethylthiomethyl, 2-(trifluoromethylthio)ethyl, 2-(trifluoromethylthio)propyl, 4-(trifluoromethylthio)- butyl, 5-(trifluoromethylthio)hexyl, and like $C_1$–$C_6$ alkyl substituted groups.

When in Formula (1) R is a substituted phenyl group wherein the substituent(s) are represented by a and a', examples of such groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylaminophenyl such a 3-methylsulfonylaminophenyl, 4-methylsulfonylaminophenyl, 3,5-(dimethylsulfonylamino)phenyl, 4-n-butylsulfonylaminophenyl, and 3-ethylsulfonylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO— groups of Formula (1) wherein R is a group represented by the formula

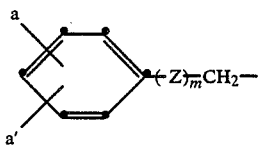

with m=0 are: penylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=O, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z=S, phenylthioacetyl, 4-chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R^1$—$CH_2CO$-groups of Formula (1) wherein $R^1$ is a heteroaryl group are: 2-thienylacetyl, 3-thienylacetyl, 2-furylacetyl, 2-benzothienylacetyl, 2-benzofurylacetyl, 3-benzothienylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, pyridyl-2-acetyl, pyridyl-3-acetyl, pyridyl-4-acetyl, 4-aminopyridyl-3-acetyl, pyrimidin-2-ylacetyl, pyrimidin-4-ylacetyl, 2-aminopyrimidin-4-ylacetyl, 4-aminopyrimidin-2-ylacetyl, pyridazin-3-acetyl, pyridazin-4-acetyl, pyrazol-3-ylacetyl, 3-methylpyrazol-1-ylacetyl, imidazol-2-ylacetyl, imidazol-1-ylacetyl, 2-aminoimidazol-3-ylacetyl, 3-chloroimidazol-4-ylacetyl, and like heteroaryl groups optionally substituted by amino, $C_1$–$C_4$ alkylsulfonylamino, hydroxy, halo, $C_1$–$C_4$ alkyl or $C_1$–$C_4$-alkoxy groups.

Examples of RCO— groups of Formula (1) compounds wherein R is a substituted methyl group represented by the formula $R^2$—CH(Q)— and Q is amino, carboxy, hydroxy, or sulfo, are 2-carboxy-2-phenylacetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-sulfoamino-2-phenylacetyl, 2-sulfoamino-2-(4-hydroxyphenyl)acetyl, 2-sulfoamino-2-(2-aminothiazol-4-yl)acetyl, 2-amino-2-(benzothien-2-yl)acetyl, 2-amino-2-(3-methylsulfonylphenyl)acetyl, 2-sulfoamino-2-(1,4-cyclohexadien)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzothien-2-yl)acetyl, and 2-hydroxy-2-(benzofur-2-yl)acetyl; and when Q is a substituted amino group represented by the formula

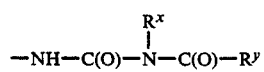

examples of such acyl groups are 2-(N-methyl-N-benzoylcarbamoylamino)-2-phenylacetyl, 2-(N-methyl-N-cinnamoylcarbamoylamino)-2-(2-furyl)acetyl, 2-(N,N-dimethylcarbamoylureido)-2-(4-chlorophenyl)acetyl, 2-[N-methyl-N-(2-chlorocinnamoyl)carbamoylamino]-2-(2-thienyl)acetyl, and 2-(N-ethyl-N-acetylcarbamoylamino)-2-(4-hydroxyphenyl)acetyl; and when Q is a substituted amino group represented by the formula

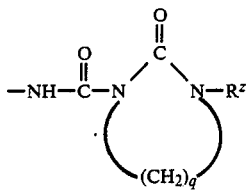

examples of acyl group R(CO— are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino]-2-phenylacetyl; and when Q is a hydroxy-substituted benzamido group represented by the formula

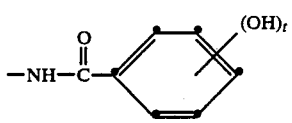

examples of such acyl groups are 2-(2,4-dihydroxybenzamido)-2-phenylacetyl, 2-(4-hydroxybenzamido)-2-(4-hydroxyphenyl)acetyl, 2-(3,4-dihydroxybenzamido)-2-(2-aminothiazol-4-yl)acetyl, 2-(3,5-dihydroxybenzamido)-2-(3-thienyl)acetyl, and 2-(2-hydroxybenzamido)-2-(2-benzofuryl)acetyl.

When Q is an hydroxy-substituted pyridine-carbonylamino group, examples include e.g., 2-hydroxypyridin-4-one-6-ylcarbonylamino and 3-hydroxypyridin-4-one-6-ylcarbonylamino. When Q is a pyridylcarbonyl amino group examples are e.g., pyridin-3-ylcarbonylamino, 4-aminopyridin-3-ylcarbonylamino, 5-chloropyridin-2-ylcarbonylamino, 3-carboxypyridin-4-ylcarbonylamino, and 4-aminopyridino-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-ylcarbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae (including the tautomeric form when $R^3=H$)

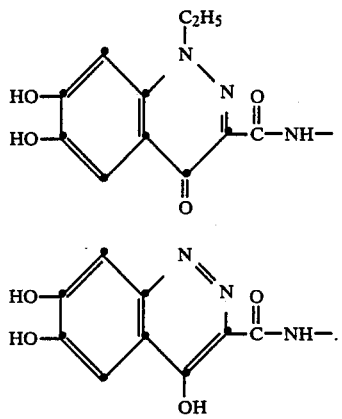

Examples of RCO acyl groups of the compounds represented by formula 1 when R is a keto group or an oximino-substituted group represented by the formulae

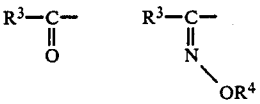

are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2-methoxyiminoacetyl, 2-(2-thienyl)-2-ethoxyiminoacetyl, 2-(2-furyl)-2-methoxyiminoacetyl, 2-(2-benzothienyl)-2-carboxy methoxyiminoacetyl, 2-(2-thienyl)-2-(2-carboxyethoxy)iminoacetyl, 2-(2-amino-1,2,4-thiadiazol-4-yl)-2-methoxyiminoacetyl, 2-(2-aminothiazol-4-yl)-2-methoxy iminoacetyl, 2-(2-aminothiazol-4-yl)-2-(4-hydroxybenzyloxyimino)acetyl, 2-(2-aminothiazol-4-yl)-2-(4-chlorobenzyloxyimino)acetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoylprop-2-yl)oxyiminoacetyl, 2-(5-amino-1,3,4-thiadiazol-2-yl)-2-methoxyiminoacetyl, 2-(2-aminothiazol-4-yl)-2-(pyrrolidin-2-one-yl)oxyiminoacetyl, 2-(2-aminothiazol-4-yl)-2-(1-methylpyrrolidin-2-one-3-yl)oxyiminoacetyl, 2-phenyl-2-(pyrrolidin-2-one-3-yl)oxyiminoacetyl, 2-(2-aminooxazol-4-yl)-2-(1-ethylpyrrolidin-2-one-3-yl)oxyiminoacetyl, 2-(2-aminothiazol-4-yl)-2-(1-ethylpiperidin-2-one-3-yl)-2-oxyiminoacetyl, and 2-(2-furyl)-2-(pyrrolidin-2-one-3-yl)oxyiminoacetyl.

When $R_4$ of Formula 1 is $C_1-C_4$ alkyl substituted by phenyl or substituted phenyl, such groups are exemplified by benzyl, 4-hydroxybenzyl, 4-chlorobenzyl, 3-carboxybenzyl, 3-chloro-4-hydroxybenzyl, 2-phenylethyl, 1-phenylethyl, 3-phenylpropyl, 4-hydroxy-2-phenylpropyl, 3-phenylbutyl, and like phenylalkyl groups.

When $R_4$ represents $C_1-C_4$ alkyl substituted by amino or protected amino, examples include 2-aminoethyl, 3-aminopropyl, 4-aminobutyl, 2-aminopropyl and such groups wherein the amino group is protected by an amino-protecting group, e.g., as defined herein for R°.

When $R_4$ is a $C_2-C_4$ alkenyl group, examples include allyl, butene-2, butene-3, butene-1, and like groups.

The 1-carbacephalosporins provided by the invention form salts with suitable bases, in particular, the pharmaceutically acceptable, non-toxic salts. The C-4 carboxy group of the 1-carbacephalosporin can form salts with the alkali and alkaline earth metal hydroxides, carbonates and bicarbonates. Examples of such pharmaceutically acceptable salts are the sodium, potassium, calcium, and magnesium salts. Salts also may be formed with amines such as dibenzylamine, cyclohexylamine, triethylamine, ethanolamine, di-ethanolamine, and like amines. Likewise, when the 1-carbacephalosporin is substituted by two or more carboxy groups, di- and tri-salts are obtained by conventional salt-forming methods.

1-Carbacephalosporin compounds represented by Formula (1) which bear an amino group substituent either in the 7-position side chain or in the 3-position substituent also form salts with suitable acids to provide the antibiotics as pharmaceutically acceptable salts. Examples of suitable acids are hydrochloric, hydrobromic, sulfuric, and phosphoric.

The pharmaceutically acceptable, non-toxic salts are useful forms of the antibiotics for preparing antibiotic formulations.

The biologically labile esters represented by $R_2$ in the Formula (1) are prepared by known method, for example, an acyloxymethyl ester such as the acetoxymethyl ester is obtained by reacting the sodium salt of the 1-carbacephalosporin acid with an acetoxymethyl halide e.g. acetoxymethyl bromide. Alternatively, the halide such as pivaloyloxymethyl iodide is reacted with the free acid in the presence of tertiary amine e.g. N-methylmorpholine or triethylamine to form the ester.

Preferred biologically labile esters are the acetoxymethyl, 1-acetoxyethyl, pivaloyloxymethyl, pivaloyloxyethyl, and the dioxolene-2-one cyclocarbamate.

Examples of the above-defined preferred 1-carbacephalosporins are described below in Table 2 wherein the terms in the column headings refer to Formula (1).

TABLE 2

| R | $R_1$ | $R_2$ | A |
|---|---|---|---|
| phenyl | H | H | $OC_2H_5$ |
| 2,6-dimethoxyphenyl | H | H | $OCH_3$ |
| phenylmethyl | H | H | OH |
| phenylmethyl | H | H | $OC_2H_5$ |
| 2-aminomethylphenylmethyl | H | H | $OC_2H_5$ |
| phenoxymethyl | H | H | o-allyl |
| phenoxymethyl | H | H | OH |
| phenoxymethyl | H | H | $O-C_2H_5$ |
| phenoxymethyl | H | H | o-phenyl |
| phenylthiomethyl | H | H | $CH_3$ |
| 4-chlorophenylthiomethyl | H | H | $OCH_3$ |
| 2-thienylmethyl | $OCH_3$ | H | $NH_2$ |
| 2-thienylmethyl | H | H | 2-pyridyl |
| 2-thienylmethyl | H | H | ![1-methyl-tetrazol-5-ylthiomethyl group] $CH_2-S-$(N-methyltetrazolyl) |
| 2-furylmethyl | H | H | OH |
| 4-pyridylthiomethyl | H | H | $-OCH_3$ |
| α-aminobenzyl | H | H | $-OCH_3$ |
| α-aminobenzyl | H | H | $OC_2H_5$ |
| α-aminobenzyl | H | H | $OC_4H_{9\underline{n}}$ |
| α-aminobenzyl | H | H | $O-CH_2CH_2OCH_3$ |
| α-carboxybenzyl | H | H | $OCH_3$ |
| α-hydroxybenzyl | H | H | $O-C_3H_{7\underline{n}}$ |
| 2-aminothiazol-4-ylmethyl | H | H | OH |
| 2-aminothiazol-4-ylmethyl | H | H | $OCH_3$ |
| 2-aminothiazol-4-ylmethyl | H | H | $-O-CH_2CH_2Cl$ |
| (2-aminothiazol-4-yl) methoxyiminomethyl) | H | H | $-CH_3$ |
| (2-aminothiazol-4-yl) methoxyiminomethyl) | H | H | (4-aminopyridin-2-ylthiomethyl) $-CH_2-S-$ |
| (2-aminothiazol-4-yl) methoxyiminomethyl) | H | H | (1-methyltetrazol-5-ylthiomethyl) $-CH_2-S-$ |
| (2-aminothiazol-4-yl) methoxyiminomethyl) | H | H | (5-methyl-1,3,4-thiadiazol-2-ylmethyl) $-CH_2-\cdots-CH_3$ with S |
| (1H)tetrazolylmethyl- | H | H | (5-methyl-1,3,4-thiadiazol-2-ylmethyl) $-CH_2-\cdots-CH_3$ with S |
| (2-aminothiazol-4-yl) (2-carboxyprop-2-yl) | H | H | $-OC_2H_5$ |

TABLE 2-continued

| R | $R_1$ | $R_2$ | A |
|---|---|---|---|
| oxyiminomethyl- | | | |
| α-amino-1,4-cuclodienylmethyl | H | H | —OCH$_3$ |
| 4-aminopyridin-3-ylmethyl | H | H | —O—benzyl |
| α-sulfoaminobenzyl | H | H | —OCH$_3$ |
| α-sulfoaminothien-2-ylmethyl | H | H | —O—C$_3$H$_7$ |
| 4-aminopyridazin-3-ylmethyl | H | H | OH |
| 4-aminopyridazin-3-ylmethyl | H | H | CH$_3$ |
| (2-aminothiazol-4-yl)(carboxymethoxyimino)methyl | H | (−) | 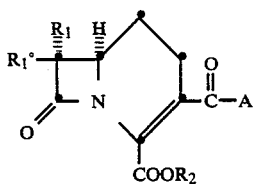 |
| (2-aminothiazol-4-yl)(2-carboxyprop-2-yl)oxyiminomethyl | H | (−) | (pyridinium with CONH$_2$) |
| 2-thienylmethyl | H | H | —C(O)NH$_2$ |
| 2-aminothiazol-4-yl (syn-methoxyimino)methyl | H | H | —C(O)OC$_2$H$_5$ |
| 2-aminothiazol-4-yl (syn-methoxyimino)methyl | H | H | —COOH |
| 2-aminothiazol-4-yl (syn-methoxyimino)methyl | H | H | —C(O)C$_6$H$_5$ |
| phenylmethyl | H | H | —O—(CH$_2$)$_2$—(pyridinium)—N—CH$_3$ Cl$^\ominus$ |
| phenylmethyl | H | H | —NH—(CH$_2$)$_2$—NHC$_6$H$_5$ |
| 2-thienylmethyl | OCH$_3$ | H | —CH$_2$OC(O)NH$_2$ |
| 2-thienylmethyl | OCH$_3$ | H | —CH$_2$CH$_2$OC(O)NH$_2$ |
| 2-thienylmethyl | H | H | —(CH$_2$)$_2$—C(O)C$_2$H$_5$ |
| 4-chlorophenylthiomethyl | H | H | —(CH$_2$)$_3$—S—tetrazole |
| phenylmethyl | H | H | —O—(CH$_2$)$_3$—NH—C(O)—NHCH$_3$ |

In one of its aspects, this invention provides 7β-amino- and 7β-protected amino-1-carbacephalosporin compounds useful as intermediates in the preparation of the antibiotics represented by Formula (1). These intermediates are represented by the following Formula (4).

 (4)

wherein $R_1°$ is amino or a protected amino group $R°$; $R_1$ and A have the same meanings as defined for Formula (1) and $R_2$ is as defined above for Formula (1).

Preferred amino-protecting groups, $R_1°$, are the alkyl, alkenyl, alkynyl, arylalkyl, and cycloalkyloxycarbonyl groups represented by the formula $R_9OC(O)—$ wherein $R_9$ is $C_1$-$C_5$ alkyl, $C_3$-$C_5$ alkenyl, $C_1$-$C_{10}$ alkinyl, $C_4$-$C_7$ cycloalkyl, benzyl or substituted benzyl. Examples of $C_1$-$C_5$ alkoxycarbonyl groups are methoxycarbonyl, ethoxycarbonyl, t-butyloxycarbonyl, t-amyloxycarbonyl, 2,2,2-trichloroethoxycarbonyl, and the like. Examples of alkenyloxycarbonyl groups are allyloxycarbonyl, 1-methylallyloxycarboyl, 1,1-dimethyl allyloxycarbonyl, 2-propenyloxycarbonyl, and the like. Examples of alkynyloxycarbonyl groups are propargyloxycarbonyl, dimethylethynylcarbinyloxycarbonyl, diethylethynylcarbinyloxycarbonyl, 1-ethynylcyclopentyloxycarbonyl, 1-ethynylcyclohexyloxycarbonyl, and the like. $C_4$-$C_7$ Cycloalkoxycarbonyl groups are illustrated by cyclobutyloxycarbonyl, cyclopentyloxycarbonyl, and cyclohexyloxycarbonyl. Benzyloxycarbonyl and substituted benzyloxycarbonyl groups are exemplified by benzyloxycarbonyl (CBz), p-nitrobenzyloxycarbonyl, and p-chlorobenzyloxycarbonyl.

Examples of the 7β-amino and 7β-protected amino-1-carbacephalosporins are:

t-butyl 7-amino-3-methoxycarbonyl-1-carba(1-dethia)-3-cephem-4-carboxylate, p-methoxybenzyl 7-amino-3-ethoxycarbonyl-1-carba(1-dethia)-3-cephem-4-carboxylate, allyl 7-amino-3-acetyl-1-carba(1-dethia)-3-cephem-4-carboxylate, di-(trimethylsilyl) 7-amino-1-carba(1-dethia)-3-cephem-3,4-dicarboxylate, 7-amino-1-carba(1-dethia)-3-cephem-3,4-dicarboxylic acid, t-butyl 7-amino-1-carba(1-dethia)-3-carbamoyl-3-cephem-4-carboxylate,
benzyl 7-amino-3-acetoxymethylcarbonyl-1-carba(1-dethia)-3-cephem-4-carboxylate,
t-butyl 7-t-butyloxycarbonylamino-3-methoxycarbonyl-1-carba(1-dethia)-3-cephem-4-carboxylate,
diphenylmethyl 7-benzyloxycarbonylamino-3-n-propoxycarbonyl-1-carba(1-dethia)-3-cephem-4-carboxylate,
allyl 7-allyloxycarbonylamino-3-pivaloyl-1-carba(1-dethia)-3-cephem-4-carboxylate,
p-methoxybenzyl 7-p-nitrobenzyloxycarbonylamino-3-(N,N-dimethylaminocarbonyl)-1-carba(1-dethia)-3-cephem-4-carboxylate,
t-butyl 7$\beta$-t-butyloxycarbonylamino-7$\alpha$-methoxy-3-methoxycarbonyl-1-carba(1-dethia)-3-cephem-4-carboxylate, and
t-butyl 7$\beta$-benzyloxycarbonylamino-3-benzyloxycarbonyl-3-cephem-1-carba(1-dethia)-3-cephem-4-carboxylate.

The 7$\beta$-amino-1-carba-3-cephem compounds (Formula 4, $R_1° = NH_2$) are N-acylated with a carboxylic acid RCOOH or a reactive derivative thereof to provide a compound of Formula (1). The N-acylation can be carried out by employing the general acylation methods used for the N-acylation of the cephalosporin nucleii e.g., 7ACA and 7ADCA. For example, the nucleus (4) is coupled with the acid RCOOH in the presence of a dehydrating agent such as a carbodiimide e.g., dicyclohexylcarbodiimide. Alternatively the carboxylic acid can be converted to a reactive derivative of the carboxy group and the reactive derivative used in the N-acylation. Reactive derivatives of the carboxy group that can be used are the acid halides, acid azides, acid anhydrides, an active ester such as those formed with ethyl chloroformate and isobutyl chloroformate; phenylcarbamates; N-hydroxyimides such as formed with N-hydroxysuccinimide and N-hydroxyphthalimide; and those formed with hydroxybenztriazole (HBT); and like active carboxy derivatives. During the N-acylation any free amino or carboxy groups present in the carboxylic acid RCOOH are desirably protected.

Preferred 1-carbacephalosporins are represented by Formula (1) wherein A is hydroxy, $C_1$-$C_6$ alkoxy, $C_2$-$C_6$ alkenyloxy, $C_2$-$C_6$ alkynyloxy, or substituted $C_1$-$C_6$ alkoxy. A further group is represented when A is $C_1$-$C_4$ alkyl or substituted $C_1$-$C_4$ alkyl. Another group of the compounds represented by Formula (1) are the 3-amido or 3-substituted amido compounds wherein A is an amino group represented by —N(R')(R'') as defined hereinabove.

A further preferred group of 1-carbacephalosporins are represented by Formula (1) when A is —C(O)R$_6$ as defined above. Examples of such preferred groups are ethoxycarbonyl, carboxy, carbamoyl, N-methylcarbamoyl, and N,N-dimethylcarbamoyl.

Further preferred compounds of the invention are represented by Formula (1) wherein R is the substituted methyl group

In particular compounds wherein Q is amino or substituted amino. Especially preferred compounds are represented when Q is amino. Examples of such 1-carbacephems are 7$\beta$-(D-phenylglycylamino)-3-methoxycarbonyl-3-cephem-1-carba(1-dethia)-4-carboxylic acid, 7$\beta$-(D-4-hydroxyphenylglycylamino)-3-ethoxycarbonyl-3-cephem-1-carba(1-dethia)-4-carboxylic acid, 7$\beta$-(D-3-hydroxyphenylglycylamino)-3-acetyl-3-cephem-1-carba(1-dethia)-4-carboxylic acid, 7$\beta$-(D-2-thienylglycylamino)-3-methoxycarbonyl-3-cephem-1-carba(1-dethia)-4-carboxic acid, 7$\beta$-(D-benzothien-3-ylglycylamino)-3-methoxycarbonyl-3-cephem-1-carba(1-dethia)-4-carboxylic acid, and like 1-carba(1-dethia) compounds.

A further preferred group is represented by Formula (1) wherein R is the group

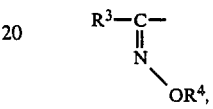

in the syn form.

Particularly preferred compounds are represented when $R^4$ is $C_1$-$C_4$ alkyl or a carboxy substituted alkyl group such as carboxymethyl, 2-carboxyethyl, 3-carboxypropyl, 2-carboxy-2-propyl or a $C_1$-$C_4$ alkyl substituted with amino such as 2-aminoethyl; and $R^3$ is a five or six membered heterocyclic ring $R^1$, in particular, an amino substituted heterocyclic. Especially preferred heterocyclics are the 2-aminothiazole or 2-aminooxazole ring. Examples of such preferred compounds are 7$\beta$-[2-(2-aminothiazol-4-yl)-2-methoxyiminoacetamido]-3-methoxycarbonyl-3-cephem-1-carba(1-dethia)-4-carboxylic acid, and the corresponding 7$\beta$-substituted 3-acetyl, 3-ethoxycarbonyl, and 3-carboxy substituted 1-carba(1-dethia)-3-cephem compounds.

Further preferred compounds of this group are represented by the formula

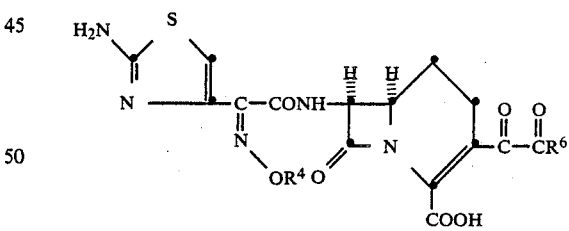

and the pharmaceutically acceptable non-toxic salts thereof. Preferred of the structure are represented when $R_6$ is hydroxy, $C_1$-$C_4$ alkoxy, e.g. ethoxy, amino, or methylamino, and $R^4$ is $C_1$-$C_4$ alkyl or a carboxy-substituted alkyl group as defined above.

The 1-carbacephalosporins provided herein inhibit the growth of microorganisms pathogenic to man and animals. The compounds are broad spectrum antibiotics which are particularly effective against gram-positive bacteria. The following Table 3 lists the minimum inhibitory concentrations (mic) of preferred compounds vs. representative infectious bacteria. The inhibitory concentrations were obtained in standard in vitro tests carried out by the agar dilution method.

TABLE 3

Antibacterial Activity of 3-C(O)A 1-carba (1-dethia)-3-cephem-4-carboxylic acids

| Organism[1] | Test Compounds[2] | | | | | | |
|---|---|---|---|---|---|---|---|
| | 1 | 2 | 3 | 4 | 5 | 6 | 7 |
| *Staphylococcus aureus* X1.1 | 4 | 2 | 2 | 2 | 4 | 4 | 2 |
| *Staphylococcus epidermidis* 222 | 4 | 4 | 1 | 4 | 4 | 4 | 2 |
| *Streptococcus pyogenes* C203 | .125 | — | .03 | .125 | .125 | .015 | .015 |
| *Escherichia coli* EC14 | 1 | 4 | 2 | 4 | .5 | .03 | .015 |
| Klebsiella X26 | .5 | .5 | .125 | .125 | .125 | .008 | .008 |
| Salmonella X514 | .5 | 8 | 2 | 8 | .5 | .03 | .008 |
| *Proteus morganii* PR15 | 128 | 32 | 32 | 64 | 32 | 1 | .03 |
| *Enterobacter aerogenes* C32 | 128 | 32 | 8 | 16 | 4 | .125 | .25 |

[1]Numbers and letters are strain designations

[2]Test Compound No. 1 = 7β-(D-phenylglycylamino)-3-methoxycarbonyl-3-cephem-1-carba(1-dethia)-4-carboxylic acid Test Compound No. 2 = 7β-(D-phenylglycylamino)-3-benzyloxycarbonyl-3-cephem-1-carba(1-dethia)-4-carboxylic acid Test Compound No. 3 = 7β-(D-phenylglycylamino)-3-n-butyloxycarbonyl-3-cephem-1-carba(1-dethia)-4-carboxylic acid Test Compound No. 4 = 7β-(D-benzothien-3-ylglycylamino)-3-methoxycarbonyl-3-cephem-1-carba(1-dethia)-4-carboxylic acid Test Compound No. 5 = 7β-(D-phenylglycylamino)-3-ethoxycarbonyl-3-cephem-1-carba(1-dethia)-4-carboxylic acid Test Compound No. 6 = 7β-[2-(2-aminothiazol-4-yl)-syn-2-methoxyiminoacetamido]-3-methoxycarbonyl-3-cephem-1-carba(1-dethia)-4-carboxylic acid Test Compound No. 7 = 7β-[2-(2-aminothiazol-4-yl)-syn-methoxyiminoacetamido]-3-acetyl-3-cephem-1-carba(1-dethia)-4-carboxylic acid This invention also provides a method for treating infectious diseases in man and other animals and pharmaceutical formulations suitable for administration in the treatment method. The therapeutic method of this invention comprises administering to a man or animal an antibiotically effective non-toxic dose of a compound represented by Formula (1) wherein $R_2$ is hydrogen or a pharmaceutically acceptable salt or biologically labile ester thereof.

An antibiotically effective amount is an amount between about 25 mg and about 2 grams. The compound, salt or ester may be administered in a single dose or in multiple doses throughout the day. Treatment may continue for a week to ten days or longer depending upon the duration of the infection. The particular dose and regimen can depend on such factors as the weight and age of the patient, the particular causative organism, the severity of the infection, the general health of the patient, and the tolerance of the individual to the antibiotic.

The 1-carbacephalosporins may be administered parenterally, orally, subcutaneously or rectally. As with other β-lactam antibiotics the method of this invention may be used prophylactically to prevent infections after exposure or before possible exposure e.g., preoperatively. The antibiotic 1-carbacephalosporins may be administered by conventional methods e.g., in capsules, tablets, by syringe, or by intravenous drip.

The pharmaceutical formulations of the invention comprise an antibiotically effective non-toxic amount of a 1-carbacephalosporin represented by the Formula (1) wherein $R_2$ is hydrogen, a pharmaceutically acceptable non-toxic salt or biologically labile ester thereof, and a pharmaceutical carrier.

Formulations for oral administration include capsules, tablets, lozenges, and liquid suspensions. The antibiotic or a salt or ester thereof in the form of a dry powder is encapsulated in gelatin capsules for oral use. The antibiotic may also be blended with an excipient e.g., a stabilizer prior to filling. Capsules may contain between about 100 mg and about 500 mg to provide unit dosage formulations.

Tablets containing between about 100 mg and 500 mg of the antibiotic or a salt or ester thereof are formulated by conventional means and may contain in addition a binding agent, disintegrating agent, stabilizing agent, antioxidant, etc.

Liquid preparations of the antibiotic may be prepared for infant and geriatric use. Pediatric suspensions are formulated with the antibiotic oral excipients such as suspending agents, flavoring agents, stabilizers and the like. Solutions of the antibiotics likewise may be formulated with solubilizing agents, flavoring agents, sugar, water, etc.

Parenteral formulations of the antibiotics for injection are formulated with Water-for-Injection, Ringer's solution, physiological saline, or glucose solution. The antibiotic also may be administered in an intravenous fluid by the drip method.

For parenteral use the antibiotic, a salt or biologically labile ester thereof, is made up preferably in dry crystalline powder form or as a lyophilized powder and filled into vials. Such vials contain between about 100 mg and about 2 grams of antibiotic for vial.

In a further aspect of this invention, there is provided a process for preparing a compound of Formula (1) which comprises:

(A) acylating a compound of the formula

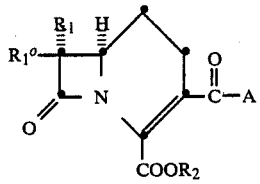

wherein $R^0$ is amino; or (B) alkoxylating a compound of Formula (1), wherein $R_1$ is H; or (C) esterifying a compound of Formula (1), wherein $R_2$ is H; or (D) deesterifying a compound of Formula (1), wherein $R_2$ is not H; or (E) reacting a compound of Formula (1), wherein A is —$CH_2I$ or —$CH_2Br$, with a compound of the formula $HSR_3$ in the presence of a base, or with an alkali metal salt of a compound of formula M³⁰ SR₃, wherein M⁺ is an alkali metal cation; or with a compound of formula R₄; or (F) removing any amino-protecting groups; or (G) reacting a compound of Formula (1), wherein A is

with a compound of formula R₄; wherein R, R⁰, R₁, R₂, and A are as defined above.

In a further aspect of this invention, there is provided a process for preparing a compound of Formula (2),

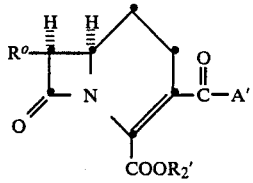

which comprises:
reacting a compound of Formula (AA):

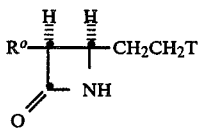

with a compound of Formula (BB):

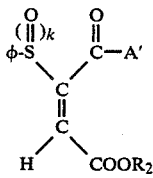

in the presence of a non-nucleophilic base, wherein k is 1 or 2 and T is a suitable leaving group.

In a further aspect of this invention there is provided a process for preparing a 1-carbacephalosporin represented by Formula (1) wherein R₂ is a carboxy protecting group and R₁ is hydrogen which comprises (1) mixing in an inert aprotic solvent at a temperature between about −90° C. and about −45° C. a 3-protected amino-4-(2-substituted-ethyl)azetidin-2-one represented by Formula (AA):

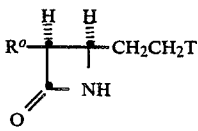

wherein R⁰ is protected amino group, an T is as defined hereinabove, with a substituted acrylic acid ester represented by Formula (BB):

wherein φ is phenyl, k is 1 or 2, R₂' is a carboxy protecting group; and A' has the same meanings as defined for Formula (BB) hereinabove; in the presence of a non-nucleophilic base in an amount about eqimolar with the azetidinone; (2) removing the amino-protecting group to provide the 3β-amino-1-carbacephalosporin represented by the formula

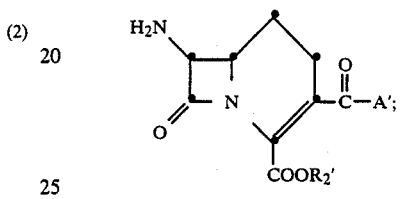

and (3) N-acylating the 3β-amino-1-carbacephalosporin with the carboxylic acid RCOOH or a reactive derivative thereof.

A preferred non-nucleophilic base is a bis(trialkylsilyl)lithium amide e.g., bis(trimethylsilyl)lithium amide. Preferred solvents are tetrahydrofuran and 1,2-dimethoxyethane.

The 1-carbacephalosporin is recovered from the reaction mixture and is purified by conventional extraction and chromatographic methods.

In preferred embodiments of the process A' is C₁-C₄ alkoxy or C₁-C₄ alkyl, and k−1. A preferred protected amino group R⁰ is t-butyloxycarbonylamino and T is preferably iodo.

In an embodiment of the process 3β-(t-butyloxycarbonylamino)-4β-(2-iodoethyl)azetidin-2-one is reacted with allyl 3-phenylsulfinyl-3-methoxycarbonylacrylate (Formula (BB), A'=—OCH₃, k=1, R₂'=allyl) to provide allyl 3β-(t-butyloxycarbonylamino)-3-methoxycarbonyl-1-carba(1-dethia)-3-cephem-4-carboxylate. The latter is deprotected with trifluoroacetic acid and the 3β-amino-1-carba-3-cephem ester is acylated with 2-(t-butyloxycarbonylamino)-2-phenylacetyl chloride to yield allyl 7β-(2-t-butyloxycarbonylamino)-2-phenylacetylamino)-3-methoxycarbonyl-1-carba(1-dethia)-3-cephem-4-carboxylate. The amino-protecting t-BOC group of the latter is removed on treatment of the acylation product with 98% formic acid to provide allyl 7β-(2-amino-2-phenylacetylamino-3-methoxycarbonyl-1-carba(1-dethia)-3-cephem-4-carboxylate (Formula (1), R=α-aminobenzyl, R₁=H, A=—OCH₃, and R₂=allyl). Removal of the allyl ester group by known methods provides the corresponding antibiotic compound as the free carboxylic acid (R₂=H).

The following Examples further describe the compounds of the invention and the process for the preparation thereof.

In the Examples the following abbreviations have the indicated meanings: BSTFA=bis(trimethylsilyl)trifluoroacetamide; DBU=1,8-Diazabicyclo[5.4.0]-undec-7-ene; DMF=dimethylformamide; HPLC=high performance liquid chromatography;

t-BOC=t-butyloxycarbonyl; THF=tetrahydrofuran; and J=coupling constant for NMR spectra in Hz.

PREPARATION OF SUBSTITUTED ACRYLIC ACID ESTERS

Preparation 1

1-Methyl 4-t-butyl 2-phenylsulfinylmaleic acid diester

To a 2-liter, flame-dried flask flushed with nitrogen and equipped with a dropping funnel and stirrer containing bis(trimethylsilyl)lithiumamide (254.23 mmole) in 200 ml of THF and cooled to −42° C. was added a solution of methyl phenylmercaptoacetate (43.33 g, 254.23 mmole) in 100 ml of THF. The solution was stirred in the cold for about 25 minutes and was transferred via cannula over 30 minutes to another flask containing t-butyl bromoacetate (51.08 g, 261.86 mmole) in 100 ml of THF also cooled to −42° C. The reaction mixture was stirred over 2.5 hours while the flask was allowed to warm to room temperature. The reaction mixture was poured into 800 ml of a saturated solution of ammonium chloride in water and 1200 ml of ethyl acetate were added. The organic layer was separated and the aqueous layer was extracted once with 300 ml of ethyl acetate. The extract was combined with the organic layer, dried over magnesium sulfate, filtered and evaporated under vacuum to yield 80 g of the crude product as a brownish oil. The crude product was purified via preparative HPLC to yield 60 g (79.7% yield) of the product, 1-methyl 4-t-butyl 2-phenylthiosuccinic acid diester.

90 MHz NMR (CDCl$_3$, δ): 1.4 (s, 9H, t-butyl ester H), 2.9–3.0 (m, 2H, CH$_2$ H), 3.7 (s, 3H, COOCH$_3$), 3.9 (dd, J=7 and 9, 1H, methine H), 7.5–7.2 (m, 5H, phenyl H).

The mixed diester phenylsulfide product obtained above (60 g, 202.43 mmole) was dissolved in a mixture of 1000 ml of carbon tetrachloride, 500 ml of THF and N-chlorosuccinimide (28.38 g, 212.55 mmole) and the mixture was heated at the reflux temperature for about 4 hours. The thin layer chromatogram run with a small portion of the reaction mixture showed one major spot and no starting material. The mixture was evaporated under vacuum and the residue was treated with hexane. The insoluble material was filtered, washed with hexane, the hexane wash combined with the hexane filtrate evaporated under vacuum to yield 67 g of 1-methyl 4-t-butyl 2-chloro-2-phenylthiosuccinic acid diester as an orange oil.

The chloro diester obtained above (67 g, 202.51 mmole) was dissolved in 1 liter of methylene chloride and the solution cooled to −78° C. DBU (31.44 g, 206.56 mmole) was added to this cold solution via syringe and the solution turned dark and thickened. The reaction mixture was allowed to warm to room temperature over 1.5 hours when a thin layer chromatogram of the reaction mixture showed two major spots and no starting material. The mixture was poured into 1 liter of water containing 200 ml of 1N hydrochloric acid and the organic layer separated. The organic layer was again poured into aqueous HCl as before, the organic phase separated, dried over magnesium sulfate, filtered and evaporated under vacuum to yield 60 g of the product as a brownish, oily solid. The crude product was purified via preparative HPLC to yield 47.7 g of 1-methyl 4-t-butyl 2-phenylthiomaleic acid diester as a light yellow oil which solidified upon standing in the refrigerator overnight.

90 MHz NMR (CDCl$_3$, δ): 1.4 and 1.5 (s, 9H, t-butyl H), 3.3 and 3.6 (s, 3H, COOCH$_3$), 5.4 and 6.3 (s, 1H, vinyl H), and 7.2–7.6 (m, 5H, phenyl H).

To a solution of the maleic acid diester obtained above (2.32 g, 7.95 mmole) in 75 ml of methylene chloride and cooled to −42° C. was added peracetic acid (1.67 ml, 8.745 mmole) and the mixture was allowed to warm to room temperature. The reaction mixture was stirred at room temperature for about one hour and 1.95 g of dimethyl sulfide was added. The mixture was stirred for 30 minutes after addition of the sulfide and was then poured onto a pad of silica gel (150 g). The pad was washed with methylene chloride until all remaining starting material had filtered. The pad was then flushed with diethyl ether until the desired product had filtered. The ether solution of the product was evaporated to yield the product as a yellow oil. The oil was treated three times with 200 ml-portions of toluene, and after each treatment was evaporated under vacuum. There were obtained 1.95 g (79% yield) of the 2-phenylsulfinyl maleic acid diester as a yellow oil.

90 MHz NMR (CDCl$_3$, δ): 1.5 and 1.6 (s, 9H, t-butyl), 3.6 and 3.7 (s, 3H, COOCH$_3$), 6.9 and 7.2 (s, 1H, vinyl H), 7.1 and 7.7 (m, 5H, phenyl H).

Preparation 2

1-Methyl 4-allyl 2-phenylsulfinyl maleic acid diester

The methyl t-butyl phenylsulfinyl maleic acid mixed diester obtained as described by Preparation 1 was treated with 8 ml of trifluoroacetic acid at 0° C. to effect selective removal of the t-butyl ester group. After 5 minutes, the reaction mixture was allowed to stir for 2 hours at room temperature and was then evaporated under vacuum at 45° C. to yield an oil. The oil was dissolved in the minimum amount of methylene chloride and the solution was diluted with hexane until cloudy. The product precipitated as a white solid. The mother liquor was decanted from the solid product which was washed with a mixture of 20% methylene chloride/hexane. The washings were added to the mother liquor and placed in the refrigerator overnight to obtain a second crop of product. There were obtained 2.124 g of first crop product and a second crop of 900 mg (79.6% yield) as dried under vacuum.

The phenylsulfinyl half ester obtained as described above (2.124 g, 8.362 mmole) was dissolved in 8 ml of DMF and the solution cooled to 0° C. First, allyl bromide (1.011 g, 8.362 mmole) was added to the solution followed by triethylamine (1.25 ml, 9.0 mmole) and the mixture was allowed to warm to room temperature. The reaction mixture was stirred at room temperature for 2.5 hours, a thin layer chromatogram of a small portion of the reaction mixture indicated that most of the starting material had reacted, and showed a new major spot. The very dark reaction mixture was poured into a mixture of 60 ml of diethyl ether and 50 ml of water. The aqueous layer was separated and washed with 40 ml of diethyl ether. The ether layers were combined and washed sequentially twice with 50 ml-portions of a saturated aqueous sodium bicarbonate solution, twice with 50 ml-portions of 1N hydrochloric acid and once with 50 ml of brine. The washed organic layer was dried over magnesium sulfate, filtered and evaporated under vacuum to yield the product as a yellow oil. The product was taken up in 50 ml of toluene and evaporated under vacuum. The process was repeated to yield 1.934 g (78.6% yield) of the title compound, the allyl methyl diester.

90 MHz NMR (CDCl$_3$, δ): 3.6 (s, 3H, COOCH$_3$), 4.7 (dm, J=6, 2H, allyl CH$_2$), 5.2-5.5 (m, 2H, allyl

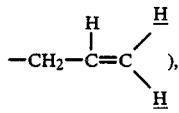

5.7-6.2 (m, 1H, allyl

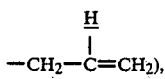

7.4-7.7 (m, 5H, phenyl H).

Preparation 3

1-Ethyl 4-allyl 2-phenylsulfinyl maleic acid diester

To a solution of 1-methyl 4-t-butyl 2-phenylthio maleic acid diester (5 g, 16.99 mmole) in 100 ml of THF was added lithium hydroxide (16.99 mmole) and the mixture was stirred for 3 hours at room temperature. The reaction mixture was poured into a mixture of 150 ml of water and 300 ml of diethyl ether, and the aqueous and organic layers were separated. The aqueous layer was washed twice with 150 ml-portions of diethyl ether and the ether wash was combined with the organic layer and evaporated to yield 2.2 g of the starting material, the diester. The aqueous layer was acidified with 17 ml of 1N hydrochloric acid and extracted twice with 200 ml-portions of diethyl ether. The extracts were combined, dried over magnesium sulfate, filtered and evaporated in vacuum to yield 2.7 g of the mono t-butylester, 4-t-butyl 2-phenylthiomaleic acid mono ester, as a yellow oil (57%).

To a solution of the phenylthio half ester obtained as as described above (8.0 g, 28.551 mmole) in DMF was added via pipette ethyl iodide (4.9 g, 31.406 mmole) and triethylamine (4.78 ml, 34.261 mmole) and the mixture was stirred for one hour at room temperature. The reaction mixture was then heated briefly to a temperature of 65° C. and after cooling, an additional 2.0 ml of ethyl iodide in 4.0 ml of triethylamine were added. The mixture was again heated briefly to a temperature of about 65° C. and was cooled. The reaction mixture was poured into a mixture of 200 ml of diethyl ether in 120 ml of water. The organic layer was separated from the organic layer which was washed twice with 100 ml-portions of a saturated aqueous solution of sodium bicarbonate, twice with 100 ml of 1N hydrochloric acid and once with 100 ml of brine. The organic layer was then dried over magnesium sulfate, filtered and evaporated under vacuum to yield 6.51 g of the phenylthio ethyl t-butyl diester as an oil (74% yield).

90 MHz NMR (CDCl$_3$, δ): 0.9 and 1.1 (t, J=7, 3H, CO$_2$CH$_2$CH$_3$), 1.4 and 1.5 (s, 9H, t-butyl), 3.7 and 4.1 (q, J=7, 2H, —CO$_2$CH$_2$CH$_3$), 5.4 and 6.2 (s, 1H, vinyl H), and 7.2 to 7.6 (m, 5H, phenyl H).

The t-butyl ethyl diester, 6.51 g, was treated at room temperature for 30 minutes with 9 ml of trifluoroacetic acid to effect select deesterification of the t-butyl ester group and provide 5.1 g of 1-ethyl 2-phenylthiomaleic acid monoethyl ester as a yellow oil.

90 MHz NMR (CDCl$_3$, δ): 0.9 and 1.2 (t, J=7, 3H, CO$_2$CH$_2$CH$_3$), 3.7 and 4.1 (q, J=7, 2H, CO$_2$CH$_2$CH$_3$), 5.4 and 6.2 (s, 1H, vinyl H), 7.1-7.6 (m, 5H, phenyl H), and 8.7 (broad s, 1H, COOH).

The half acid ester obtained as described above (5.1 g, 20.222 mmole) was dissolved in 22 ml of DMF and allyl bromide (3.67 g, 30.333 mmole) was added to the solution followed by triethylamine (4.8 ml, 34.38 mmole) and the reaction mixture was allowed to stir for approximately 16 hours. The mixture was poured into a mixture of 100 ml of water and 200 ml of diethyl ether and the organic layer separated from the aqueous layer. The organic layer was washed twice with 100 ml-portions of a saturated aqueous sodium bicarbonate solution, twice with 100 ml-portions of 1N hydrochloric acid and once with 100 ml of brine. The washed layer was then dried over magnesium sulfate, filtered and evaporated under vacuum to yield 5.5 g (93.2% yield) of 1-ethyl 4-allyl 2-phenylthiomaleic acid diester as a yellow oil.

90 MHz NMR (CDCl$_3$, δ): 0.9 and 1.2 (t, J=7, 3H, —CH$_2$CH$_3$), 3.8 and 4.1 (q, J=7, 2H, —CH$_2$CH$_3$), 4.5 and 4.6 (dm, J=5, 2H, —CH$_2$—CH=CH$_2$), 5.1-5.4 (m, 2H, —CH$_2$—CH=CH$_2$), 5.5 and 6.3 (s, 1H,

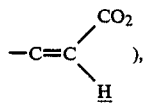

5.6-6.2 (m, 1H, —CH$_2$—CH=CH$_2$), and 7.2-7.6 (m, 5H, phenyl).

The allyl ethyl diester (5.52 g, 18.891 mmole) prepared as described above was dissolved in methylene chloride and the solution cooled to a temperature of about −42° C. To the cold solution was added peracetic acid (5.04 ml, 26.447 mmole) and the mixture was allowed to stir for about 2.5 hours at room temperature. An additional 2.0 ml of peracetic acid was added and the mixture was stirred at room temperature for an additional 1.5 hours. Dimethylsulfide (4.85 ml, 66 mmole) was then added to the mixture which was stirred for an additional 45 minutes. The unreacted starting material was separated by pouring the reaction mixture directly onto 125 g of silica gel and washing the starting material from the silica with methylene chloride. The silica gel was then eluted with diethyl ether until all of the desired sulfoxide had been washed free. The product containing filtrate was concentrated under vacuum to provide the sulfoxide diester as a yellow oil. The oil was dissolved successively six times in 100 ml-portions of toluene and the evaporated to remove toluene to provide 3.8 g of the sulfoxide diester as an oil (80% yield).

90 MHz NMR (CDCl$_3$, δ): 1.1 and 1.2 (t, J=7, 3H, —CH$_2$CH$_3$), 4.0 and 4.1 (q, J=7, 2H, —CH$_2$CH$_3$), 4.65 and 4.75 (dm, J=5, 2H, —CH$_2$—CH=CH$_2$), 5.1-5.5 (m, 2H, —CH$_2$—CH=CH$_2$), 5.7-6.2 (m, 1H, —CH$_2$—CH=CH$_2$), 6.9 and 7.1 (s, 1H, C=CHCOO), and 7.3-7.9 (m, 5H, phenyl).

Preparations 4 to 11

In procedures analogous to preparation 3, the 4-t-butyl 2-phenylthiomaleic acid ester was alkylated with a compound of formula R$_2$'I and then oxidized as in preparation 3 to yield compounds of the formula:

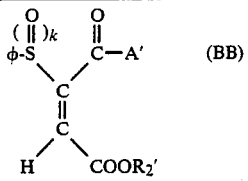

| Preparation | k | A' | $R_2'$ | Spectral |
|---|---|---|---|---|
| 4 | 1 | —OCH₂—CH=CH₂ | —CH₂CH=CH₂ | 90 MHz NMR (CDCl₃, δ): 4.6 (m, 4H, —OCH²—) 5.0 to 5.6 (m, 4H), 5.8 (m, 2H), 6.8 and 7.2 (s, 1H, vinyl H) 7.3 to 7.9 (m, 5H). |
| 5 | 1 | —O—CH₂—⌬ | " | 90 MHz NMR (CDCl₃, δ): 4.8 (dm, J = 7Hz, 2H, —OC$\underline{H}_2$CH), 5.1 (s, 2H, —OCH₂φ), 6.9 (m, 1H), 7.2 (s, 1H, vinyl H). |
| 6 | 1 | —OCH₂—CH₂—CH₂—CH₃ | " | 90 MHz NMR (CDCl₃, δ): 0.9 (m, 3H, CH₃), 1.1 to 1.7 (m, 4H, CH₂CH₂), 4.0 and 4.1 (t, J = 7Hz, 2H, —OC$\underline{H}_2$CH₂), 4.7 and 4.8 (dm, J = 5Hz, 2H, —OC$\underline{H}_2$CH), 7.0 and 7.2 (s, 1H, vinyl H). |
| 7 | 1 | —OCH₂—CH=CH₂ | —C(CH₃)₃ | 90 MHz NMR (CDCl₃, δ): 1.5 and 1.6 (s, 9H, t-butyl), 4.45 and 4.55 (dm, J = 6Hz, 2H, —OC$\underline{H}_2$CH), 6.9 and 7.1 (s, 1H, vinyl H), 7.4 and 7.8 (m, 5H, C₆$\underline{H}_5$). |
| 8 | 1 | —O—⌬ | —CH₂CH=CH₂ | 90 MHz NMR (CDCl₃, δ): 1.2–2.3 (m, 10H), 4.6–4.9 (m, 3H, —OC$\underline{H}_2$CH and O—C$\underline{H}$), 7.0 and 7.2 (s, 1H, vinyl H), 7.4–8.0 (m, 5H, C₆$\underline{H}_5$). |
| 9 | 1 | —OCH₂CH₂CH₂CH₂CH₂CH₃ | —CH₂CH=CH₂ | 90 NHz NMR (CDCl₃, δ): 1.0 (t, J = 5, 3H, —CH₃), 1.0–1.8 (m, 8H, —(CH₂)₄—), 4.1 and 4.2 (t, J = 7, 2H, —OC$\underline{H}_2$CH₂—), 4.75 and 4.85 (m, 2H, —OC$\underline{H}_2$CH), 7.0 and 7.2 (s, 1H, vinyl H). |
| 10 | 1 | —O—CH₂CH₂—Si(CH₃)₃ | " | 90 MHz NMR (CDCl₃, δ): 0.05 and 0.10 (s, 9H, —CH₃), 1.0 (m, 2H, —C$\underline{H}_2$Si), 4.2 (m, 2H, —C$\underline{H}_2$CH₂), 4.75 and 4.85 (dm, J = 6Hz, 2H, —OC$\underline{H}_2$CH), 7.0 and 7.2 (s, 1H, vinyl H). |
| 11 | 1 | —O—CH₂—⌬—NO₂ | " | 90 MHz NMR (CDCl₃, δ): 4.6 and 4.8 (dm, J = 6Hz, 2H, —OC$\underline{H}^2$CH), 7.0 and 7.2 (s, 1H, vinyl H). |

Preparation 12 t-Butyl 3-phenylsulfinyl-4-oxopent-2-enoate

To a solution of 1-phenylthiopropane-2-one (phenylthio acetone) (43.32 g, 260.6 mmole) in 400 ml of THF was added sodium hydride (10.424 g, 260.6 mmole, as a 60% dispersion in mineral oil) and the mixture was stirred for about 15 minutes at room temperature. Next was added t-butyl bromoacetate (52.783 g, 270.6 mmole) over 20 minutes and the reaction mixture was allowed to stir for about 2 hours. A thin layer chromatogram of the reaction mixture showed one major spot and two minor spots. The reaction mixture was poured into a mixture of 1,000 ml of chloroform and 800 ml of a saturated aqueous ammonium chloride solution. The layers were separated and the aqueous layer washed once with 500 ml of chloroform. The chloroform wash was combined with the organic layer and dried over magnesium sulfate, filtered and evaporated under vacuum to provide the product as a yellow oil. The product crystallized upon the addition of 300 ml of hexane. The product was filtered and washed with pentane. There were obtained 41.4 g of the product as white crystals (57% yield).

90 MHz NMR (CDCl₃, δ): 1.4 (s, 9H, t-butyl), 2.4 (s, 3H, —COC$\underline{H}_3$), 2.7 (dd, J—18 and 5, 1H,

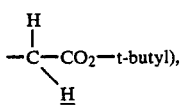

2.9 (dd, J=18 and 9, 1H,

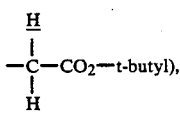

4.0 (dd, J=5 and 9, 1H, —C$\underline{H}$—COCH₃), and 7.2–7.4 (m, 5H, phenyl).

To a solution of the keto t-butyl ester prepared as described above (41.5 g, 147.5 mmole) in 250 ml of THF and 500 ml of carbon tetrachloride was added n-chlorosuccinimide (20.72 g, 155.136 mmole) and the mixture was heated at the reflux temperature for about 2.5 hours. The reaction mixture was evaporated under vacuum to yield an oily solid. Hexane was added to the mixture and the solid (succinimide) was filtered. The filtrate was evaporated under vacuum to yield 46.5 g of t-butyl 3-phenylthio-3-chloro-4-oxopentanoate as a yellow oil.

90 MHz NMR (CDCl$_3$, δ): 1.4 (s, 9H, t-butyl), 2.4 (s, 3H, —COCH$_3$), 3.2 (AB, J=16, 2H, —CH$_2$—CO$_2$—t—butyl), and 7.3-7.6 (m, 5H, phenyl).

The chloroketo ester prepared as described above (46.5 g, 147.75 mmole) was dissolved in 250 ml of methylene chloride and the solution cooled to a temperature of about −78° C. DBU (22.84 g, 150.71 mmole) was added to the cold mixture via a syringe and the mixture was allowed to warm to room temperature over about 2 hours. The dark reaction mixture was poured into a solution of 500 ml of water containing 100 ml of 1N hydrochloric acid. The layers were separated and the organic layer was washed again with the dilute hydrochloric acid. The organic layer was separated, dried over magnesium sulfate, filtered and evaporated under vacuum to yield 42 g of crude product. The product was purified via preparative HPLC to yield 32.86 g (80% yield) of t-butyl 3-phenylthio-4-oxopent-2-eneoate as a yellow crystalline solid.

90 MHz NMR (CDCl$_3$): 1.4 and 1.5 (s, 9H, t-butyl), 2.0 and 2.4 (s, 3H, —COCH$_3$), 5.3-6.1 (s, 1H, vinyl H), and 7.2-7.6 (m, 5H, phenyl).

The t-butyl oxopentenoate prepared as described above was oxidized with peracetic acid in methylene chloride at 42° C. to provide 3.43 g (50.6% yield) of the title compound, t-butyl 3-phenylsulfinyl-4-oxopent-2-eneoate as a yellow oil.

The NMR spectrum of the product indicated that it was a mixture of the cis and trans isomers.

90 MHz NMR (CDCl$_3$, δ): Isomer I: 1.3 (s, 9H, t-butyl), 2.4 (s, 3H, —COOH$_3$), 7.2 (s, 1H, vinyl H), and 7.4-7.8 (m, 5H, phenyl).

Isomer II: 1.5 (s, 9H, t-butyl), 1.9 (s, 3H, —COCH$_3$), 6.6 (s, 1H, vinyl H), and 7.7-7.9 (m, 5H, phenyl).

Preparation 13 allyl 3-phenylsulfinyl-4-oxopentanoate

300 MHz (CDCl$_3$, δ): 1.95 (s, 3H, —CH$_3$), 4.7 (d, J=7, 2H, —OCH$_2$CH), 5.3 (d, J=13, 1H), 5.4 (d, J=18, 1H), 5.95 (m, 1H), 6.7 (s, 1H), 7.5-7.8 (m, 5H, C$_6$H$_5$).

A procedure analogous to Preparation 12 in which allyl bromoacetate was substituted for t-butyl bromoacetate yielded the title compound.

EXAMPLE 1 t-Butyl 7β-t-butyloxycarbonylamino-3-methoxycarbonyl-1-carba(dethia)-3-cephem-4-carboxylate A. Preparation of 2-(dimethyl-t-butylsilyloxy)propionitrile To a solution of 2-cyanoethanol (7.0 g, 98.48 mmole) in 75 ml of DMF was added dimethyl-t-butylchlorosilane (16.028 g, 106.36 mmole) followed by imidazole (8.17 g, 120 mmole). The reaction mixture was stirred for about 15 hours and was poured into a mixture of 250 ml of diethyl ether and 200 ml of 1N hydrochloric acid. The ether layer was separated and washed twice with 150 ml of 1N hydrochloric acid. The organic layer was separated, dried over magnesium sulfate, filtered and evaporated under vacuum. The silyl ether product was obtained as an oily residue. The residue was diluted with 100 ml of toluene and the solution evaporated. This procedure was repeated three times to provide 17.26 g of 2-(dimethyl-t-butylsilyloxy)propionitrile as a colorless liquid (94.7% yield).

90 MHz, NMR (CDCl$_3$, δ): 0.1 (s, 6H, methyl H), 0.9 (s, 9H, t-but H), 2.9 (t, J=6, 2H, CH$_2$CN), and 3.8 (t, J=6, 2H, SiO—CH$_2$).

B. 3-(Dimethyl-t-butylsilyloxy)propionaldehyde

To a solution of 3-(dimethyl-t-butylsilyloxy)propionitrile (6.04 g, 32.65 mmole) in 50 ml of THF and cooled to a temperature of 0° C. was added with a syringe, di-isobutylaluminum hydride (60 mmole in 60 ml of THF) and the mixture was allowed to warm to room temperature. After a thin layer chromatogram of the reaction mixture indicated that very little reaction had occurred, the reaction mixture was heated to reflux for a few minutes. The reaction mixture was then cooled to room temperature and poured into a stirred mixture of 150 ml of 1M tartaric acid and 200 ml of diethyl ether. Some gas evolution occurred and the mixture was transferred to a separatory funnel with diethyl ether. The ether layer was separated, dried with magnesium sulfate, filtered, and evaporated in vacuo. The liquid residue containing some suspended solids was diluted with hexane, filtered and the precipitate washed with hexane. The filtrate and washings were concentrated in vacuo to provide 3.7 g of the silyloxy propionaldehyde as a light yellow liquid (60.3% yield). The NMR spectrum indicated the product to be about 75% pure and contaminated with some starting material and silanol.

90 MHz, NMR (CDCl$_3$, δ): 0.2 (s, 6H, methyl H), 0.8 (s, 9H, t-but H), 2.5 (dt, J=2.5, 6, 2H, CH$_2$CO), 3.9 (t, J=6, 2H), and 9.5 (t, J=2.5, 1H, COH).

C. Imine Formed with Benzylamine and 3-(Dimethyl-t-butylsilyloxy)propionaldehyde To a solution of the silyloxypropionaldehyde prepared as described in B. above (2.5 g, 13.3 mmole) in about 20 ml of toluene were added benzylamine (10.64 mmole, 1.16 ml) and about 3-4 g of 4A molecular sieves. The mixture was occasionally swirled gently over 25 minutes to form the imine of the silyloxyaldehyde and benzylamine.

D.

N-Benzyl-3β-[(4S)-phenyl-1,3-oxazolidin-2-one-3-ylacetylamino]-4β-(2-dimethyl-t-butylsilyloxyethyl)azetidin-2-one To a solution of (4S)-phenyl-1,3-oxazolidin-2-one-3-yl acetic acid (2.2 g, 9.95 mmole) in 20 ml of toluene were added 1.45 g (11.44 mmole) of oxalyl chloride. The yellow solution was stirred for one hour and was then evaporated to provide the corresponding acid chloride as a yellow oil. The acid chloride was dissolved in 20 ml of methylene chloride and the solution was cooled to a temperature of about −78° C. Triethylamine (14.93 mmole, 2.08 ml) was added to the solution of the acid chloride and the solution was stirred for a few minutes at room temperature. The solution of the imine prepared as described above in C. was added to the acid chloride solution via cannula and the reaction mixture was allowed to slowly warm to a temperature of about 15°-20° C. over 2 hours. The reaction mixture was then poured into a mixture of 30 ml of methylene chloride and 30 ml of 1N hydrochloric acid and the organic layer was separated. The organic layer was washed with 40 ml of an aqueous saturated sodium bicarbonate solution and with 40 ml of water and was dried over magnesium sulfate, filtered, and evaporated under vacuum. The azetidinone was obtained as a reddish oil. The oil was chromatographed over 100 g of silica gel using 35% ethyl acetate/hexane for elution. The desired fractions were combined and concentrated in vacuo to a light pink solid. The solid was washed with hexane to remove the color and to yield 1.03 g of the azetidinone as a white solid (21.5% yield).

$[\alpha]_D^{25} = +79.2°$.

Mass spectrum: (M+) 480; (M+-t-butyl) 423.

IR 1750 cm$^{-1}$ ($\beta$-lactam).

Elemental analysis calculated for $C_{27}H_{36}N_2O_4Si$:

| Theory | Found |
|---|---|
| C, 67.47 | C, 67.61 |
| H, 8.55 | H, 8.78 |
| N, 5.83 | N, 6.03 |

90 MHz, NMR (CDCl$_3$, $\delta$): 0.0+0.25 (2s, 6H, methyl H), 0.8 (s, 9H, t-but H), 1.6 (m, 2H, CH$_2$ H), 3.5 (t, J=6, 2H, SiOCH$_2$ H), 3.8 (dt, J=5 and 6, 1H, C$_4$H), 7.1 to 7.5 (m, 10H, phenyl H).

E.
3$\beta$-t-Butyloxycarbonylamino-4$\beta$-[2-(dimethyl-t-butyl-silyloxy)ethyl]azetidin-2-one To 430 ml of liquid ammonia was added 2.385 g (343.71 mmole) of lithium washed with hexane and the mixture was stirred for about 20 minutes to dissolve the lithium. A solution of the N-benzylazetidinone prepared as described above in D. in 87 ml of THF containing 8.496 g (114.49 mmole, 10.8 ml) of t-butanol was added to the lithium-ammonia solution and the mixture was stirred vigorously for 50 minutes. A mixture of methyl alcohol-toluene (87 ml, 1:1) was added to the mixture followed by 21.7 ml of acetic acid. The ammonia was distilled off and the residue was acidified to pH 5 by the addition of 45 ml of acetic acid. A mixture of isopropyl alcohol in chloroform (500 ml, 25%) was added to the concentrate followed by 300 ml of a saturated aqueous sodium bicarbonate solution to adjust the pH of the mixture to pH 9. The organic layer was separated and the aqueous layer was washed twice with 200 ml of 25% isopropyl alcohol in chloroform. The washes were combined with the organic layer, dried over magnesium sulfate, filtered, and concentrated in vacuo to yield 9.3 g of crude 3$\beta$-amino-4$\beta$-(2-dimethyl-t-butylsilyloxyethyl)azetidin-2-one. The crude 3-amino compound was dissolved in 50 ml of methylene chloride and 8.486 g (38.88 mmole, 8.486 ml) of di-t-butyl-dicarbonate were added to the solution. The mixture was allowed to stir overnight and was then evaporated under vacuum to yield 14.67 g of the 3$\beta$-t-butyloxycarbonylamino acylation product. The product was chromatographed on 150 g of silica gel using ethyl acetate/hexane, 50/50 for elution. The fractions containing the desired product were combined and evaporated in vacuo to yield 11.88 g of 3$\beta$-t-butyloxycarbonylamino-4-(2-dimethyl-t-butylsilyloxyethyl)azetidin-2-one.

90 MHz, NMR (CDCl$_3$, $\delta$): 0.0 (s, 6H, methyl H), 0.8 (s, 9H, t-but H), 1.4 (s, 9H, t-butyloxy H), 1.7 (m, 2H, CH$_2$ H), 3.6 (t, J=5, 2H, CH$_2$ H), 3.9 (m, 1H, C$_4$H), 5.0 (dd, J=5 and 9, 1H, C$_3$H), 5.5 (d, J=9, 1H, amide H), and 6.2 (broad s, 1H, NH).

F.
3$\beta$-t-Butyloxycarbonylamino-4-(2-hydroxyethyl)azetidin-2-one

To a solution of t-butyloxycarbonylaminoazetidinone prepared as described in E. above (11.88 g, 34.48 mmole) in 12 ml of THF was added at 0° C. tetrabutylammonium fluoride (10.412 g, 39.5 mmole) and the mixture was allowed to stir for about 1.5 hours. The reaction mixture was evaporated under vacuum to obtain the product as an oil. The oil was filtered through 100 g of silica gel using 10% ethyl alcohol in ethyl acetate. The filtrate was evaporated under vacuum to provide the product as a yellow solid. The solid was mixed with hexane, sonicated, and filtered to yield 6.28 g of the 4$\beta$-(2-hydroxyethyl)azetidinone as a white solid (79.5% yield). The product was shown to be pure cis isomer by its NMR spectrum.

90 MHz, NMR (CDCl$_3$, $\delta$): 1.4 (s, 9H, t-butyloxy), 1.7 (m, 2H, CH$_2$ H), 3.0 (broad s, 1H, OH H), 3.7 (m, 2H, CH$_2$ H), 3.9 (m, 1H, C$_4$H), 5.0 (dd, J=5 and 8, 1H, C$_3$H), 5.8 (d, J=8, 1H, amide H), and 6.8 (broad s, 1H, NH).

G.
3$\beta$-t-Butyloxycarbonylamino-4$\beta$-(2-metylsulfonyloxyethyl)azetidin-2-one To a solution of the 2-hydroxyethyl substituted azetidinone, prepared as described in F. above (6.28 g, 27.424 mmole) in a mixture of 200 ml of chloroform and 100 ml of dioxane were added triethylamine (11.1 g, 109.7 mmole) and methanesulfonyl chloride (6.283 g, 54.85 mmole). The reaction mixture was stirred for one hour and was then poured into a mixture of 300 ml of methylene chloride and 150 ml of a saturated sodium bicarbonate solution. The organic phase was separated and the aqueous phase was washed twice with 150 ml of methylene chloride. The washes and the organic layer were combined, dried over magnesium sulfate, filtered and evaporated under vacuum to yield an oily solid. The solid was triturated with a mixture of diethyl ether and hexane, 50/50, filtered, dried to yield 8.4 g of the corresponding methanesulfonyloxy derivative.

H.
3$\beta$-t-Butyloxycarbonylamino-4$\beta$-(2-iodoethyl)azetidin-2-one A solution of 8.4 g of the mesylate ester prepared as described in G. above (27.3 mmole) in 400 ml of acetone and containing sodium iodide (16.5 g, 110.0 mmole) was heated at the reflux temperature for 4 hours. Another 2 g of sodium iodide were added and the mixture was heated at the reflux temperature for an additional hour. The reaction mixture was evaporated under vacuum and the residue treated with methylene chloride. The insoluble material was filtered and the filtrate was concentrated under vacuum to a brownish oil. The oil was dissolved in 80% ethyl acetate/hexane and filtered through 200 g of silica gel. The filtrate was evaporated to yield 7.65 g of the product as a yellowish solid. The solid was dissolved in the minimum amount of hot ethyl acetate and the warm solution diluted with hexane. The product precipitated to yield 4.9 g of a first crop of the 2-iodoethyl compound as a white solid and 1.65 g as a second crop (70.6% yield).

90 MHz NMR (CDCl$_3$, $\delta$): 1.4 (s, 9H, t-butyloxy H), 2.1 (m, 2H, CH$_2$ H), 3.1 (t, J=5, 2H, CH$_2$I H), 3.9 (dt, J=5 and 7, 1H, C₄H), 5.1 (m, 2H, C₄H and amide H), and 6.2 (broad s, 1H, NH).
$[\alpha]_D^{25} = +50.65$.
IR (CHCl₃) 1770 cm⁻¹ (β-lactam carbonyl).
Elemental analysis calculated for $C_{10}H_{17}N_2O_3I$:

|   | Theory | Found |
|---|--------|-------|
| C | 35.31 | 35.52 |
| H | 5.04 | 4.74 |
| N | 8.24 | 8.08 |

I. t-Butyl 7β-t-butyloxycarbonylamino-3-methoxycarbonyl-1-carba-3-cephem-4-carboxylate To a 50 ml round bottom flask, flame dried and flushed with dry nitrogen, was added the 2-idoethylazetidinone prepared as described above in H. (1.0 g, 2.941 mmmole) and THF and the solution was cooled to a temperature of about −78° C. To the cold solution was added di-(trimethylsilyl)lithiumamide (2.82 ml, 2.822 mmole) and the mixture was stirred in the cold for about 30 minutes. Next, via cannula, was added 2-phenylsulfinylmaleic acid 1-methyl 4-t-butyl diester (0.927 g, 2.985 mmole) and the reaction mixture was stirred for about 10–15 minutes. 1,3-Dimethyl-3,4,5,6-tetrahydro-2-(1H)-pyrimidonone was added to the reaction mixture which then was allowed to warm slowly to room temperature over about 2 hours. The reaction mixture was stirred at room temperature for about 45 minutes, poured into a mixture of 50 ml of an aqueous ammonium chloride solution and 150 ml of ethyl acetate. The organic phase was separated, dried over magnesium sulfate, filtered and evaporated under vacuum to a yellow oil. The oil was chromatographed on 100 g of silica gel using 25% ethyl acetate/hexane for elution. The fractions containing the desired product were combined and evaporated under vacuum to yield 560 mg of the product as a white foam. NMR indicated the product to be about 80% pure. The product was further purified on preparative thick layer plates (4×2 mm) using 25% ethyl acetate in hexane to give 520 mg of the title compound in about 90% purity.

90 MHz NMR (CDCL₃, δ): 1.4 (s, 9H, t-butyl H), 1.5 (s, 9H, t-butyl H), 3.7 (s, 3H, COOCH₃ H), 3.9 (m, 1H, C₆H), 4.9–5.1 (m, 2H, C₇H and amide H).
Mass Spec. 396 (M+), 340 L (M+—C₄H₈).
IR (CHCl₃, δ) 1781 cm⁻¹ β-lactam carbonyl
Elemental analysis calculated for $C_{19}H_{28}N_2O_7$

|   | Theory | Found |
|---|--------|-------|
| C | 57.56 | 57.63 |
| H | 7.12 | 6.84 |
| N | 7.07 | 7.08 |

EXAMPLES 2 THROUGH 8

In a procedure analogous to Example 1 (I), various compounds of Formula (BB) were utilized, thereby yielding compounds of Formula (2):

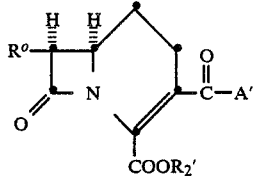

(2)

| Example | R⁰ | R₂' | A¹ | Spectral Data |
|---------|-----|------|-----|---------------|
| 2 | t-Boc | —CH₂CH=CH₂ | —OCH₂CH=CH₂ | 90 MHz NMR (CDCl₃, δ): 1.45 (s, 9H, t-Butyl), 3.9 (m, 1H, C₆H), 4.65 (dm, J=6Hz, 2H, —OC<u>H</u>₂CH), 4.75 (dm, J=6Hz, 2H, —OC<u>H</u>₂CH), |
| 3 | t-BOC | —CH₂CH=CH₂ | —O—CH₂—⌬ | 90 MHz NMR (CDCl₃, δ): 1.40 (s, 9H, t-Butyl), 3.85 (m, 1H, C₆H), 4.55 (m, 2H, —OC<u>H</u>₂CH), 5.1 (s, 2H, —OC<u>H</u>₂φ), 7.3 (s, 5H, —C₆H₅), |
| 4 | t-BOC | —CH₂CH=CH₂ | —O—CH₂—CH₂—CH₂—CH₂ | 90 MHz NMR (CDCl₃, δ): 0.9 (t, J=7 Hz, —CH₃), 1.4 (s, 9H, t-Butyl), 2.9 (m, 1H), 3.8 (m, 1H, C₆H), 4.1 (dm, J=5Hz, 2H, —OC<u>H</u>₂CH₂), 4.75 (dm, J=5Hz, 2H, —OC<u>H</u>₂CH), |
| 5 | t-BOC | —CH₂CH=CH₂ | —CH₃ | 90 MHz NMR (CDCl₃, δ): 1.45 (s, 9H, t-Butyl), 2.3 (s, 3H, CH₃), 3.8 (dm, J=11Hz, 1H, C₆H), 4.75 (dm, J=5Hz, 2H, —OC<u>H</u>₂CH); IR (CHCl₃) 1779 cm⁻¹ β-lactam carbonyl; Mass spec 364 (M+), 308 (M+—C₄H₈) |
| 6 | t-BOC | —C(CH₃)₃ | —OCH₂CH=CH₂ | 90 MHz NMR (CDCl₃, δ): 1.4 (s, 9H, t-Butyl), 1.5 (s, 9H, t-Butyl), 2.9 (m, 1H), 3.8 (m, 1H, C₆H), 4.6 (bd, J=4; 2H, —OC<u>H</u>₂CH), |
| 7 | t-BOC | —CH₂CH=CH₂ | —OCH₂CH₂CH₂CH₂CH₂CH₂ | 300 MHz NMR (CDCl₃, δ): 0.9 (t, J=7, 3H, —CH₃), 1.5 (s, 9H, t-butyl), 2.15 (m, 1H, 2,35 (m, 1H), 2.9 (dd, J=4 and 19, 1H), 3.9 (m, 1H, C₆H), 4.15 (m, 2H, —OC<u>H</u>₂CH₂), 4.8 (m, 2H, —OC<u>H</u>₂CH), |

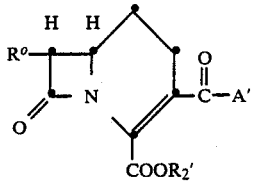

(2)

| Example | $R^o$ | $R_2'$ | $A^1$ | Spectral Data |
|---|---|---|---|---|
| 8 | t-BOC | —CH₂CH=CH₂ | —OCH₂CH₂Si(CH₃)₃ | 5.05 (bd, J=5, 1H), 5.25 (m, 1H), 5.3 (dm, J=12, 1H), 5.45 (dm, J=19, 1H), 6.0 (m, 1H). 90 MHz NMR (CDCl₃, δ): 0.05 (s, 9H, —CH₃), 1.0 (m, 2H, —CH₂Si), 1.45 (s, 9H, t-Butyl), 2.9 (m, 1H, 3.85 (dm, J=13, 1H, C₆H), 4.2 (m, 2H, —OCH₂CH₂), 4.75 (dm, J=5, —OCH₂CH), |

EXAMPLE 9

7β-[2-(2-Aminothiazole-4-yl)-2-methoxyiminoacetylamino]-3-methoxycarbonyl-1-carba-3-cephem-4-carboxylic acid To a solution of t-butyl 7β-t-butyloxycarbonylamino-3-methoxycarbonyl-1-carba-3-cephem-4-carboxylate (400 mg, 1.009 mmole) in acetonitrile was added toluenesulfonic acid monohydrate (391.5 mg, 2.058 mmole) and the solution was stirred for 2½ hours at room temperature. The reaction mixture was poured into 100 ml of chloroform containing 40 ml of a saturated aqueous solution of sodium bicarbonate. The organic phase was separated and the aqueous phase was washed twice with 75 ml portions of chloroform. The chloroform washings were combined with the organic layer and were dried over magnesium sulfate, filtered and evaporated under vacuum to yield the 7β-amino t-butyl ester compound.

The 7β-amino ester was dissolved in about 5 ml of THF and pyridine (159.6 mg, 2.018 mmole, 0.163 ml) was added.

In a separate flask, sodium 2-(2-t-butyloxycarbonylaminothiazole-4-yl)-2-methoxyimino acetate in 10 ml of dry THF was treated with oxalyl chloride (128.1 mg, 1.009 mmole) and one drop of DMF, and the mixture was allowed to stir for 2 hours. The mixture was evaporated to remove the THF and the acid chloride product was dried under vacuum.

A solution of the thiazoleoximino acetyl chloride prepared as described above in dry THF was added via pipette to the solution of the 7β-amino ester in pyridine and the acylation mixture stirred for about 30 minutes at 0° C. The reaction mixture was poured into a mixture of 100 ml of ethyl acetate and 50 ml of an aqueous saturated sodium bicarbonate solution. The organic layer was separated and was washed twice with 50 ml portions of 1N hydrochloric acid. The organic layer was dried over magnesium sulfate, filtered and evaporated under vacuum to yield 350 mg of crude acylation product, t-butyl 7β-[2-(2-t-butyloxycarbonylaminothiazole-4-yl)-2-methoxyiminoacetylamino]-3-methoxycarbonyl-1-carba-3-cephem-4-carboxylate. The product was further purified via preparative thick layer chromatography on plates coated with silica gel employing sequential elution with 35% diethyl ether/methylene chloride, 75% ethyl acetate/hexane, and 35% diethyl ether/methylene chloride. There were isolated 65 mg of the purified product.

90 MHz NMR (CDCl₃, δ): 1.45 (s, 9H, t-butyl H), 1.48 L (s, 9H, t-butyl H), 3.7 (s, 3H, CO₂CH₃), 4.0 (m, 1H, C₆H), 4.0 (s, 3H, =N—OCH₃), 5.6 (dd, J=5 and 7), 1H, C₇H), 7.0 L (s, 1H, thiazole H), 7.8 (broad d, 1H, J=7, amide H), 9.2 (broad s, 1H, amide H).

IR (CHCl₃) 1773 cm⁻¹ β-lactam carbonyl.

The acylation product prepared by the procedure described above (96 mg, 0.1698 mmole) was treated with 4 ml of 98% formic acid and the mixture was stirred at room temperature for between about 8 and about 9 hours. The reaction mixture was concentrated by evaporation to a volume of about ¼ ml. Diethyl ether was added to the concentrate and the mixture was sonicated. The ether suspension was transferred to a centrifuge tube via a pipette and the suspension was centrifuged. The solid was collected and set aside. The ether supernatant was concentrated and the precipitated solid was dissolved in methanol. Ether was added and the ethereal solution was centrifuged. The solid product was collected as before and the process was repeated. All solid crops of product were combined to yield 40 mg of the title compound in 90.4% purity via HPLC.

270 MHz NMR (CD₃OD, δ): 3.7 (s, 3H, CO₂CH₃), 3.8 (m, 1H, C₆H), 5.5 (d, J=5, 1H, C₇H), 4.0 (s, 3H, =N—OCH₃), and 6.8 (s, 1H, thiazole H).

IR (KBr) 1772 cm⁻¹ β-lactam carbonyl.

Mass Spec. 424 (M⁺+1) 391 (M⁺—CH₃OH).

EXAMPLE 10

7β-(2-Thienylacetylamino)-3-methoxycaronyl-1-carba-3-cephem-4-carboxylic acid

A mixture of t-butyl 7β-t-butyloxycarbonylamino-3-methoxycarbonyl-1-carba-3-cephem-4-carboxylate (180 mg, 0.4541 mmole) and about 2 ml of trifluoroacetic acid was stirred at a temperature of about 0° C. for 2 hours. Diethyl ether was added to the solution and the product precipitated as a white solid. The mixture was transferred to a centrifuge tube and placed in a centrifuge. The supernatant was decanted, fresh ether added, the mixture sonicated and recentrifuged. The ether was decanted and the solid 7β-amino-3-methoxycarbonyl-1-carba-3-cephem-4-carboxylic acid was dissolved in a mixture of 1 ml of acetonitrile, 2½ ml of THF, and sofylated with BSTFA (337 mg, 1.31 mmole, 53 µl). The solid nucleus dissolved and the solution was cooled to a temperature of about 0° C. Pyridine (52 mg, 0.6548 mmole, 41 μl) was added to the cold solution followed by 2-thiopheneacetyl chloride (53 mg). The mixture was stirred in the cold and was poured into a mixture of 40 ml of diethyl ether and 20 ml of water. The mixture was first extracted twice with 40 ml portions of diethyl ether and then the product was extracted from the mixture with 15% isopropanol in chloroform. The chloroform extract was dried over magnesium sulfate, filtered and evaporated under vacuum to obtain the product as a white solid. The product was triturated three times with a mixture of diethyl ether/hexane and was dried to yield 45 mg of the title compound.

300 MHz NMR (CDCl$_3$, δ): 1.4, 2.0, 2.3 and 2.8 (m, 4H, C$_1$H and C$_2$H), 3.7 (s, 3H, CO$_2$CH$_3$), 3.8 (s, 2H, thienyl-CH$_2$ H), 3.9 (m, 1H, C$_6$H), 5.4 (m, 1H, C$_7$H), 6.7 (broad d, 1H, amide H), 6.9–7.3 (m, 3H, thienyl H).

IR (KBr) 1774 cm$^{-1}$ β-lactam carbonyl.

Mass Spec. 364 (M$^+$) 332 (M$^+$—CH$_3$OH)

Elemental analysis calculated for C$_{16}$H$_{16}$N$_2$O$_6$S$_1$:

|   | Theory | Found |
|---|--------|-------|
| C | 52.74  | 52.53 |
| H | 4.43   | 4.50  |
| N | 7.69   | 7.49  |
| S | 8.80   | 8.62  |

EXAMPLE 11

Allyl 7β-t-butyloxycarbonylamino-3-methoxycarbonyl-1-carba-3-cephem-4-carboxylate By following the procedures described by Example 1I, 3β-t-butyloxycarbonylamino-4-(2-iodoethyl)azetidinone (2.2 g, 6.474 mmole) obtained as described by Example 1H, was reacted with 1-methyl 4-allyl 2-phenylsulfinylmaleic acid diester (Preparation 2) to yield 436 mg (18.24% yield) of the title compound crystalline from hexane.

90 MHz NMR (CDCl$_3$, δ): 1.45 (s, 9H, t-butyl), 3.7 (s, 3H, CO$_2$CH$_3$), 3.8 (m, 1H, C$_6$H), 4.9–5.2 (m, 2H, C$_7$H and amide H), 4.7 (broad d, J=5.5, 2H, —CH$_2$—CH═CH$_2$), 5.2–5.5 (m, 2H, —CH$_2$-CH═CH$_2$), and 5.7–6.2 (m, 1H, —CH$_2$—CH═CH$_2$).

EXAMPLE 12 t-Butyl 7β-[2-phenyl-(2-t-butyloxycarbonylamino)acetylamino]-3-methoxycarbonyl-1-carba-3-cephem-4-carboxylate To a solution of t-butyl 3β-t-butyloxycarbonylamino-3-methoxycarbonyl-1-carba-3-cephem-4-carboxylate (150 mg, 0.3784 mmole) prepared as described by Example 1I, in 2 ml of diethyl ether was added a solution of p-toluenesulfonic acid monohydrate in 0.5 ml of ethyl alcohol and the mixture was allowed to stir for one hour. The mixture was concentrated by evaporation in a rotary evaporator and 2 ml of ethyl alcohol was added and the mixture reevaporated at 40° C. The dilution with ethyl alcohol and evaporation was repeated twice and the product then dissolved in 40 ml of chloroform. The chloroform solution was added to 25 ml of a saturated aqueous solution of sodium bicarbonate and the mixture extracted with 40 ml of chloroform. The organic layer was dried over magnesium sulfate and evaporated under vacuum to provide 80 mg (71.43%) of the deprotected product, t-butyl 7β-amino-3-methoxycarbonyl-1-carba-3-cephem-4-carboxylate as an oil.

To a mixture of the 7-amino nucleus (80 mg, 0.27 mmole), 2-phenyl-2-t-butyloxycarbonylamino acetic acid (72 mg, 0.2835 mmole), and pyridine (0.036 ml, 0.447 mmole) and cooled to 0° C. was added phosphorus oxychloride (0.028 ml, 0.298 mmole) and the mixture was allowed to stir for about 40 minutes. The mixture was then poured into 60 ml of ethyl acetate and the solution was washed twice with 30 ml-portions of of 1N hydrochloric acid, twice with 30 ml-portions of a saturated aqueous solution of sodium bicarbonate and once with 30 ml of brine. The solution was dried over magnesium sulfate, filtered and evaporated under reduced pressure to provide the title compound as a white solid.

90 MHz NMR (CDCl$_3$, δ): 1.4 (s, 9H, t-butyl), 1.5 (s, 9H, t-butyl), 3.7 (s, 3H, CO$_2$CH$_3$), 3.8 (m, 1H, C$_6$H), 6.6 (d, J=6, 1H, amide H), and 7.3 (s, 5H, phenyl).

IR (CHCl$_3$): 1783 cm$^{-1}$ β-lactam carbonyl.

Mass Spec.: 529 (M$^+$).

EXAMPLES 13 THROUGH 27

Procedures described above in Examples 1 and 2, for reaction of Formulae (AA) with (BB), and deprotection of the R$^o$-moiety and re-acylation were utilized to provide compounds of the formula

| Example | R | A' | R₂ | Spectral Data |
|---|---|---|---|---|
| | 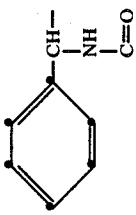 | | | |
| 13 |  | —OCH$_2$CH=CH$_2$ | —CH$_2$CH=CH$_2$ | 90 MHz NMR (CDCl$_3$, δ): 1.0, 1.7, 2.3 and 2.7 (m, 4H, C$_1$H and C$_2$H), 3.8 (m, 1H, C$_6$H), 6.1 (d, J=6, 1H), 7.3 (s, 5H, C$_6$H$_5$) |
| 14 | 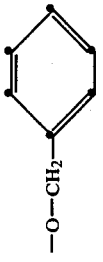 |  | —CH$_2$CH=CH$_2$ | 90 MHz NMR (CDCl$_3$, δ): 2.8 (m, 1H), 3.9 (m, 1H, C$_6$H), 4.6 (dm, J=5, 4H, —OCH$_2$CH) 5.3 (s, 2H, —OCH$_2$O), 6.4 (bd, J=6, 1H), 7.2 (s, 10H). |

-continued

| Example | R | A' | $R_2$ | Spectral Data |
|---|---|---|---|---|
| 15 | (thiophene-CH-NH-C(=O)-O-CH$_2$CH=CH$_2$) | —OCH$_3$ | —CH$_2$CH=CH$_2$ | 90 MHz NMR (CDCl$_3$, δ): 0.9 1.5, 2.1, and 2.6 (m, 4H, C$_1$H and C$_2$H), 3.65 (s, 3H, —OCH$_3$), 3.8 (m, 1H, C$_6$H), 4.5 (bd, J=5, 2H, —OC$\underline{H}_2$CH), 4.7 (bd, J=5, 2H, —OCH$_2$C$\underline{H}$), 6.65 (d, J=7, 1H). |
| 16 | (phenyl-CH-NH-C(=O)-O-CH$_2$CH=CH$_2$) | —OCH$_2$CH$_2$CH$_3$ | —CH$_2$CH=CH$_2$ | 90 MHz NMR (CDCl$_3$, δ): 0.9 (t, J=7, 3H, —CH$_3$), 2.2 (m, 1H), 2.7 (dd, J=4, 18, 1H), 3.8 (m, 1H, C$_6$H), 4.1 (t, J=7, 2H, —OC$\underline{H}_2$CH$_2$), 4.5 (d, J=4, 2H, —OC$\underline{H}_2$CH), 4.7 (d, J=5, 2H, —OCH$_2$C$\underline{H}$), 6.1 (d, J=7, 1H), 7.05 (bd, J=7, 1H), 7.25 (s, 5H, C$_6$H$_5$). |

-continued

| Example | R | A' | R$_2$ | Spectral Data |
|---|---|---|---|---|
| 17 | C$_6$H$_5$-CH(NH-C(O)-O-CH$_2$-CH=CH$_2$)- | —CH$_3$ | —CH$_2$CH=CH$_2$ | 90 MHz NMR (CDCl$_3$, δ): 2.2 (s, 3H, —CH$_3$), 2.55 (m, 1H, C$_6$H), 3.7 (m, 1H, —OCH$_2$CH), 4.5 (dm, J=6, 2H, —OCH$_2$CH), 4.7 (dm, J=6, 2H, —OCH$_2$CH), 6.95 (bd, J=7, 1H), 7.25 (s, 5H, C$_6$H$_5$). |
| 18 | (aminothiazole-C(=N-OCH$_3$)- with HN-C(O)-O-CH$_2$-CH=CH$_2$ on thiazole N) | —OCH$_2$—CH$_3$ | —CH$_2$CH=CH$_2$ | 90 MHz NMR (CDCl$_3$, δ): 1.2 (t, J=6, 3H, —CH$_3$) 2.9 (m, 1H) 4.0 (s, 3H, —OCH$_3$), 4.7 (bs, 4H, —OCH$_2$CH), 6.95 (s, 1H), 8.1 (d, J=7, 1H), 9.6 (bs, 1H). |
| 19 | (aminothiazole-C(=N-OCH$_3$)- with HN-t-BOC on thiazole N) | —OCH$_2$CH$_3$ | —CH$_2$CH=CH$_2$ | 90 MHz NMR (CDCl$_3$, δ): 1.3 (t, J=7, 3H, —CH$_2$CH$_3$), 1.5 (s, 9H, t-Butyl), 2.9 (m, 1H), 4.0 (m, 4H, —OCH$_3$ and C$_6$H), 4.2 (q, J=7, 2H, —OCH$_2$CH$_3$), 4.75 (dm, J=4, 2H, —OCH$_2$CH), 5.6 (dd, J=5 and 8, 1H, C$_7$H), 7.05 (s, 1H), 7.8 (d, J=8, 1H), 9.1 (bs, 1H). |

-continued

| Example | R | A' | R₂ | Spectral Data |
|---|---|---|---|---|
| 20 | (structure: thiazole with HN-t-BOC, C=N-OCH₃) | (structure: phenyl with -OCH₂-) | —CH₂CH=CH₂ | 90 MHz NMR (CDCl₃, δ): 1.5 (s, 9H, t-Butyl), 2.9 (m, 1H), 3.9 (m, 4H, —OCH₃ and C₆H), 4.5 (m, 2H), —OCH₂CH, 5.1 (s, 2H, —CH₂φ), 5.6 (dd, J=7 and 5, 1H, C₃H), 7.0 (s, 1H), 7.3 (s, 5H, C₆H₅), 7.7 (d, J=7, 1H). |
| 21 | (structure: thiazole with HN-CH(C₆H₅)₃, C=N-OCH₂C₆H₅) | (structure: phenyl with -OCH₂-) | —CH₂CH=CH₂ | 90 MHz NMR (CDCl₃, δ): 1.6 (m, 1H), 2.4 (m, 1H), 3.8 (m, 1H, C₆H), 4.5 (m, 2H, —OCH₂CH), 5.1 (m, 2H, —CH₂φ), 5.2 (s, 2H, —CH₂φ), 6.5 (d, J=8, 1H), 6.6 (s, 1H). |
| 22 | (structure: phenyl-CH(NH)-C(=O)-N-piperazinone with N-CH₂-CH₃) | —OCH₂CH₃ | —CH₂CH=CH₂ | 90 MHz NMR (CDCl₃, δ): 1.3 (t, J=7, 3H, —CH₃), 1.35 (t, J=7, 3H, —CH₃), 1.8 (m, 1H), 2.3 (m, 1H), 2.8 (m 1H), 3.6 (m, 4H), 3.8 (m, 1H, C₆H), 4.0 (m, 2H), 4.2 (q, J=7, 2H, —OCH₂CH₃) 4.8 (dm, J=5, 2H, —OCH₂CH), 7.3 (m, 5H, —C₆H₅). |

-continued
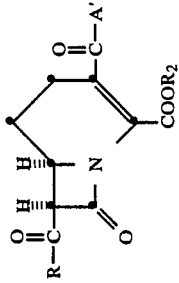
| Example | R | A' | $R_2$ | Spectral Data |
|---|---|---|---|---|
| 23 | 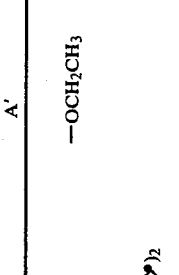 | —OCH$_2$CH$_3$ | —CH$_2$CH=CH$_2$ | 90 MHz NMR (CDCl$_3$, δ): 1.3 (t, J=7, 3H, —CH$_2$CH$_3$), 2.7 (m, 1H), 3.9 (m, 1H, C$_6$H), 4.2 (q, J=7, 2H, —OCH$_2$CH$_3$), 4.8 (dm, J=5, 2H, —OCH$_2$CH), 4.95 (d, J=4 2H, —OCH$_2$CO$_2$), 6.75 (s, 1H), 6.9 (s, 1H), 6.95 (bs, 1H), 7.3 (s, 25H, —C$_6$H$_5$), 7.8 (d, J=8, 1H) |
| 24 |  | —OCH$_2$CH$_3$ | —CH$_2$CH=CH$_2$ | 90 MHz NMR (CDCl$_3$, δ): 1.3 (t, J=7, 3H, —OCH$_2$CH$_3$), 2.4 (m, 1H), 3.8 (m, 1H, C$_6$H), 4.15 (q, J=7, 2H, —OCH$_2$CH$_3$), 4.7 (dm, J=6, 2H, —OCH$_2$CH), 5.2 (s, 2H, —CH$_2$φ), 6.35 (d, J=7, 1H), 6.8 (s, 1H), 6.9 (bs, 1H), 7.2 (s, 15H, C$_6$H$_5$), 7.3 (s, 5H, C$_6$H$_5$). |

-continued

| Example | R | A' | R₂ | Spectral Data |
|---|---|---|---|---|
| 25 | (structure: thiazole with N—H—C₃—phenyl, S, C=N—O—CH₂—(4-Cl-phenyl)) | —OCH₂CH₃ | —CH₂CH=CH₂ | No NMR |
| 26 | (structure: thiazole with N—H—t-BOC, S, C=N—OCH₃) | —OCH₂CH₂CH₂CH₃ | —CH₂CH=CH₂ | 90 MHz NMR (CDCl₃, δ): 0.9 (m, 3H, —CH₂C$\underline{H}_3$), 1.5 (s, 9H, t-Butyl), 3.95 (s, 3H, —OCH₃), 4.0 (m, 2H, —OCH₂CH₂), 4.7 (dm, J=5, 2H, —OC$\underline{H}_2$CH), 7.05 (s, 1H), 7.25, (d, J=7 1H), 8.5 (bs, 1H). |
| 27 | (structure: thiazole with N—H—C₃—phenyl, S, C=N—OCH₂CH₂—N(H)—t-BOC) | —OCH₂CH₃ | —CH₂CH=CH₂ | 90 MHz NMR (CDCl₃, δ): 1.3 (m, 3H, —OCH₂C$\underline{H}_3$), 1.3 (s, 9H, t-Butyl), 3.35 (bm, 2H, —OCH₂CH₂) 3.9 (m, 1H, C₆H), 4.15 (m 2H, —OC$\underline{H}_2$CH₃); 4.3 (m, 2H, —OC$\underline{H}_2$CH₂N), 4.7 (dm, J=6, 2H, —OC$\underline{H}_2$CH), 4.9 (t, J=7 1H, —NH—t-BOC), 5.5 (dd, J=4 and 8, 1H, 7.2 (s, 15H, C₆H₅), 8.1 (bd, J=8 1H). |

EXAMPLE 28

7β-(2-Phenyl-2-aminoacetylamino)-3-methoxycarbonyl-1-carba-3-cephem-4-carboxylic acid The following three methods were used to deprotect the t-BOC amino-protected t-butyl ester prepared as described above in Example 12 to provide the title compound.

Method A—Trimethylsilyl iodide

To a dry solution of the amino-protected ester (82 mg, 0.155 mmole) in freshly distilled chloroform and maintained under nitrogen was added via a syringe trimethylsilyl iodide (66.6 mg, 0.333 mmole) and the mixture was stirred for 2 hours. The thin layer chromatogram run on an aliquot of the reaction mixture showed one major spot. The reaction mixture was transferred to another flask containing methyl alcohol (1.0 mmole, 45 µl), pyridine (0.666 mmole, 54 µl) in methylene chloride and maintained at 0° C. Upon the addition of diethyl ether the product precipitated to form a suspension. The suspension was placed in a centrifuge tube and centrifuged. The supernatant was decanted and the solid dissolved in the minimum volume of methyl alcohol. Diethyl ether was again added to precipitate the product and form a suspension. The preceding process of centrifuging and decanting was repeated twice to provide the product as a light yellow solid. The product was dissolved in methyl alcohol, 20 ml of acetonitrile were added and the product evaporated under vacuum. The solution-evaporation with methyl alcohol acetonitrile was repeated four times to provide 32 mg of the title compound as a light yellow solid (56% yield).

Method B—Formic Acid

The t-BOC amino-protected t-butyl ester obtained as described by Example 12 (5.5 mg, 0.0104 mmole) was mixed with 1 ml of 98% formic and the mixture was allowed to stir for about 5 hours. A thin layer chromatogram of the reaction mixture showed mainly one spot and the absence of a spot corresponding to the starting material. The mixture was evaporated under vacuum at 30° C. to a volume of about ¼ ml. Upon the addition of diethyl ether the product formed as a solid and the mixture was sonicated. The mixture was transferred to a centrifuge tube with diethyl ether and centrifuged. The supernatant was decanted and the solid was taken up in the minimum amount of ethyl alcohol. Diethyl ether was added again to precipitate the solid which was again centrifuged. The process was repeated three times and the solid transferred to a 25-ml flask with methyl alcohol and again concentrated by evaporation. Acetonitrile was added and the mixture was evaporated under vacuum. The process was repeated four times using 12 ml of acetonitrile each time. There were obtained 2.4 mg of the title compound.

Method C

The process of Method B was repeated using formic acid, except that the mixture of formic acid and the amino-protected ester was allowed to react for 7.5 hours. From 105 mg of the amino-protected t-butyl ester (0.1983 mmole) there were obtained 40 mg of the title compound which was shown to be 65% pure by isocratic HPLC.

EXAMPLE 29

Allyl 7β-[2-phenyl-(2-allyloxycarbonylamino)acetylamino]-3-methoxycarbonyl-1-carba-3-cephem-4-carboxylate Allyl 3β-t-butyloxycarbonylamino-3-methoxycarbonyl-1-carba-3-cephem-4-carboxylate (433 mg, 1.1383 mmole) prepared as described by Example 11 was dissolved in approximately 8 ml of isopropyl alcohol and p-toluenesulfonic acid monohydrate (223 mg, 1.1724 mmole) was added to the solution. The mixture was swirled until solution occurred and the solution concentrated by evaporation on a rotary evaporator at 45° C. The residue was redissolved in isopropyl alcohol and reevaporated at 45° C. The evaporation and solution procedure was repeated five times to provide the 7β-amino allyl ester nucleus as a solid. The product was dissolved in 10 ml of chloroform and the solution was poured into a mixture of 40 ml of a saturated aqueous solution of sodium bicarbonate and 80 ml of chloroform. The layers were separated and the aqueous layer was extracted twice with 50 ml-portions of chloroform. The extracts were combined with the organic layer, dried over magnesium sulfate, filtered and evaporated under vacuum to provide 300 mg of the nucleus ester as a yellowish oil. A thin layer chromatogram of the nucleus ester showed one spot.

The nucleus ester was dissolved in about 2–3 ml of chloroform and 2-phenyl-2-allyloxycarbonylaminoacetic acid (281 mg, 1.1952 mmole) and pyridine (1.8845 mmole, 0.153 ml) were added and the mixture cooled to 0° C. Next, phosphorus oxychloride (1.26 mmole, 0.117 ml) was added and the mixture was stirred at room temperature for 30–40 minutes. The reaction mixture was poured into 100 ml of ethyl acetate and the solution was washed twice with 45 ml-portions of 1N hydrochloric acid, twice with 45 ml-portions of a saturated aqueous solution of sodium bicarbonate and with 50 ml of brine. The solution was then dried over magnesium sulfate, filtered and evaporated under reduced pressure to provide the product as an off-white solid. A thin layer chromatogram of the solid showed one major spot and a minor spot with a lower Rf value. The solid was chromatographed on 20 g of silica gel using 45% ethyl acetate/hexane for elution. Multiple fractions were collected and those fractions containing the desired product as shown by TLC were evaporated under reduced pressure to yield 266 mg of the title compound (47% yield) as a white solid.

90 MHz NMR (CDCl$_3$, δ): 3.6 (s, 3H, CO$_2$CH$_3$), 3.8 (m, 1H, C$_6$H), 4.5 and 4.7 (d, J=6, 4H, both —CH$_2$—CH=CH$_2$), 5.6–6.1 (m, 2H, both —CH$_2$—CH=CH$_2$), 6.1 (d, J=6, 1H, amide H), and 7.2 (m, 6H, amide H+phenyl H).

EXAMPLE 30

7β-(2-phenyl-2-aminoacetylamino-3-methoxycarbonyl-1-carba-3-cephem-4-carboxylic acid To a solution of the allyl-protected compound prepared as described by Example 29 above (226 mg, 0.5346 mmole) in about 3 ml of acetonitrile containing 1 ml of diethyl ether was added triphenylphosphine (28 mg, 0.1069 mmole) and palladium diacetate (5.25 mg, 0.0214 mmole) and the mixture was stirred for 10–15 minutes at 0° C. To the cold mixture was next added tri-(n-butyl) tin hydride (318.9 mg, 1.099 mmole) and the mixture was stirred for between 20 and 30 minutes while warming to room temperature. Concentrated hydrochloric acid (1.6 μl) was added to the mixture via a micro-syringe causing the precipitation of the product as a white solid. The mixture was diluted with 2 ml of acetonitrile and 2 ml of diethyl ether and was transferred to a centrifuge tube. The suspension was centrifuged and the supernatant decanted. The white solid was washed by centrifuging and decanting three times using 25 ml of 1-1 acetonitrile-diethyl ether and three times with 25 ml-portions of diethyl ether. The solid product was dried in a vacuum oven at room temperature to yield 165 mg of the title compound as an off-white solid (82.65%).

The product obtained above was purified as follows: to a 15 ml centrifuge tube was added 123.5 mg (0.3307 mmole) of the product and 3 ml of acetonitrile were added. To the mixture was added 1N hydrochloric acid via pipette and the mixture was swirled until most of the solid had gone into solution. The mixture was then centrifuged and the clear supernatant was separated from the undesired solid precipitate and transferred with acetonitrile washing to another centrifuge tube. The clear solution was treated with 1.5N ammonium hydroxide until the pH was adjusted to approximately 4 to 4.5. A clear oil separated from solution and the mother liquor was pipetted off into another centrifuge tube. To the oil were added 7 ml of acetonitrile and the oil solidified. The solid was washed twice with 8 ml-portions of acetonitrile and centrifuged and the washings were added to the mother liquor. From the mother liquor a second crop of product precipitated. The first crop of product was washed with 8 ml of diethyl ether, centrifuged and the ether decanted. The solid product was then dried in a vacuum oven at room temperature to yield 92.3 mg of the first crop material as a white solid. The first crop was 87% pure as indicated by HPLC. The second crop material was washed in the same manner and centrifuged and dried in a vacuum oven at room temperature to yield 13 mg of the product as a white solid. The product was 97% pure as determined by HPLC. A third crop of 5 mg was also obtained. Crops 1 and 3 were combined and washed as described above to give three crops as follows:

First crop, 84.5 mg (93% pure);
Second crop, 13 mg (98% pure); and
Third crop, 6.0 mg, (95% pure).

The purity of the three crops obtained above was determined by isocratic HPLC.

The purified product gave the following spectra.

300 MHz NMR ($D_2O$, δ): 1.05, 1.7, 2.2, and 2.6 (m, 4H, $C_1H$ and $C_2H$), 3.7 (s, 3H, $CO_2\underline{CH_3}$), 3.95 (m, 1H, $C_6H$), 5.2 (s, 1H, phenyl —C$\underline{H}$—$NH_3^+$), 5.4 (d, J=6, 1H, $C_7H$), and 7.6 (m, 5H, phenyl H).

Mass Spec. (FAB) 374 (M+1), 342 (M+—$OCH_3$).

IR (KBr) 1771 cm$^{-1}$ β-lactam carbonyl.

EXAMPLE 31 t-Butyl 7β-t-butyloxycarbonylamino-3-acetyl-1-carba-3-cephem-4-carboxylate

To a dry solution of 3β-t-butyloxycarbonylamino-4-(2-iodoethyl)azetidinone (1.082 mg, 3.18 mmole) in 9 ml of THF and cooled to −78° C. was added bis(trimethylsilyl)lithium amide (3.08 mmole, 3.08 ml) and the mixture was allowed to stir for 15–20 minutes. A solution of t-butyl 3-phenylsulfinyl-4-oxopent-2-enoate (950 mg, 3.23 mmole, Preparation 12) in 6 ml of dry THF and cooled to −78° C. was added via cannula over a few minute to the above solution of the iodoazetidinone. The reaction mixture was stirred for about 15 minutes and was then treated with 2.7 ml of DMPU and allowed to warm slowly to room temperature over approximately 2 hours. The mixture was then stirred for about 1.5 hours at room temperature and was then poured into a mixture of 40 ml of a saturated aqueous solution of ammonium chloride in 100 ml of ethyl acetate. The organic layer was separated, dried over magnesium sulfate, filtered and evaporated under vacuum to yield the product as a yellow oil. Toluene, 100 ml, was added to the oil and the mixture was heated at the reflux temperature for 5 minutes to eliminate any remaining sulfoxides. The mixture was then concentrated on a rotary evaporator to yield the product as a brownish oil. The oil was chromatographed on 80 g of silica gel using 40% ethyl acetate/hexane for elution. The fractions containing the desired product was combined and concentrated under reduced pressure to a foam. The foam was dissolved at the reflux temperature in 80 ml of hexane containing 2 ml of diethyl ether. The solution was allowed to cool slowly overnight. The product crystallized from solution to yield 186 mg (15.9%) of the title compound as white crystals.

90 MHz NMR ($CDCl_3$, δ): 1.4 (s, 9H, t-butyl), 1.5 (s, 9H, t-butyl), 2.3 (s, 3H, —CO$\underline{CH_3}$), 3.8 (dm, J=11, 1H, $C_6H$), 5.1 (m, 2H, $C_7H$ and amide H).

EXAMPLE 32

Allyl 7β-t-butyloxycarbonylamino-3-ethoxycarbonyl-1-carba-3-cephem-4-carboxylate The title compound was prepared by reacting according to the procedures described by Example II 3β-t-butyloxycarbonylamino-4-(2-iodoethyl)azetidinone (1.13 g, 3.3235 mmole) in dry THF with 1-ethyl 4-allyl 2-phenylsulfinylmaleic acid diester (1.035 g) prepared as described in Preparation 3. The product was isolated crude as a brownish oil and was purified by chromatography on 75 g of silica gel using 30% ethyl acetate/hexane for elution. Multiple fractions were collected and those containing the title compound as shown by thin layer chromatography were combined and evaporated under vacuum to yield 410 mg of the product as a foam. The product was obtained crystalline by dissolving the foam at the reflux temperature in 80 ml of hexane containing 3 ml of diethyl ether and allowing the solution to stand in the refrigerator overnight. There were obtained 285 mg of the crystalline title compound (22% yield).

90 MHz NMR ($CDCl_3$, δ), 1.3 (t, J=8, 3H, $CO_2CH_2\underline{CH_3}$), 1.4 (s, 9H, t-butyl H), 3.9 (dm, J=11, 1H, $C_6H$), 4.2 (q, J=7, 2H, $CO_2\underline{CH_2}CH_3$), 4.8 (m, 2H, $CO_2\underline{CH_2}CH=CH_2$), and 5.8–5.2 (m, 1H, $CO_2CH_2$—$CH=CH_2$).

Mass Spec. 394 (M+338 (M+—$C_4H_8$).

IR ($CHCl_3$) 1782 cm$^{-1}$ β-lactam carbonyl.

Elemental analysis calculated for $C_{19}H_{29}N_2O_7$:

|   | Theory | Found |
| --- | --- | --- |
| C | 57.86 | 57.61 |
| H | 6.64 | 6.71 |
| N | 7.10 | 6.86 |

EXAMPLE 33

Allyl
7β-[2-phenyl-(2-allyloxycarbonylamino)acetylamino]-
3-ethoxycarbonyl-1-carba-3-cephem-4-carboxylate The t-BOC-protected nucleus allyl ester prepared as described by Example 32 (272 mg, 0.6897 mmole) was deprotected in ethyl alcohol at 45° C. with p-toluenesulfonic acid monohydrate to provide allyl 7β-amino-3-ethoxycarbonyl-1-carba-3-cephem-4-carboxylate (203 mg). The nucleus ester was acylated as follows: the nucleus ester (203 mg, 0.6897 mmole) was dissolved in 2-3 ml of methylene chloride and the solution was cooled to 0° C. To the cold solution were added N-allyloxycarbonylphenylglycine (170.4 mg, 0.7242 mmole), pyridine (1.142 mmole, 0.092 ml) and phosphorus oxychloride (0.7587 mmole, 0.071 ml) and the solution was stirred in the cold for about 30-40 minutes. The thin layer chromatogram of the mixture showed one major spot for the product and one minor spot. The mixture was then poured into a mixture of 80 ml of ethyl acetate and 40 ml of 1N hydrochloric acid. The layers were separated and the organic layer was washed once with 40 ml of 1N hydrochloric acid, twice with 40 ml-portions of a saturated aqueous sodium bicarbonate solution, and once with 40 ml of brine. The organic layer containing the product was then dried over magnesium sulfate, filtered and evaporated under vacuum to yield 300 mg of the product as an oily solid. The product was chromatographed on 25 g of silica gel using 40% ethyl acetate/hexane for elution. The fractions containing the product were combined and evaporated under vacuum to yield 211 mg (60%) of the title compound as a white solid.

90 MHz NMR (CDCl$_3$): 1.2 (t, J=7, 3H, CO$_2$CH$_2$CH$_3$), 3.8 (dm, J=11, 1H, C$_6$H), 4.2 (q, J=7, 2H, CO$_2$CH$_2$CH$_3$), 4.6 and 4.8 (dm, J=9 Hz, 4H, CO$_2$CH$_2$CH=CH$_2$), 6.9 (broad d, J=7, 1H, amide H), and 7.3 (s, 5H, phenyl H).

EXAMPLE 34

7β-(2-Phenyl-2-aminoacetylamino)-3-ethoxycarbonyl-
1-carba-3-cephem-4-carboxylic acid To a solution of the allyloxy amino-protected allyl ester prepared as described above in Example 33 (199.2 mg, 0.3894 mmole) in 5 ml of dry acetonitrile containing 2 ml of diethyl ether were added triphenylphosphine (20.4 mg, 0.07788 mmole) and palladium diacetate (3.82 mg, 0.015576 mmole) and the mixture was allowed to stir for about 20-25 minutes. The reaction mixture was then cooled to a temperature of about 0° C. and tri-(n-butyl)tin hydride (233 mg, 0.8005 mmole) was added via syringe to the cold reaction mixture. The reaction mixture was allowed to warm to room temperature and was stirred for about 20 minutes. Concentrated hydrochloric acid (12N, 0.0667 ml) was slowly added via syringe with stirring to the reaction mixture. The product precipitated as a fine white precipitate from the yellow cloudy solution. The mixture was stirred vigorously for a few minutes and was then transferred to a 40 ml centrifuge tube with the aid of a few ml of 1:1 acetonitrile:-diethyl ether. The solid was centrigued and the mother liquor decanted. The solid product was washed, centrifuged and the supernatant decanted three times with 25 ml-portions of 1:1 acetonitrile:diethyl ether, and three times with 25 ml-portions of diethyl ether. The washed solid was dried in a vacuum oven at room temperature to yield 144 mg of the washed title compound.

The product was recrystallized as follows. The 144 mg of product was added to a 40 ml centrifuge tube and 3.3 ml of acetonitrile were added. One equivalent of 1N hydrochloric acid was added via pipette to the centrifuge tube and the tube was swirled until most of the solid went into solution. The undissolved brownish solid was centrifuged down and the supernatant solution was transferred to another 15 ml centrifuge tube. Ammonium hydroxide was added dropwise with swirling until the pH of the solution was adjusted to 4-4.5. The white product crystallized from the solution and the mixture was centrifuged and the mother liquor decanted. The solid was washed three times with 7 ml-portions of acetonitrile and once with 7 ml of diethyl ether and centrifuged after each wash with the wash being added to the mother liquor. The wash material, first crop, was dried in a vacuum oven at room temperature to provide 119.8 mg of the title compound. Upon addition of the washings to the mother liquor, a second crop of product precipitated. The second crop was washed and centrifuged by the above procedures used for the first crop to yield 16.6 mg of the title compound. Total yield equals 136.4 mg. Both crop 1 and crop 2 were greater than 97% pure via HPLC.

300 MHz NMR (D$_2$O, δ): 1.25 (t, J=7, 3H, CO$_2$CH$_2$CH$_3$), 1.0, 1.7, 2.15 and 2.55 (m, 4H, C$_1$H and C$_2$H), 3.95 (m, 1H, C$_6$H), 4.2 (q, J=7, 2H, CO$_2$CH$_2$CH$_3$), 5.2 (s, 1H, phenyl—CH—NH$_3$+), 5.4 (d, J=6, 1H, C$_7$H), 7.55 (m, 5H, phenyl H).

EXAMPLE 35

7β-[2-(2-Aminothiazol-4-yl)-2-methoxyiminoacetamido]-3-acetyl-1-carba(dethia)-3-cephem-4-carboxylic acid To a solution of 60 mg (0.1647 mmole) of allyl 7β-(t-butyloxycarbonylamino)-3-acetyl-1-carba(dethia)-3-cephem-4-carboxylate in about 5 ml of ethyl alcohol were added 32 mg (0.1679 mmole) of p-toluenesulfonic acid monohydrate and the mixture was evaporated at 45° C. in a rotary evaporator. When a thin layer chromatogram showed only one new spot (10% methyl alcohol-ethyl acetate), the residue was treated twice with 6 ml of toluene and evaporated after each treatment. The product, allyl 7β-amino-3-acetyl-1-carba(diethia)-3-cephem-4-carboxylate tosylate salt, was triturated with 3 ml of diethyl ether and dried under vacuum. There were obtained 71.5 mg of the product.

A solution of 78.2 mg (0.274 mmole) of 2-(2-allyloxycarbonylaminothiazol-4-yl)-2-methoxyiminoacetic acid in 2 ml of methylene chloride was cooled to 0° C. and 48.1 mg (0.274 mmole) of 2-chloro-4,6-dimethoxy-1,3,5-triazine and N-methylmorpholine (0.274 mmole) were added. The mixture was stirred for one hour and another equivalent of N-methylmorpholine (0.274 mmole) was added, followed by the addition of a solution of allyl 7β-amino-3-acetyl-1-carba(dethia)-3-cephem-4-carboxylate tosylate salt (obtained as described above) in 1 ml of methylene chloride. The mixture was allowed to stir for 20 hours while warming to room temperature. The reaction mixture was poured into a mixture of 75 ml of ethyl reaction and 40 ml of 1N HCl, the organic layer separated, washed successively with 40 ml of 1N HCl, twice with 35 ml portions of water, and twice with 35 ml portions of a saturated aqueous solution of sodium bicarbonate, dried over magnesium sulfate, filtered and evaporated to an oily solid residue. The residue (150 mg) was chromatographed over 10 g of silica using ethyl acetate-hexane, 60–40, v-v, and the fractions containing the product (tlc) were combined and evaporated to dryness. There were obtained 70 mg of the N-acylation product, allyl 7β-[2-(2-allyloxycarbonylaminothiazol-4-yl)-2-methoxyiminoacetamido]-3-acetyl-1-carba(diethia)-3-cephem-4-carboxylate.

NMR (90 MHz, CDCl$_3$): δ 2.3 (3H, s, acetyl CH$_3$), 5.2–5.5 (4H, m, —CH$_2$—CH=CH$_2$), 5.6–6.2 (3H, m, —CH—CH=CH$_2$ and C$_7$H), 4.7 (4H, m, —CH$_2$—CH=CH$_2$), 4.0 (4H, m, =N—OCH$_3$ and C$_8$H), 7.0 (1H, s, thiazole H), 8.0 (1H, d, J=8 Hz, amide H), 9.9 (1H, bs, amide H).

To a solution of 51 mg (0.096 mmole) of the above diblocked 3-acetyl-1-carba-3-cephem in 1 ml of methylene chloride and 1 ml of diethyl ether were added 9.95 mg (0.38 mmole) of triphenylphosphine and 1.18 mg (0.005 mmole) of palladium diacetate and the mixture was stirred for about 15 to 20 minutes. The mixture was cooled to 0° C. and tri(n-butyl)tin hydride (0.1968 mmole) was added via syringe. The mixture was allowed to warm to room temperature and was stirred for about 45 minutes. Concentrated HCl (16.4 μl) was added via syringe and a fine precipitate formed. Diethyl ether (ca. 8 ml) was added to the acidic mixture, the solid transferred to a 15 ml centrifuge tube and centrifuged. The supernatant was decanted and 8 ml of fresh diethyl ether was added and the solid again centrifuged. The process was repeated three more times and the solid dried under vacuum to yield 35 mg of the title compound of greater than 95% purity (HPLC).

NMR (300 MHz, D$_2$O): δ 1.6, 2.2, 2.4 and 2.8 (4H, m, C$_1$H and C$_2$H), 2.1 (3H, bs, acetyl CH$_3$), 4.0 (4H, m, =N—O—CH$_3$ and C$_8$H, 5.6 (1H, d, J=5 Hz, C$_7$H), 7.05 (1H, s, thiazole H).

IR (KBR) 1778 cm$^{-1}$ (β-lactam carbonyl).

M.S. 407 (M+).

EXAMPLE 36

Pivaloyloxymethyl 7β-(D-phenylglycylamino)-3-ethoxycarbonyl-1-carba(1-dethia)-3-cephem-4-carboxylate hydrochloride salt To a solution of 250 mg (0.474 mmole) of allyl 7β-[D-α-(t-butyloxycarbonylamino)phenylacetylamino]-3-ethoxycarbonyl-1-carba(1-dethia)-3-cepham-4-carboxylate in 3 ml of acetonitrile and 2 ml of diethylether were added 25 mg (0.095 mmole) of triphenylphosphine and 5.8 mg (0.0237 mmole) of palladium diacetate and the mixture was stirred for about 20 minutes. The mixture was cooled to 0° C. and 0.134 ml (0.49 mmole) of tri(n-butyl)tin hydride was added. The cooling bath was removed and while stirrin the mixture was allowed to warm to room temperature. One equivalent (0.498 ml) of 1N hydrochloric and was added to the mixture and the product, 7β-[D-α-(t-butyloxycarbonylamino)-phenylacetylamino]-3-ethoxycarbonyl-1-carba(1-dethia)-3-cephem-4-carboxylic acid, precipitated as a white solid. When the mixture was diluted with 10 ml of diethyl ether more product precipitated. The product was separated by centrifugation, washed with a mixture of diethyl ether and hexane, and dried. There were obtained 200 mg (86.9% yield) of product.

The product, 200 mg (0.410 mmole), was dissolved in 3 ml of dimethylformamide and 300 mg (1.23 mmole) of pivaloyloxymethyl iodide and 1.30 mg (0.144 mmole) of N-methylmorpholine were added to the solution. The reaction mixture was allowed to stir overnight at room temperature and then was poured into a mixture of 50 ml of ethyl acetate and 30 ml of 1N hydrochloric acid. The organic layer was separated, washed twice with 25 ml portions of 1N HCl and once with 30 ml of saturated sodium bicarbonate, dried over magnesium sulfate, filtered, and evaporated to dryness. There were obtained 240 mg of the crude pivaloyloxymethyl ester. The crude product was chromatographed over 20 g of silica, eluting with a 40:60, v:v, mixture of ethyl acetate-hexane. The fractions containing the product were combined and evaporated to yield 155 mg (63% yield) of the pivaloyloxymethyl ester.

The pivaloyloxymethyl ester was added to 4 ml of a 1:1 mixture of trifluoroacetic acid and methylene chloride and the solution was stirred at room temperature for 1 hours. The solutin was evaporated to dryness and the residue dissolved in diethyl ether. When the product precipitated, the ether was decanted and the solid was added to a mixture of chloroform and water. The pH of the mixture was adjusted to pH 7 with phosphate buffer and the chloroform layer was separated and dried over sodium sulfate. The dried chloroform layer was evaporated to dryness and the residue was dissolved in diethyl ether. An etherial solution of hydrogen chloride was added to the solution until precipitation of the salt was complete. The salt was separated and washed by centrifugation and recrystallized from methylene chloride by dilution of the solution with hexane. The recrystallized salt was washed with diethyl ether and dried. There were obtained 70 mg (62% yield) of the title compound as an off white solid.

IR (KBr) 1783 cm$^{-1}$ (β-lactam carbonyl).

NMR (360 MHz, CD$_3$CN): δ 1.2 (s, 9H, t—C$_4$H$_9$), 3.85 (m, 1H, C8H), 4.1 (m, 2H, CH$_2$CH$_3$), 5.8 (s, 2H, —CH$_2$OC(O)t-butyl), 7.4–7.6 (m, 5H, C$_6$H$_5$H).

Field Desorption Mass Spectrum: 501 M+ (—HCl), 502 M+ +1(—HCl).

EXAMPLES 37 THROUGH 82

The following compounds were prepared by removal of t-butyl ester groups of various compounds by the methods of Example 28 or 36 or removal of allyl ester groups and allyloxycarbonyl protecting groups by the method of Example 30 or 35. Biologically-labile esters in the following series were prepared using the procedure of Example 36.

| Example | R | $R^2$ | A | Spectral Data |
|---|---|---|---|---|
| | | | | Structure: 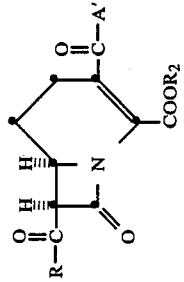 |
| 37 | 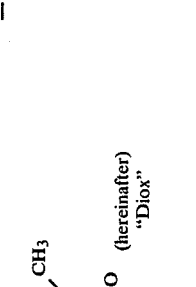 |   (hereinafter "Diox") | —O—CH₂CH₃ | 90 MHz NMR (CDCl₃, δ): 1.25, (t, J=7, 3H, —CH₂CH₃), 1.5 (s, 9H, t-Butyl), 2.2 (s, 3H, =C—CH₃), 2.9 (m, 1H, 4.0) (m, 4H, —OCH₃ and C₆H), 4.15 (q, J=7, 2H, —CH₂CH₃), 5.0 (s, 2H, —OCH₂C=), 5.5 (dd, J=5 and 6, 1H, C₇H), 7.35 (d, J=7, 1H), 8.8 (bs, 1H). |
| 38 | 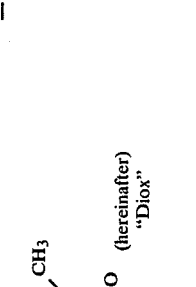 | 1-acetoxyethyl | —O—CH₂CH₃ | 90 MHz NMR (CDCl₃, δ): 1.25 + 1.3 (t, J=7, 3H, —CH₂CH₃), 1.5 (m, 12H, t-Butyl and O₂CHCH₃), 2.05 and 2.1 (s, 3H, —O₂CCH₃), 2.9 (m, 1H), 4.0 (s, 3H, —OCH₃), 4.15 and 4.2 (q, J=7, 2H, —OCH₂CH₃), 5.6 (m, 1H), 7.55 and 7.65 (d, J=7, 1H), 9.0 (bs, 1H). |
| 39 |  | Diox | —O—CH₂CH₃ | 90 MHz NMR (CDCl₃, δ): 1.2 (t, J=7, 3H, —OCH₂CH₃), 1.4 (s, 9H, t-Butyl), 2.2 (s, 3H, —C=CH₃), 2.7 (dd, J=4 and 18, 1H), 3.8 (m, 1H, C₆H, 4.1 (q, J=7, 2H, —OCH₂CH₃), 4.95 (s, 2H, —OCH₂C=), 5.1 (d, J=7, 1H), 5.3 (dd, J=5 and 7, 1H, C₇H), 5.6 (d, J=7, 1H), 6.7 (bd, J=7, 1H). |
| 40 | 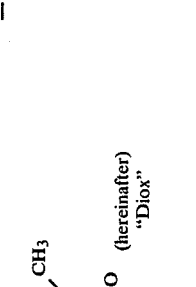 | 1-Pivaloyloxyethyl | —O—CH₂CH₃ | 90 MHz NMR (CDCl₃,δ): 1.2 (s, 9H, t-Butyl), 1.25 and 1.3 (t, J=7, 3H, —OCH₂CH₃), 1.5 (m, 15H) t-Butyl and O₂CHCH₃), 2.9 (m, 1H), 4.0 (m, 4H, —OCH₃ and C₆H), 4.2 (bq, J=7, 2H, —OCH₂CH₃), 5.6 (m, 1H, C₇H), 7.0 (m, 2H, vinyl H and O₂CHCH₃), 7.65 and 7.8 (d, J=7, 1H) 9.2 (bs, 1H). |
| 41 | 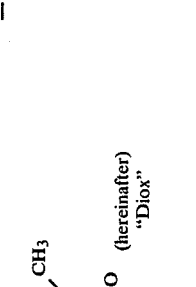 |  | —O—CH₂CH₃ | 90 MHz NMR (CDCl₃, δ): 1.0 (m, 12H), —CH(CH₃)₂) 1.3 (t, J=7, 3H, —CH₂CH₃), 1.5 (s, 9H, t-Butyl), 3.9 (m, 1H, C₆H), 4.05 (s, 3H, —OCH₃), 4.2 (bq, J=7, 2H, —CH₂CH₃), 5.55 (m, 1H, C₇H), 6.8 and 6.85 (d, J=3, 1H, —O₂CHO), 7.15 and 7.2 (s, 1H), 7.5 and 7.6 (d, J=8, 1H). |

-continued

Structure:

R-C(=O)-NH-[CH]-[CH]-N(C=O)-... with COOR₂ and C(=O)-A' groups (β-lactam/cephem core)

| Example | R | R² | A | Spectral Data |
|---|---|---|---|---|
| 42 | C(=N-OCH₃)- with thiazole ring bearing NH-t-BOC | H | -O-CH₂-C₆H₄- (phenyl) | No NMR |
| 43 | C(=N-O-CH₂-C₆H₅)- with thiazole ring bearing NH-C(CH₃)(C₆H₅)₂ (trityl-like) | H | -O-CH₂-C₆H₄- (phenyl) | No NMR |
| 44 | C(=N-OCH₃)- with thiazole ring bearing NH-t-BOC | -CH(CH₂CH₂CH₃)-O-C(=O)-O-CH(CH₃)(CH₃) | -OCH₂CH₃ | 90 MHz NMR (CDCl₃, δ): 0.9 (m, 3H), 1.25 and 1.3 (t, J=7, 3H, -OCH₂CH₃), 1.55 (s, 9H, t-Butyl), 1.6 (d, J=6, 3H, -CHCH₃), 2.9 (m, 1H), 4.0 (m, 4H, -OCH₃ and C₆H), 4.2 (bq, J=7, 2H, -OCH₂CH₃), 4.8 (m, 1H, O₂COCHCH₃), 5.6 (m, 1H, C₇H), 6.9 (m, 1H, O₂CCHO), 7.0 and 7.05 (s, 1H), 7.5 and 7.7 (d, J=8, 1H), 9.0 (bs, 1H). |
| 45 | C(=N-OCH₃)- with thiazole ring bearing NH-t-BOC | 1-pivaloyloxyethyl | -O-CH₂-C₆H₄- (phenyl) | 90 MHz NMR (CDCl₃, δ): 1.20 (s, 9H, -t-Butyl), 1.4 (t, J=7, 3H, -OCH₂CH₃), 1.5 (m, 12H, t-Butyl and CHCH₃), 2.9 (m, 1H), 4.0 (m, 4H, -OCH₃ and C₆H), 4.1 (q, J=7, 2H, -OCH₂CH₃), 5.1 (m, 2H, -OCH₂ϕ), 5.5 (m, 1H, C₇H), 6.8 (m, 1H, O₂CCHO) 7.05 + 7.1 (s, 1H), 7.3 (s, 5H, -C₆H₅), 7.5 (d, J=7, 1H). |

-continued
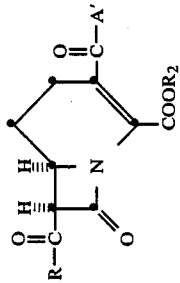
| Example | R | R² | A | Spectral Data |
|---|---|---|---|---|
| 46 | N=C(NH-t-BOC)-S-C(=N-O-CH₂-CH(NH-t-BOC)) | -CH(CH₃)OC(O)OCH₂CH(CH₃)₂ | —OCH₂CH₃ | 300 MHz NMR (CDCl₃, δ): 1.0 (m, 12H, —CHCH₃), 1.3 (m, 12H, —CH₂CH₃ and t-Butyl) 2.9 (m, 1H), 3.4 (m, 2H, —CH₂CH₂N), 3.95 (m, 1H, C₆H), 4.25 (m, 2H, —CH₂CH₃), 4.4 (m, 2H, —OCH₂CH₂N), 5.0 (m, 1H, C₇H), 6.6 (s, 1H), 5.6 (m, 1H), —OCHO), 7.05 (bs, 1H), 7.3 (s, 15H, C₆H₅), 8.2 (bs, 1H). |
| 47 | N=C(NH-C(C₆H₅)₃)-S-C(=N-O-CH₂-COOCH₂-) | H | —OCH₂CH₃ | No NMR |
| 48 | N=C(NH-C(C₆H₅)₃)-S-C(=N-O-CH₂-C₆H₅) | H | —OCH₂CH₃ | No NMR |

-continued

| Example | R | R² | A | Spectral Data |
|---|---|---|---|---|
| 49 | (oxime with -CH₂-C₆H₄-Cl; aminothiazole ring ×3) | H | —OCH₂CH₃ | No NMR |
| 50 | (oxime with OCH₃; aminothiazole with t-BOC) | H | —O—CH₂CH₂CH₂CH₃ | No NMR |
| 51 | (oxime with —O—CH₂—CH₂—NH—t-BOC; aminothiazole ×3) | H | —O—CH₂CH₃ | No NMR |

-continued

General structure shown at top of table:
R-C(=O)-NH-[β-lactam ring with H,H stereochemistry]-N-CH=C(COOR₂)-CH₂-C(=O)-A'

| Example | R | R² | A | Spectral Data |
|---|---|---|---|---|
| 52 | C₆H₅-CH(NH₂)- | H | —OH | 300 MHz NMR (D₂O, δ): 1.05 (m, 1H), 1.65 (m, 1H), 2.2 (m, 1H), 2.5 (dd, J=4 and 19, 1H) 3.9 (m, 1H, C₆H), 5.2 (s, 1H), 5.4 (d, J=6, 1H, C₇H), 7.5 (m, 5H, C₆H₅). IR (KBr): 1762 cm⁻¹ β-lactam. |
| 53 | C₆H₅-CH(NH₂)- | H | -O-CH₂-(p-C₆H₄)- | 300 MHz NMR (D₂O, δ): 1.05 and 1.6 2.1 and 2.5 (m, 4H, C₁H + C₂H), 3.9 (m, 1H, C₆H), 5.2 (m, 2H, CH₂φ), 5.4 (d, J=6, 1H, C₇H), 7.4 (bs, 5H, C₆H₅), 7.5 (bs, 5H, C₆H₅) IR (KBR): 1772 cm⁻¹ β-lactam Mass Spec: 450 (m⁺+1). |
| 54 | (2-thienyl)-CH(NH₂)- | H | —OCH₃ | 300 MHz NMR (D₂O, δ): 0.9, 1.45, 2.1, and 2.45 (m, 4H, C₁H and C₂H), 3.7 (s, 3H, —OCH₃), 3.9 (m, 1H, C₆H), 5.45 (d, J=5, 1H, C₇H), 5.65 (s, 1H), 7.55, 7.9, 7.95 and 8.1 (m, 5H, ArH), IR (KBr): 1778 cm⁻¹ (β-lactam), Mass Spec: 430 (m⁺+1). |
| 55 | C₆H₅-CH(NH₂)- | H | —OCH₂CH₂CH₂CH₃ | 300 MHz NMR (D₂O, δ): 0.9, 1.4, 1.6, and 4.1 (t, m, m, q; J=6; 3H, 2H, 2H; H₃CCH₂CH₂CH₂O, respectively; 1.05, 1.7, 2.15 and 2.55 (m, 4H, C₁H and C₂H), 3.9 (m, 1H, C₆H), 5.2 (s, 1H), 5.4 (d, J=6, 1H, C₇H), 7.55 (m, 5H, C₆H₅) IR (KBr): 1776 cm⁻¹; Mass spec: 416 (m⁺+1) |
| 56 | C₆H₅-CH(NH₂)- | H | CH₃ | 300 MHz NMR (D₂O, δ): 1.05, 1.70, 2.2 and 2.6 (m, 4H, C₁H and C₂H), 2.30 (s, 3H, —CH₃), 3.95 (m, 1H, C₆H), 5.2 (s, 1H), 5.45 (d, J=6, 1H, C₇H), 7.5 (bm, 5H, C₆H₅) IR (KBr): 1775 cm⁻¹ (β-lactam) Mass Spec: 358 (m⁺+1). |
| 57 | (2-amino-thiazol-4-yl)-C(=N-OCH₃)- | H | —OCH₂CH₃ | 300 MHz NMR (D₂O, δ): 1.3 (t, J=7, 3H, —OCH₂CH₃) 1.6, 2.15, 2.35 and 2.8 (m, 4H, C₁ and C₂), 4.1 (m, 4H, —OCH₃ and C₆H), 4.2 (q; J=7, 2H, —OCH₂CH₃), 5.55 (d, J=5, 1H, C₇H), 7.1 (s, 1H) IR (KBr): 1779 cm⁻¹ (β-lactam) Mass Spec: 438 (m⁺). |

-continued

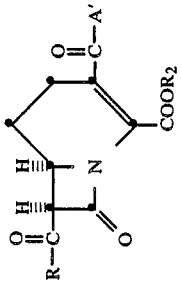

| Example | R | R² | A | Spectral Data |
|---------|---|-----|---|---------------|
| 58 | N≡C(NH₂)S-C(=N-OCH₃)- | Diox | —OCH₂CH₃ | 90 MHz NMR (CDCl₃, δ): 1.3 (t, J=7, 3H, —OCH₂CH₃), 2.2 (s, 3H, =C—CH₃), 2.9 (m, 1H), 3.95 (m, 4H, —OCH₃ and C₆H), 4.1 (q, J=7, 2H, —OCH₂CH₃), 5.0 (s, 2H, O₂C₂CH₂C=), 5.4 (bs, 2H), 5.7 (dd, J=5 and 8, 1H, C₇H), 6.6 (s, 1H), 8.3 (d, J=8, 1H). |
| 59 | N≡C(NH₂)S-C(=N-OCH₃)- | 1-Acetoxyethyl | —OCH₂CH₃ | 90 MHz NMR (CDCl₃, δ): 1.25 (bt, J=7, 3H, —CH₂CH₃), 1.5 (d, J=6, 3H, —CHCH₃), 2.1 (s, 3H, —COCH₃), 2.8 (m, 1H), 3.95 (m, 4H, —OCH₂ and C₆H), 4.2 (bq, J=7, 2H, —OCH₂CH₃), 5.5 (bs, 2H), 5.6 (dd, J=5 and 8, 1H, C₇H), 6.7 (s, 1H, 7.0 (m, 1H, CO₂CHCH₃), 8.15 and 8.2 (d, J=8 1H. IR (CHCl₃): 1774 cm⁻¹ (β-lactam) Mass Spec: 523 (m⁺). |
| 60 | 4-NH₂-CH-C₆H₄- | Diox | —OCH₂CH₃ | 300 MHz NMR (CDCl₃, δ): 1.20 (t, J=7, 3H, —CH₂CH₃), 2.1 (s, 3H, =C—CH₃), 2.6 (m, 1H), 3.8 (m, 1H, C₆H), 4.1 (m, 2H, —CH₂CH₃), 8.6 (bd, J=8, 1H). IR (CHCl₃): 1769 cm⁻¹ (β-lactam) Mass Spec: 500 (m⁺ – HCl). |
| 61 | N≡C(NH₂)S-C(=N-OCH₃)- | 1-pivaloyloxyethyl | —OCH₂CH₃ | 90 MHz NMR (CDCl₃, δ): 1.2 (s, 9H, t-Butyl), 1.25 and 1.3 (t, J=7, 3H, —CH₂CH₃), 1.5 and 1.55 (d, J=6, 3H, —CHCH₃), 2.8 (m, 1H), 3.95 (m, 4H, —OCH₃ and C₆H), 4.1 (q, J=7, 2H, —OCH₂CH₃), 5.4 (bs, 1H), 5.6 (dd, J=5 and 8, 1H, C₇H), 6.6 (s, 1H), 6.9 (m, 1H, CO₂CHCH₃), 8.1 and 8.15 (d, J=8, 1H). IR (KBr): 1785 cm⁻¹ (β-lactam) Mass Spec: 565 (m⁺). |
| 62 | N≡C(NH₂)S-C(=N-OCH₃)- | O=C-O-CH(CH(CH₃)₂)-CH₂-CH(CH₃)₂ | —OCH₂CH₃ | 300 MHz NMR (CDCl₃, δ): 1.0 (m, 12H, —OCH₂CH₃), 2.85 (dd, J=4 and 18, 1H), 4.0 (m, 4H, —OCH₃ and C₆H), 4.2 (m, 2H, —OCH₂CH₃), 5.35 (bs, 2H), 5.65 (m, 1H, C₇H), 6.78 and 6.80 (s, 2H), 6.85 and 6.9 (d, J=6, 1H, CO₂CHCH₂), 7.85 (m, 1H). IR (CHCl₃): 1773 cm⁻¹ (β-lactam) Mass Spec: 593 (m⁺). |

-continued

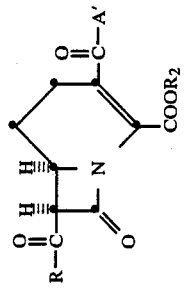

| Example | R | R² | A | Spectral Data |
|---|---|---|---|---|
| 63 | (aminothiazole C=N-OCH₃ group) | H | -O-CH₂-φ | 300 MHz NMR (D₆-DMSO, δ): 1.55, 1.9, 2.25 and 2.7 (m, 4H, C₁H and C₂H), 3.8 (s, 3H, -OCH₃), 3.9 (m, 1H, C₆H), 5.1 (AB, J=12, 2H, -CH₂φ), 5.5 (dd, J=5 and 8, 1H, C₇H), 6.8 (s, 1H), 7.2 (bs, 2H), 7.4 (bs, 5H, C₆H₅), 9.3 (d, J=8, 1H). IR (KBr): 1773 cm⁻¹ (β-lactam). Mass Spec: 500 (m⁺+1). |
| 64 | (aminothiazole C=N-O-CH₂-phenyl group) | H | -O-CH₂-φ | 300 MHz NMR (D₆-DMSO, δ): 1.4, 1.6, 2.1, and 2.5 (m, 4H, C₁H and C₂H), 3.85 (m, 1H, C₆H), 5.1 (s, 2H, -CH₂φ), 5.1 (AB, J=12, 2H, -CH₂φ), 6.8 (s, 1H), 7.2 (bs, 2H), 7.35 (bm, 10H, C₆H₅), 9.4 (d, J=8, 1H), 5.5 (dd, J=5 and 8, 1H, C₇H). IR (KBr): 1774 cm⁻¹ (β-lactam). Mass Spec: 577 (m⁺+1). |
| 65 | (aminothiazole C=N-OCH₃ group) | -CH(CH₃)-O-C(=O)-O-CH(CH₃)-CH₂CH₂CH₃ | -OCH₂-CH₃ | 300 MHz NMR (CDCl₃, δ): 0.9, (bt, J=7, 3H, -CH₂CH₂CH₃), 2.2, 2.35 and 2.89 (m, 3H, CHCH₂H), 4.0 (m, 4H, -OCH₃ and C₆H), 4.2 (m, 2H, -OCH₂CH₃), 4.8 (m, 1H, O₂COCHCC), 5.4 (bs, 2H), 5.7 (m, 1H, C₇H), 6.85 (s, 1H), 6.95 (m, 1H, -CO₂CHO), 8.0 (bs, 1H). IR (CHCl₃): 1772 cm⁻¹ (β-lactam). Mass Spec: 595 (m⁺). |

-continued

| Example | R | R² | A | Spectral Data |
|---------|---|----|----|---------------|
| 66 | (4-D-phenyl)-CH(NH-)-C(=O)-N[ring with N-CH₂-CH₃ and two C=O groups] | H | —OCH₂—CH₃ | 300 MHz NMR (DMSO, δ): 1.1 (m, 3H, —NCH₂C$\underline{H}_3$), 2.35 (m, 1H), 5.2 (dd, J=5 + 8, 1H, C₁H), 5.55 (d, J=9, 1H) 7.4 (m, 5H, C₆H₅), 9.3 (bs, 1H), 9.85 (d, J=8, 1H). |
| 67 | [2-aminothiazol-4-yl]-C(=N-OCH₃)— | 1-pivaloyloxyethyl | [phenyl-OCH₂-] | 300 MHz NMR (CDCl₃, δ): 1.2 (s, 9H, t-butyl), 1.4 (m, 3H, —CHC$\underline{H}_3$), 1.7, 2.2, 2.4 and 2.9 (m, 4H, C₁H and C₂H), 4.0 (m, 4H, —OC$\underline{H}_3$ and C₆H), 5.4 (bs, 2H) 5.7 (m, 1H, C₇H), 6.8 (s, 1H, —OCH$_2$CHO), 7.4 (bs, 5H, C₆H₅), 8.0 (m, 1H), 5.2 (m, 2H, C$\underline{H}_2$φ). Mass Spec: 627 (m⁺). |
| 68 | [2-aminothiazol-4-yl]-C(=N-O-CH₂CH₂NH₂)— | —C(=O)—CH₂—CH(CH₃)₂ on —O—CH(CH(CH₃)₂)— | —OCH₂CH₃ | |
| 69 | [2-aminothiazol-4-yl]-C(=N-N(CH₂-CO₂H))— | H | —OCH₂CH₃ | 300 MHz NMR (D₆-DMSO, δ): 1.55, 1.95, 2.25 and 2.65 (m, 4H, C₁H and C₂H), 1.2 (t, J=7, 3H, —OCH₂C$\underline{H}_3$), 3.9 (m, 1H, C₇H), 4.1 (q, J=7, 2H, —OC$\underline{H}_2$CH₃), 4.6 (s, 2H, OC$\underline{H}_2$CO₂), 5.55, (dd, J=5, 8, 1H, C₇H), 6.8 (s, 1H, C$\underline{H}_2$CO₂), 7.2 (bs, 2H), 9.4 (d, J=8, 1H). IR (KBr): 1778 cm⁻¹ (β-lactam) Mass Spec: 482 (m⁺ + 1). |

-continued

| Example | R | R² | A | Spectral Data |
|---|---|---|---|---|
| 70 | aminothiazole-C(=N-O-CH₂-C₆H₅)- | H | —O—CH₂CH₃ | 300 MHz NMR (D₆-DMSO, δ): 1.2 (t, J=7, 3H, —CH₂CH₃), 1.45, 1.65, 2.1, 2.45 (m, 4H, C₁H and C₂H), 3.8 (m, 1H, C₆H), 4.1 (m, 2H, —OCH₂CH₃), 5.15 (s, 2H, —CH₂φ), 5.4 (dd, J=5 and 8, 1H, C₇H), 6.8 (s, 1H), 7.2 (bs, 2H), 7.3 (m, 5H, C₆H₅), 9.4 (d, J=8, 1H). IR (KBr): 1769 cm⁻¹ (β-lactam) |
| 71 | aminothiazole-C(=N-O-CH₂-C₆H₄-Cl)- | H | —O—CH₂CH₃ | 300 MHz NMR (D₆-DMSO, δ): 1.2 (t, J=7, 3H, —OCH₂CH₃), 1.4, 1.65, 2.15 and 2.5 (m, 4H, C₁H and C₂H), 3.85 (m, 1H, C₆H), 4.1 (q, J=7, 2H, —OCH₂CH₃), 5.15 (s, 2H, —CH₂Ar), 5.5 (dd, J=5 and 9, 1H, C₇H), 6.8 (s, 1H), 7.2 (bs, 1H), 7.4 (bs, 4H, C₆H₄), 9.4 (d, J=9, 1H) IR (KBr): 1773 cm⁻¹ (β-lactam) Mass Spec: 548 (m⁺). |
| 72 | aminothiazole-C(=N-OCH₃)- | H | —O—CH₂CH₂CH₂CH₃ | 300 MHz NMR (DMSO-D₆, δ): 0.85 (t, J=7, 3H, —CCCH₃), 1.35 (m, 2H, CCH₂CH₃), 1.55 (m, 2H, —CCH₂CC), 1.55, 1.85, 2.2 and 2.6 (m, 4H, C₁H and C₂H), 3.8 (m, 4H, OCH₃ and C₆H, 4.0 (m, 2H, —OCH₂CCC)), 5.4 (dd, J=5 and 8, 1H, C₇H), 6.85 (s, 1H), 7.2 (s, 2H), 9.3 (d, J=8, 1H). Mass Spec: 466 (m⁺+1). |

-continued

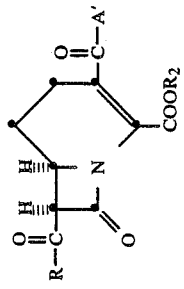

| Example | R | R² | A | Spectral Data |
|---|---|---|---|---|
| 73 | N≡C(H₂N)S—C(=N—OCH₂CH₂NH₂)— | H | —OCH₂CH₃ | 300 MHz NMR (DMSO-D₆, δ): 1.15, (m, 3H, —OCH₂CH₃), 1.5, 1.9, 2.15 and 2.7 (m, 4H, C₁H and C₂H), 3.9 (m, 1H, C₆H), 4.05 (m, 2H, OCH₂CH₃), 4.25 (m, 2H, —OCH₂CH₃) 3.15 (m, 2H, —OCH₂CH₂N), 5.5 (m, 1H, C₇H), 6.85 (s, 1H). IR (KBr): 1769 cm⁻¹ (β-lactam) Mass Spec: 467 (m⁺). |
| 74 | N≡C(H₂N)S—C(=N—OCH₂CH₂Cl)— | H | —OCH₃ | 300 MHz NMR (DMSO-D₆, δ): 1.55, 1.85, 2.15 and 2.55 (m, 4H, C₁H and C₂H), 3.55 (s, 3H, —OCH₃), 3.8 (m, 3H, C₆H and OCH₂CH₂Cl), 4.3 (t, J=6, 2H, —O—CH₂CH₂Cl), 5.4 (dd, J=5 and 8, 1H, C₇H), 6.8 (s, 1H), 7.2 (bs, 2H), 9.35 (d, J=8, 1H). IR (KBr): 1769 cm⁻¹ (β-lactam carbonyl) |
| 75 | N≡C(H₂N)S—C(=N—O—C₄H₉ₙ)— | H | —O—CH₂CH₃ | 300 MHz NMR (DMSO-D₆, δ): 0.9 (t, J=7, 3H, —CH₂CH₂CH₂CH₃), 1.2 (t, J=7, 3H, O—C—CH₃), 1.35 (m, 2H, —C—C—CH₂—CH₃), 1.6 (m, 2H, —C—CH₂—C—C), 1.6, 1.85, 2.25 and 2.65 (m, 4H, C₁H and C₂H), 3.9 (m, 1H, C₆H), 4.1 (m, 4H, —OCH₂CH₃ and O—CH₂CH₃), 5.5 (dd, J=5 and 8, 1H, C₇H), 6.89 (s, 1H), 7.2 (s, 2H), 9.3 (d, J=8, 1H), 13.5 (bs, 1H). IR (KBr): 1775 cm⁻¹ (β-lactam) Mass Spec: 480 (M⁺). |
| 76 | N≡C(H₂N)S—C(=N—OCH₃)— | H | —O—CH₂CH₂CH₃ | 300 MHz NMR (DMSO-D₆, δ): 0.90 (t, J=7, 3H, —CCCH₃), 1.55 (m, 2H, —C—CH₂—CH₃), 1.55, 1.85, 2.2 and 2.6 (m, 4H, C₁H and C₂H), 3.85 (m, 4H, OCH₃ and C₆H), 3.95 (m, 2H, —O—CH₂—C—C), 5.45 (m, 1H, C₇H), 6.8 (s, 1H), 7.2 (bs, 2H), 9.3 (d, J=8, 1H). IR (KBr): 1776 cm⁻¹ (β-lactam) Mass Spec: 452 (M⁺). |
| 77 | N≡C(H₂N)S—C(=N—OCH₃)— | H | —O—CH₂CH(CH₃)₂ | 300 MHz NMR (DMSO-D₆, δ): 0.95 (d, J=7, 6H, OCC(CH₃)₂), 1.85 (m, 1H, O—C—CH(CH₃)₂), 1.55, 1.9, 2.25 and 2.7 (m, 4H, C₁H and C₂H), 3.8 (m, 5H, OCH₃ and OCH₂CH(CH₃)₂), 3.9 (m, 1H, C₆H), 5.5 (dd, J=5 and 9, 1H, C₇H), 6.8 (s, 1H), 7.2 (bs, 2H), 9.35 (d, J=9, 1H), 13.6 (bs, 1H). IR (KBr): 1773 cm⁻¹ (β-lactam) Mass Spec: 466 cm¹. |

-continued

Structure:

$$R-C(=O)-NH-[\beta\text{-lactam with }CH_2\text{ linked to }C(COOR_2)=CH-C(=O)-A']$$

| Example | R | $R^2$ | A | Spectral Data |
|---------|---|-------|---|---------------|
| 78 | (aminothiazolyl)-C(=N-O-CH$_2$CH$_3$)- | H | —OCH$_3$ | 300 MHz NMR (DMSO-D$_6$, δ): 1.2 (t, J=7, 3H, —CCH$_3$), 1.55, 1.9, 2.25 and 2.65 (m, 4H, C$_1$H and C$_2$H), 3.6 (s, 3H, —OCH$_3$), 3.91 (m, 1H, C$_6$H), 4.1 (q, J=7, 2H, —OCH$_2$CH$_3$), 5.5 (dd, J=6 and 9, 1H, C$_6$H), 6.75 (s, 1H), 7.25 (bs, 2H), 9.3 (d, J=9, 1H), 13.6 (bs, 1H). IR (KBr): 1776 cm$^{-1}$, (β-lactam) Mass Spec: 438 (M$^+$). |
| 79 | (aminothiazolyl)-C(=N-O-CH$_2$CH=CH$_2$)- | H | —OCH$_3$ | 300 MHz NMR (DMSO-D$_6$, δ): 1.55, 1.9, 2.25 and 2.65 (m, 4H, C$_1$H and C$_2$H), 3.6 (s, 3H, —OCH$_3$), 3.9 (m, 1H, C$_6$H), 4.6 (d, J=5, 2H, —OCH$_2$CH=CH$_2$), 5.2 and 5.35 (m, 2H, —C=C=CH$_2$), 5.5 (dd, J=5 and 9, 1H, C$_7$H), 5.95 (m, 1H, —CH$_2$—CH=CH$_2$), 6.75 (s, 1H), 7.2 (s, 2H), 9.35 (d, J=9, 1H). IR (KBr): 1776 cm$^{-1}$ (β-lactam) Mass Spec: 450 (m$^+$). |
| 80 | (aminothiazolyl)-C(=N-OCH$_3$)- | H | —O(CH$_2$)$_5$CH$_3$ | No NMR. |
| 81 | (aminothiazolyl)-C(=N-OCH$_3$)- | H | —OCH(CH$_3$)$_2$ | 300 MHz NMR (DMSO-D$_6$, δ): 1.18 (d, J=6, 3H, —CHCH$_3$), 1.20 (d, J=6, 3H, —CH—CH$_3$), 1.55, 1.9, 2.25 and 2.65 (m, 4H, C$_1$H and C$_2$H), 3.8 (s, 3H, —OCH$_3$), 3.9 (m, 1H, C$_6$H), 4.9 (heptet, J=6, 1H, —CH(CH$_3$)$_2$), 5.5 (dd, J=5 and 8, 1H, C$_7$H), 6.8 (s, 1H), 7.2 (s, 2H), 9.3 (d, J=8, 1H), 13.5 (bs, 1H). |
| 82 | (aminothiazolyl)-C(=N-OCH$_3$)- | H | OH | 300 MHz NMR (DMSO-D$_6$, δ): 1.5, 1.85, 2.3 and 2.55 (m, 4H, C$_1$H and C$_2$H), 3.8 (m, C$_6$H), 3.85 (s, 3H, —OCH$_3$), 5.4 (dd, J=5 and 8, 1H, C$_7$H), 6.8 (s, 1H), 7.2 (s, 2H), 9.25 (d, J=8, 1H). |

EXAMPLE 83

Allyl 7β-t-butyloxycarbonylamino-3-phenylthioacetyl-1-carba-3-cephem-4-carboxylate Allyl 7β-t-butyloxycarbonylamino-3-acetyl-1-carba-3-cephem-4-carboxylate was prepared by a synthesis analogous to that in Example 31, while substituting allyl-3-phenylsulfinyl-4-oxopent-2-enoate for the corresponding t-butyl ester in order to provide the desired allyl ester at the 4-position of the carbacephem nucleus.

To a dry solution of allyl-7β-t-butyloxycarbonylamino-3-acetyl-1-carba-3-cephem-4-carboxylate (113 mg, 0.310 mMol, in 1.5 ml CH$_2$Cl$_2$) at 0° C. was added 22 μl (0.357 mMol) of 2,6-lutidine. This solution was then treated with t-butyldimethylsilyl triflate (75 μl, 0.326 mMol) and allowed to warm to room temperature with continued stirring for approximately 30 minutes. The crude reaction mixture was diluted with 40 ml of CH$_2$Cl$_2$ and extracted with cold NaHCO$_3$ solution. The CH$_2$Cl$_2$ layer was then dried over anhydrous Na$_2$SO$_4$, filtered, and concentrated under reduced pressure to provide an oil. The crude product was then chromatographed on 5 g (AlO$_2$) using (20/80) ethylacetate/hexane (250 ml total+5 drops of pyridine) as the eluent to provide 35.6 mg of allyl 7β-t-butyloxycarbonylamino-3-(1-hydroxyethen-1-yl-O-t-butyldimethylsilyl ether)-1-carba-3-cephem-4-carboxylate.

90 MHz NMR (CDCl$_3$, δ): 0.2 (s, 6H, Si cH$_3$), 0.9 (s, 9H, Si t-butyl), 1.4 (s, 9H, t-Butyl-O), 2.75 (m, 1H), 3.8 (m, 1H, C$_6$H), 4.3 (bs, 2H,

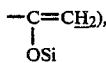

4.7 (dm, J=4, 2H, —OCH$_2$CH).

To 16 mg (0.0334 mMol) of the silyl enol ether prepared above, in 1 ml of THF, was added 6.3 mg of N-bromosuccinimide. After approximately 15 minutes, the crude product was concentrated under reduced pressure and chromatographed on silica gel (5 g) using ethylacetate/hexane (35%/65%) as eluent to provide 4.5 mg (30%) of allyl-7β-t-butyloxycarbonylamino-3-bromoacetyl-1-carba-3-cephem-4-carboxylate.

90 MHz NMR (CDCl$_3$, δ): 1.4 (s, 9H, t-Butyl), 2.85 (m, 1H), 3.8 (m, 1H, C$_6$H), 4.0 (m, 2H, —CH$_2$Br), 4.7 (dm, J=5, 2 H, —OCH$_2$CH), 5.7-6.2 (m, 1H, —CH$_2$CH=CH$_2$).

To 0.7 ml of CH$_2$Cl$_2$ was added 4.3 mg of allyl-7β-t-butyloxycarbonylamino-3-bromoacetyl-1-carba-3-cephem-4-carboxylate. To this solution was added 1.2 μl (0.0107 mMol) of n-methyl morpholine followed by 1.04 μl (0.0102 mMol) of thiophenol. After stirring for 30 minutes, the reaction mixture was allowed to warm to room temperature. The reaction mixture was then diluted with 25 ml of CH$_2$Cl$_2$ and extracted once with an aqueous NaHCO$_3$ solution and twice with 10 ml of 1N HCl solution. The CH$_2$Cl$_2$ layer was then dried over anhydrous MgSO$_4$, filtered, and concentrated under reduced pressure to yield the title compound as a yellow oil (4.7 mg~100% yield).

90 MHz NMR (CDCl$_3$, δ): 1.4 (s, 9H, t-Butyl), 2.7 (m, 1H), 3.9 (m, 1H), 3.85 (s, 2H, —CH$_2$Sφ), 4.7 (dm, J=5, 2H, —OCH$_2$CH), 7.2 (m, 5H, —SC$_6$H$_5$).

EXAMPLE 84 t-Butyl 7β-Butyloxycarbonylamino-3-carboxyl-1-carba-3-cephem-4-carboxylate

To 700 mg (1.657 mMol) of 4-t-butyl 7β-t-butyloxycarbonylamino-3-allyloxycarbonyl-1-carba-3-cephem-4-carboxylate, dissolved in 12 ml of (1:1) CH$_3$CN/(CH$_3$CH$_2$)$_2$O, was added 174 mg (0.663 mMol) of triphenylphosphine and 20.34 mg (0.0829 mMol) of Pd

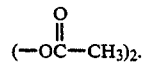

The reaction mixture was stirred for approximately 20 minutes and then cooled to 0° C. and treated with 0.464 ml (1.724 mMol) of (CH$_3$CH$_2$CH$_2$CH$_2$)$_3$SnH. The reaction mixture was then allowed to cool and stirring was continued for 50 minutes. The crude reaction mixture was then treated with 1N HCl. This mixture was then poured into 100 ml of CHCl$_3$ and 25 ml of H$_2$O. The organic layer was separated, dried over anhydrous MgSO$_4$, filtered, and concentrated under reduced pressure to provide an oily solid. The crude product was recrystallized from CH$_2$Cl$_2$/hexane to yield 570 mg (90%) of the title compound.

EXAMPLE 85 t-Butyl 7β-butyloxycarbonyl-3-phenylaminocarbonyl-1-carba-3-cephem-4-carboxylate To the compound prepared in Example 75, was added 4 ml of CH$_2$Cl$_2$. The resulting solution was cooled to −5° C. and treated with 69 mg (0.393 mMol) of 1-chloro-2,4-dimethoxytriazine (see Dudley, et. al., *J. Am. Chem. Soc.*, Vol. 73, p. 2986 (1956), for preparation of this reagent; see also, *Tetrahedron Letters*, Vol. 26, p. 2901 (1985)) and 43.5 μl (0.395 mMol) of n-methylmorpholine. The reaction mixture was then treated with 35.5 μl (36.3 mg, 0.39 mMol) of aniline and the reaction was allowed to warm to room temperature and stirred for 4 h. The crude reaction mixture was then poured into a 75 ml (CH$_3$CH$_2$)$_2$O/30 ml 1N HCl mixture. The organic phase was separated and extracted sequentially with 30 ml 1N HCl, 30 ml H$_2$O, and 30 ml of saturated NaHCO$_3$ solution. The organic phase was then dried over anhydrous MgSO$_4$, filtered, and concentrated under reduced pressure. The crude product was chromatographed on 15 g of silica using (50/50) ethyl acetate/hexane as eluent to provide 115 mg of the title compound.

90 MHz NMR (CDCl$_3$, δ): 1.4 (s, 18H, t-Butyl), 3.8 (m, 1H, C$_6$H), 5.3 (m, 1H), 5.9 (d, J=8, 1H), 8.5 (bs, 1H).

The title compound was then deprotected and N-acylated with 2-[2-(allyloxycarbonylamino)thiazol-4-yl]-2-methoxyiminoacetyl chloride as in Examples 29 and 35, to provide t-butyl 7β-[[2-(2-allyloxycarbonylamino)thiazol-4-yl]-2-methoxyiminoacetamido]-3-phenylaminocarbonyl-1-carba-3-cephem-4-carboxylate.

90 MHz NMR (CDCl$_3$, δ): 1.4 (s, 9H, t-butyl), 3.9 (s, 3H, OCH$_3$), 3.95 (m, 1H, C$_6$H), 4.7 (dm, J=6, 2H, OCH$_2$CH), 5.7 (dd, J=4 and 8, 1H, C$_7$H), 8.2 (d, J=8, 1H), 8.3 (bs, 1H).

The compound prepared above was deesterified as in Example 28 to provide the amino-protected free acid. The acid was treated with bis-trimethylsilyltrifluoroacetamide to form the silyl ester (for physical characterization).

90 MHz NMR (CDCl$_3$, δ): 0.3 (s, 9H, —Si(CH$_3$)$_3$), 2.7 (m, 1H), 3.8 (s, 3H, —OCH$_3$), 3.9 (m, 1H, C$_6$H), 4.65 (d, J=5, 2H, —OCH$_2$—CH), 7.2 (s, 1H), 8.2 (d, J=7, 1H), 8.8 (s, 1H).

The amino group of the above acid was deprotected as in Example 35 to provide 7β-[2-(2-aminothiazol-4-yl)-2-methoxyiminoacetamido]-3-phenylaminocarbonyl-1-carba-3-cephem-4-carboxylic acid.

IR (KBr): 1776 cm$^{-1}$ (β-lactam C=O).
MS: 484 (M+).

EXAMPLE 86

Benzhydryl 7β-allyloxycarbonylamino-7α-methoxy-3-ethoxycarbonyl-1-carba-3-cephem-4-carboxylate (A) To a 494 mg (1.253 mMol) sample of 3-ethyl-4-allyl-7β-butyloxycarbonylamino-1-carba-3-cephem-3,4-dicarboxylate was added approximately 10 ml of ethanol and 241.6 mg of p-toluenesulfonic acid monohydrate. The resulting mixture was then concentrated under reduced pressure at 45° C. An additional 8 ml of ethanol was added and the mixture concentrated to dryness. The resulting tosylate salt was then dissolved in approximately 6 ml of CH$_2$Cl$_2$ and treated with 266.1 mg (3.631 mMol) of n-methyl morpholine and 353.5 mg (0.211 ml, 1.253 mMol) of trifluoromethanesulfonic anhydride and stirred for 30 minutes. The crude product mixture was then poured into a 100 ml CH$_2$Cl$_2$/40 ml saturated NaHCO$_3$ solution. The organic phase was then separated and extracted once with 40 ml of saturated aqueous NaHCO$_3$ and twice with 40 ml of 1N HCl. The organic phase was then dried over anhydrous MgSO$_4$, filtered, and concentrated under reduced pressure to provide 433 mg (81% yield) of 3-ethyl-4-allyl-7β-trifluoro(methanesulfonylamino)-1-carba-3-cephem-3,4-dicarboxylate as a white crystalline solid.

90 MHz NMR (CDCl$_3$, δ): 1.25 (t, J=7, 3H, —OCH$_2$CH$_3$), 1.69 (m, 1H), 2.9 (m, 1H), 3.9 (m, 1H), C$_6$H), 4.15 (q, J=7, 2H, —OCH$_2$CH$_3$), 4.6 (bs, 1H, 4.7 (dm, J=6H, 2H, —OCH$_2$CH), 5.05 (d, J=4, 1H, C$_7$H), 5.8 (m, 1H, CH=CH$_2$).

(B) to a 380 mg (0.891 mMol) sample of the compound provided above in part A, was added 5 ml of CH$_3$CN, 3 ml of (CH$_3$CH$_2$)$_2$O, 70 mg (0.267 mMol) of triphenylphosphine, and 10 mg (0.045 mMol) of

After stirring for 5 minutes, 0.30 ml (1.11 mMol) of (CH$_3$CH$_2$CH$_2$CH$_2$)$_3$SnH was added and stirring was continued for 20 minutes. The reaction mixture was then treated with an additional 0.27 ml of (CH$_3$CH$_2$CH$_2$CH$_2$)$_3$SnH and stirred for 10 minutes. The reaction mixture was then treated with 12N HCl and concentrated under reduced pressure. The crude product was treated with 15 ml (CH$_3$CH$_2$)$_2$O and 15 ml of hexane. The resulting mixture was centrifuged and the mother liquors decanted off. The solid was washed twice with (1:1) (CH$_3$CH$_2$)$_2$O/hexane and dried under reduced pressure to yield 340 mg (99% yield) of 3-ethoxycarbonyl-7β-trifluoromethanesulfonylamino-1-carba-3-cephem-4-carboxylic acid.

(C) To 391 mg (1.012 mMol) of the acid produced in part B, above, was added 10 ml of CH$_3$CN and diphenyl diazomethane in 3 portions: 157 mg, 20 mg, and 10 mg (0.809 mMol, 0.101 mMol, and 0.05 mMol, respectively). After stirring for 30 minutes, the reaction mixture was concentrated under reduced pressure and chromatographed on 40 g of Silica gel, first using CH$_2$Cl$_2$ as eluent and then using ethyl acetate to provide 383 mg of benzhydryl 7β-trifluoromethanesulfonylamino-3-ethoxycarbonyl-1-carba-3-cephm-4-carboxylate.

90 MHz NMR (CDCl$_3$, δ): 1.0 (t, J=7, 3H, —OCH$_2$CH$_3$), 2.8 (m, 1H), 3.9 (m, 3H), —OCH$_2$CH$_3$ and C$_{6d}$H), 5.15 (d, J=5, 1H, C$_7$H), 6.0 (s, 1H, —CO$_2$CHφ$_2$), 7.3 (m, 10H, C$_6$H$_5$).

(D) To 63 mg of the diester provided in part C, above, was added 1 ml of CH$_2$Cl$_2$ and 15 ml (0.137 mMol) of alyloxycarbonylchloride, 13.5 μl of pyridine, and 2 mg of dimethylamino pyridine. The same portion of allyloxycarbonyl chloride, pyridine, and dimethylamino pyridine were added twice more, after stirring for intervals of 10 minutes. After 5 more minutes, the reaction mixture was poured into a mixture consisting of 50 ml ethyl acetate and 20 ml of saturated NaHCO$_3$ solution. The organic phase was separated and extracted with 20 ml of 1N HCl and dried over anhydrous MgSO$_4$. The organic phase was then filtered and concentrated to provide benzhydryl 7β-[N-(trifluoromethanesulfonyl)allyloxycarbonylamino]-3-ethoxycarbonyl-1-carba-3-cephem-4-carboxylate as a yellow oil, which was used, as is, in part E below.

(E) To 70 mg (0.11 mMol) of the compound provided in part D, above, was added 0.9 ml of CH$_2$Cl$_2$. The resulting solution was cooled to −5° C. and treated with 3 drops of methanol, followed by addition of 17 μl of triethylamine. The resulting reaction mixture was refrigerated for two days and then chromatographed as is on 3 g of silica gel, first eluting with CH$_2$Cl$_2$ and then with a solution consisting of 5% ethyl acetate/95% CH$_2$Cl$_2$. Concentration of the desired fractions yielded 35 mg of crude product, which was in turn chromatographed on a 2 mm silica gel thin layer plate (20 cm × 20 cm) using 5% ethyl acetate/95% CH$_2$Cl$_2$ as eluent to provide 20.7 mg of the title compound as a yellow oil.

90 MHz NMR (CDCl$_3$, δ): 1.3 (t, J=7, 3H, —CH$_2$CH$_3$), 2.8 (m, 1H), 3.5 (s, 3H), —OCH$_3$), 3.8 (m, 1H, C$_6$H), 4.15 (q, J=7, 2H, —CH$_2$CH$_3$), 4.6 (bd, J=4, 2H, —OCH$_2$CH), 5.8 (bs, 1H), 7.0 (s, 1H), 7.3 (bs, 10H).

EXAMPLE 87

7β-Thienylacetylamino-7α-Methoxy-3-ethoxycarbonyl-1-carba-3-cephem-4-carboxylic acid (A) To 20.5 mg (0.0384 mMol) of the compound provided in Example 86, was added 1 ml of CH$_2$Cl$_2$, 2.5 mg (0.0096 mMol) of triphenylphosphine, and 0.5 mg (0.002 mMol) of

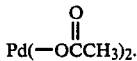

The resulting solution was then treated with 5.4 mg (0.038 mMol) of p-nitrophenol and 13 μl (0.046 mMol) of (CH$_3$CH$_2$CH$_2$CH$_2$)$_3$SnH. After stirring for 7 mintues, an additional 6 μl of (CH$_3$CH$_2$CH$_2$CH$_2$)$_3$SnH was added. The resulting mixture was then cooled to 0° C. and treated with 9 μl (0.0691) of thienylacetyl chloride, 11 μl (0.124 mMol) of pyridine, and 0.5 mg of dimethylamino pyridine. After stirring for 10 minutes, an additional 9 μl of thienylacetyl chloride and 11 μl of pyridine were added. The resulting mixture was diluted with ethyl acetate and poured into a saturated $NaHCO_3$ solution. The organic phase was separated and extracted once with 20 ml of saturated $NaHCO_3$ and twice with 20 ml of 1N HCl. The organic phase was then dried over anhydrous $MgSO_4$, filtered, and concentrated to provide 60 mg of a brown oil. The crude product was chromatographed on 5 g of Silica gel using a (40/60) ethyl acetate/hexane solution as eluent to provide 6 mg of the benzhydryl ester of the title compound.

90 MHz NMR ($CDCl_3$, δ): 0.95 (t, J=7, 3H, —$CH_2CH_3$), 2.7 (m, 1H), 3.35 (s, 3H, $OCH_3$), 3.6-4.0 (m, 5H, —$\underline{CH_2}CH_3$, $CH_2CON$, and $C_6H$), 6.4 (bs, 1H), 6.9 (s, 1H, $CO_2CH\phi_2$).

Mass Spec: 576 (m+ +1).

(B) To 7 mg of the compound produced in part A, above, was added 0.5 ml of dry $CH_2Cl_2$ under a dry nitrogen atmosphere. The resulting solution was treated with 2.6 μl of trimethylsilyl iodide. After 7 minutes, the reaction mixture was diluted with 20 ml of $CH_2Cl_2$ and extracted with 5 ml of saturated $NaHCO_3$ solution. The aqueous phase was then placed in a flask containing a 10% isopropanol/90% $CHCl_3$ mixture. The resulting mixture was then acidified with 12N HCl to PH=2. The two phases were separated and the aqueous phase was extracted with 25 ml of 10% isopropanol/90% $CHCl_3$. The $CHCl_3$ portions were dried over anhydrous $MgSO_4$, filtered, and concentrated under reduced pressure to yield 3.8 g of crude product. The crude product was chromatographed on 1.5 g of Silica gel using 1% acetic acid/99% ethyl acetate solution as eluent to provide 2.5 mg of the title compound.

90 MHz NMR ($CDCl_3$, δ): 1.3 (t, J=7, 3H, $CH_2CH_3$), 1.5 (m, 1H), 2.3 (m, 2H), 2.8 (m, 1H), 3.4 (s, 3H, —$OCH_3$), 3.9 (s, 2H, $CH_2CON$), 3.95 (m, 1H, $C_6H$), 4.2 (q, J=7, 2H, $\underline{OCH_2}CH_3$), 6.9-7.3 (m, 3H, thienyl H), 8.3 (bs, 1H).

Mass Spec: 408 (m+), 409 (m+ +1).
IR (KBr): 1776 cm$^{-1}$ β-lactam.

EXAMPLE 88

7β-(2-Thienylacetylamino)-7α-methoxy-3-ethoxycarbonyl-1-carba-3-cephem-4-carboxylic acid To a flame-dried nitrogen-flushed flask were added 4.7 ml of methyl alcohol and the flask cooled to 0° C. A solution of 2.28 ml of 3.417 mmole of methyllithium in 15 ml of THF was added to the cold methyl alcohol by syringe and the mixture was stirred for 5 minutes. The mixture was then cooled to −78° C. and a solution of 620 mg (1.139 mmole) of diphenylmethyl 7β-(2-thienylacetylamino)-3-ethoxycarbonyl-1-carba-3-cephem-4-carboxylate in 10 ml of THF was added. The cold mixture was stirred for 5 minutes and 0.161 ml (1.424 mmole) of t-butyl hypochlorite was added via syringe with stirring. The reaction mixture was stirred for about 45 minutes, and the reaction quenched by the addition of 0.651 ml of glacial acetic acid and 0.034 ml of trimethyl phosphite. The cooling bath was removed and the reaction mixture allowed to warm to room temperature. The mixture was evaporated in vacuo and the residue of crude product dissolved in methylene chloride. The solution was washed with water and with aqueous sodium bicarbonate solution and dried over sodium sulfate. The dried solution was evaporated in vacuo and the product chromatographed at 0° C. over 60 g of silica using 25%:75% ethyl acetate:hexane, v:v. There were obtained 106 mg of the 7α-methoxy diphenylmethyl ester (16.2% yield).

300 MHz NMR ($CHCl_3$, δ): 1.0 (t, J=7, 3H, —O—$CH_2CH_3$), 1.45, 2.3, 2.4 and 2.8 (m, 4H, $C_1H$ and $C_2H$), 3.45 (s, 3H, —$OCH_3$), 3.8 and 3.95 (m, 2H, —O—$\underline{CH_2}CH_3$), 3.85 (s, 2H, —$CH_2CO$), 4.05 (dd, J=3 and 12, 1H, $C_6H$), 6.4 (s, 1H).

IR (KBr): 1777 cm$^{-1}$, β-lactam.
Mass Spec: 575 (M+).

The 7α-methoxy diphenylmethyl ester, 21 mg (0.0365 mmole), was dissolved in methylene chloride containing 0.023 ml (0.1461 mmole) of triethylsilane and the solution cooled to 0° C. Trifluoroacetic acid (excess) was added to the cold solution which was then allowed to warm to room temperature for 30 minutes. The solution was diluted with acetonitrile:toluene, 1:1, and concentrated to dryness by evaporation. The residue was chromatographed over 5 g of silica gel eluting the product with 0.5% acetic acid in ethyl acetate. The fractions containing the product (tlc) were combined and evaporated to dryness. The solid product was washed with diethyl ether and dried. There were obtained 8.2 mg (52.6% yield) of the title compound.

300 MHz NMR ($CDCl_3$, δ): 1.3 (t, J=7, 3H, —O—$CH_2CH_3$), 1.99, 2.4, and 2.8 (m, 4H, $C_1H$ and $C_2H$), 3.9 (s, 3H, —$OCH_3$), 3.9 (s, 2H, —$CH_2CO$), 4.1 (dd, J=3 and 12, 1H, $C_6H$), 4.29 (q, J=7, 2H, —$CH_2CH_3$), 6.8 (bs, 1H), 7.0 and 7.3 (m, 3H, thienyl H).
IR (KBr): 1775 cm$^{-1}$ (β-lactam).
Mass Spec: 408 (M+).

EXAMPLE 89

7β-Phenoxyacetylamino-7α-methoxy-3-ethoxycarbonyl-1-carba-3-cephem-4-carboxylic acid By using the procedures, conditions and reagents employed in Example 88, 428 mg (0.77 mmole) of diphenylmethyl 7β-phenoxyacetylamino-3-ethoxycarbonyl-1-carba-3-cephem-4-carboxylate was converted to 90 mg of the 7α-methoxy derivative. The diphenylmethyl ester group was removed from the methoxy derivative with trifluoroacetic acid under the conditions described in Example 88 providing 4 mg of the title compound.

300 MHz NMR ($CHCl_3$, δ): 1.3 (t, J=7, 3H, —$OCH_{2H3}$), 1.55, 2.35 and 2.85 (m, 4H, $C_1H$ and $C_2H$), 3.55 (s, 3H, —$OCH_3$), 4.1 (dd, J=3 and 12, 1H, $C_6H$), 4.25 (q, J=7, 2H, —$OCH_2CH_3$), 4.6 (s, 2H, φ—O—$CH_2$—), 7.0, 7.1 and 7.35 (m, 5H, phenoxy H), 7.6 (s, 1H).
IR: 1778 cm$^{-1}$ (β-lactam).
Mass Spec: 419 (M+).

EXAMPLE 90

1-(3-Morpholinopropoxycarbonyloxy)ethyl 7β-[2-(2-aminothiazol-4-yl)-2-(syn)-methoxyiminoacetamido]-3-ethoxycarbonyl-3-cephem-4-carboxylate A. Preparation of 1-chloroethyl 3-morpholinopropylcarbonate To a solution of 31.4 ml (360 mmol) of morpholine in 500 ml of diethyl ether were added slowly 10 g (71.94 mmole) of 3-bromopropanol and the mixture was stirred for one hour at room temperature. The reaction mixture was evaporated under vacuum and 300 ml of methylene chloride and 400 ml of a saturated aqueous solution of sodium bicarbonate were added. The mixture was shaken and the organic layer was separated and washed twice with 300-ml portions of saturated aqueous sodium bicarbonate. The organic layer was separated, dried over sodium sulfate and evaporated to yield 10.3 g of 3-morpholinopropanol.

The 3-morpholinopropanol (2.5 g, 17.22 mmole) was dissolved in 20 ml of THF, lithium hydride (0.144 g, 18.08 mmole) was added and the mixture was heated at the reflux temperature for 10 minutes. The mixture was allowed to cool and was stirred at room temperature for one hour. The mixture was cooled to 0° C. and 2.46 g (17.2 mmole) of 1-chloroethyl chloroformate were added. The mixture was stirred overnight at room temperature concentrated under vacuum and the concentrate dissolved in methylene chloride. The solution was washed with cold aqueous saturated sodium bicarbonate, dried over sodium sulfate and evaporated under vacuum to 2.45 g of A, 1-chloroethyl 3-morpholinopropylcarbonate.

B. Esterification of 7β-[2-(2-t-butyloxycarbonylaminothiazol-4-yl)-2-(syn)-methoxyiminoacetamido]-3-ethoxycarbonyl-3-cephem-4-carboxylic acid with A To a solution of 200 mg (0.37 mmole) of 7β-[2-(2-t-butyloxycarbonylaminothiazol-4-yl)-2-(syn)-methoxyiminoacetamido]-3-ethoxycarbonyl-3-cephem-4-carboxylic acid in 3 ml of DMF was added 0.086 ml (0.78 mmole) of N-methylmorpholine followed by 188 mg (0.744 mmole) of A and 670 mg (4.465 mmole) of sodium iodide. The mixture was stirred at room temperature for two days and was poured into a mixture of 30 ml of a saturated solution of sodium bicarbonate and 60 ml of ethyl acetate. The organic layer was separated and washed with 30 ml of saturated sodium bicarbonate solution, dried over sodium sulfate and evaporated under vacuum to 66 mg of the crude ester. The ester was chromatographed over 10 g of silica gel eluting with ethyl acetate. The fractions containing the product (TLC) were combined and evaporated under vacuum to 32 mg of the desired ester.

300 MHz NMR (CDCl$_3$, δ): 1.3 (m, 3H, —OCH$_2$CH$_3$), 1.55 (s, 9H, t-C$_4$H$_9$), 1.65 (d, J=6, 3H, —CHCH$_3$), 1.6, 2.2, 2.4 and 2.9 (C$_1$H and C$_2$H), 1.9 (m, 2H, NCCH$_2$C—O), 2.5 (m, 6H, (CH$_2$)$_2$N—CH$_2$), 3.7 (m, 4H, —O(CH$_2$)$_2$), 4.0 (s, 3H, OCH$_3$), 4.0–4.2 (m, 5H, C$_6$H, OCH$_2$CH$_3$ and —OCH$_2$CCN), 5.6 (m, 1H, C$_7$H), 7.0 (m, 1H, CHCH$_3$), 7.2 and 7.3 (s, 1H), 9.3 and 9.6 (bs, 1H).

C. Deblocking of B to title compound

A solution of 109 mg (0.148 mmole) of B in 1 ml of methylene chloride was cooled to about 0° C. and 1 ml of trifluoroacetic acid was added. The cooling bath was removed and the mixture was allowed to warm to room temperature. After about 40 minutes the mixture was diluted with 20 ml of methylene chloride and the solution poured into a mixture of 30 ml of saturated aqueous sodium bicarbonate and 50 ml of methylene chloride. The mixture was shaken and the layers separated. The aqueous layer was extracted with 50 ml of methylene chloride and the extract combined with the organic layer. The organic layer was dried over sodium sulfate and evaporated under vacuum to a tan solid. The solid was chromatographed over 20 g of silica gel eluting with 15% isopropanol in ethyl acetate. The fractions containing the product (TLC) were combined and evaporated under vacuum to 59 mg of the title compound. The product was further purified to a white solid by addition of hexane to a solution of the product in 50-50 methylene chloride-diethyl ether, v:v.

300 MHz NMR (CDCl$_3$, δ): 1.3 (m, 3H, —OCH$_2$CH$_3$), 1.6 (m, 3H, —CH$_2$CH$_3$), 1.8, 2.2, 2.4 and 2.9 (m, 4H, C$_1$H and C$_2$H), 1.9 (m, 2H, NCCH$_2$C—O), 2.5 (bs, 6H, (CH$_2$)$_2$NCH$_2$), 3.75 (bs, 4H, O(CH$_2$)$_2$), 4.0 (bs, 4H, —OCH$_3$ and C$_6$H), 4.3 (m, 4H, —OCH$_2$CH$_3$ and O(CO)OCH$_2$CCN), 5.7 (m, 3H, NH$_2$ and C$_7$H), 6.75 (s, s, 1H), 7.0 (m, 1H), 8.3 and 8.4 (bd, J=8, 1H).

IR (CHCl$_3$): 1772 cm$^{-1}$, β-lactam carbonyl.
Mass Spectrum (FD) 653 (M$^+$).

I claim:
1. A compound of the formula

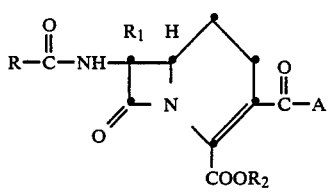

wherein R is hydrogen, C$_1$-C$_6$ alkyl, C$_1$-C$_6$ cyano, carboxy, halogen, amino, C$_1$-C$_4$ alkoxy, C$_1$-C$_4$ alkylthio, or trifluoromethylthio; a phenyl or substituted phenyl group of the formula

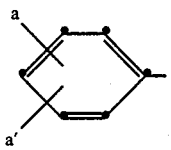

wherein a and a' independently are hydrogen, halogen, hydroxy, C$_1$-C$_4$ alkoxy, C$_1$-C$_4$ alkanyloxy, C$_1$-C$_4$ alkyl, C$_1$-C$_4$ alkylthio, amino, C$_1$-C$_4$ alkanoylamino, C$_1$-C$_4$ alkylsulfonylamino, carboxy, carbamoyl, hydroxymethyl, aminomethyl, or carboxymethyl; or a group of the formula

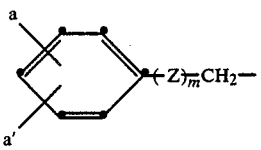

wherein a and a' have the same meanings as defined above, Z is O or S, and m is 0 or 1; or a heteroarylmethyl group of the formula R$^1$—CH$_2$— wherein R$^1$ is thienyl, furyl, benzothienyl, benzofuryl, pyridyl, 4-pyridylthio, pyrimidyl, pyridazinyl, indolyl, pyrazolyl, imidazolyl, triazolyl, tetrazolyl, oxazolyl, thiazolyl, oxadiazolyl, thiadiazolyl, and said heteroaryl groups mono-substituted by amino, hydroxy, halogen, C$_1$-C$_4$ alkyl, C$_1$-C$_4$ alkoxy, or C$_1$-C$_4$ alkylsulfonylamino; or a substituted methyl group of the formula

wherein R² is cyclohex-1,4-dienyl, or a phenyl group of the formula

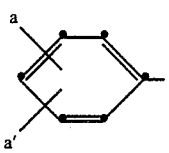

as defined above, or R² is R¹ as defined above, and Q is hydroxy, $C_1$-$C_4$ alkanoyloxy, carboxy, sulfo, amino, sulfoamino, or a substituted amino group of the formula

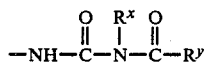

wherein $R^x$ is hydrogen or $C_1$-$C_3$ alkyl, $R^y$ is $C_1$-$C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1$-$C_3$ alkylsulfonyl, $C_1$-$C_3$ alkyl, or $C_1$-$C_4$ alkanoyl; or Q is a substituted amino group of the formula

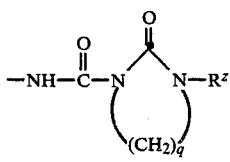

wherein $R^z$ has the same meanings as defined above, and q is 2 or 3; or Q is a substituted amino group of the formula

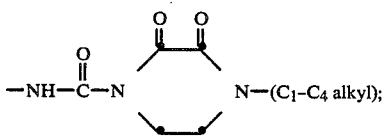

a benzamido group

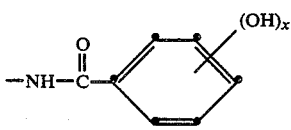

wherein t is 1 to 3;
a pyridone group

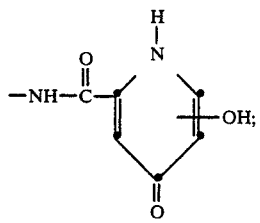

a pyridyl group

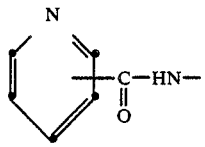

and said pyridyl group mono-substituted by $C_1$-$C_4$ alkyl, amino, carboxy, hydroxy or halogen; an imidazolyl or pyrazolyl group

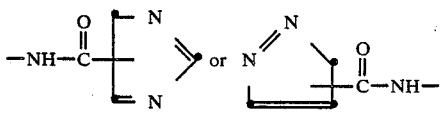

and said imidazolyl or pyrazolyl mono-substituted by $C_1$-$C_4$ alkyl, carboxy, amino, or halogen; a benzpyridazin-4-one group or tautomer thereof

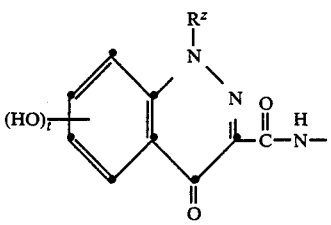

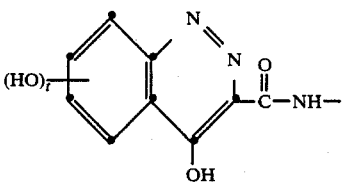

wherein z is hydrogen or $C_1$-$C_3$ alkyl, and t is 1 to 3; or a benzpyranone group

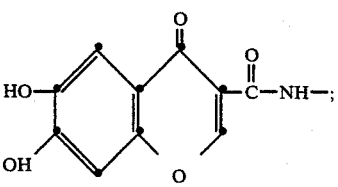

or R is a keto group or an oximino-substituted group of the formulae

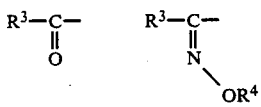

wherein $R^3$ is $R^1$ or $R^2$ as defined above and $R^4$ is hydrogen, $C_1-C_4$ alkyl, $C_1-C_4$ alkyl substituted by halogen, a carboxy-substituted alkyl or cycloalkyl group represented by the formula

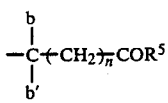

wherein b and b' independently are hydrogen, or $C_1-C_3$ alkyl, n is 0, 1, 2, or 3; and b and b' when taken together with the carbon to which they are bonded form a 3- to 6-membered carbocyclic ring, and $R^5$ is hydroxy, $C_1-C_4$ alkoxy, amino, $C_1-C_4$ alkylamino, or di($C_1-C_4$ alkyl)amino; or $R_4$ is $C_1-C_4$ substituted by phenyl or phenyl substituted by one or two of the same or different groups selected from among $C_1-C_4$ alkyl, hydroxy, halogen, carboxy or protected carboxy; or $R_4$ is $C_1-C_4$ alkyl substituted by amino or protected amino; or $R_4$ is $C_2-C_4$ alkenyl; or $R_4$ is a cyclic lactam group of the formula

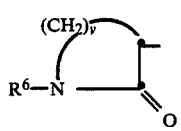

wherein v is 2–4 and $R^6$ is hydrogen or $C_1-C_3$ alkyl; or $R^4$ is a heteroaryl group $$R^1-CH_2-$$

wherein
$R^1$ has the same meanings as defined hereinabove;
$R_1$ is hydrogen, $C_1-C_4$ alkoxy, $C_1-C_4$ alkylthio; or formamido;
$R_2$ is hydrogen, a carboxy-protecting group, or a biologically labile ester;
A is hydroxy, halo, azido, 2-(tri-$C_1-C_4$ alkylsilyl)ethoxy, $C_1-C_6$ alkoxy, $C_2-C_6$ alkenyloxy, $C_2-C_6$ alkinyloxy, $C_1-C_4$ alkoxycarbonyloxy, phenoxy, or phenoxy substituted by one or two of the same or different groups selected from $C_1-C_4$ alkyl, $C_1-C_4$ alkoxy, methylenedioxy, halo, hydroxy, amino, $C_1-C_4$ alkylamino, di-($C_1-C_4$ alkyl)amino, $C_1-C_4$ alkanoylamino, carboxy, carbamoyl, cyano, trifluoromethyl, or $C_1-C_4$ alkanoyl; or $C_1-C_6$ alkoxy substituted by one or two of the same or different groups selected from among hydroxy, amino, $C_1-C_4$ alkylamino, di($C_1-C_4$ alkyl)amino, $C_1-C_4$ alkanoylamino, halo, $C_1-C_4$ alkoxy, $C_1-C_4$ alkylthio, cyano, carboxy, $C_1-C_4$ alkoxycarbonyl, carbamoyl, carbamoyloxy, N-($C_1-C_4$ alkyl)carbamoyloxy, N,N-di-($C_1-C_4$ alkyl)carbamoyloxy, $C_1-C_4$ alkoxycarbonyloxy, phenoxycarbonyloxy, $C_1-C_4$ alkoxycarbonylamino, phenoxycarbonylamino, N-($C_1-C_4$ alkyl)carbamoylamino, N,N-di-($C_1-C_4$ alkyl)carbamoylamino, N-phenylcarbamoylamino, anilino, substituted anilino, phenyl, substituted phenyl, where said substituted anilino and substituted phenyl groups are substituted on the phenyl ring by one or two of the same or different groups selected from among $C_1-C_4$ alkyl, $C_1-C_4$ alkyloxy, methlenedioxy, halo, hydroxy, amino, $C_1-C_4$ alkylamino, di-($C_1-C_4$ alkyl)amino, $C_1-C_4$ alkanoylamino, carboxy, carbamoyl, cyano, trifluoromethyl, or $C_1-C_4$ alkanoyl; or a heterocyclic amino group $R_3NH-$ wherein $R_3$ is thienyl, furyl or a 5-membered nitrogen containing heterocyclic ring represented by the formulae

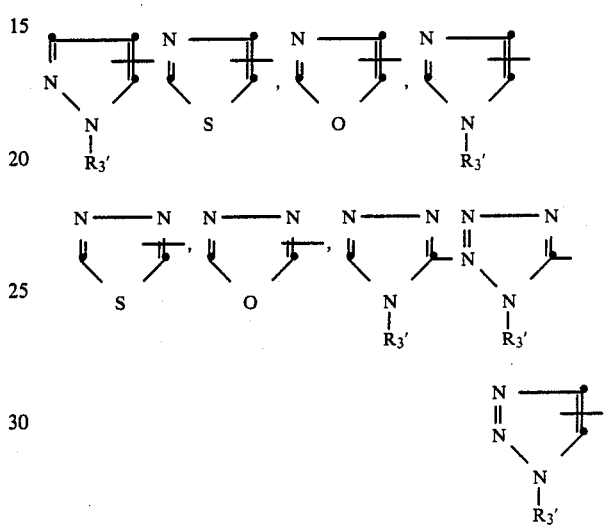

wherein $R_3'$ is hydrogen, $C_1-C_4$ alkyl or $C_1-C_4$ alkyl substituted by carboxy, sulfo, or di($C_1-C_4$ alkyl)amino; or $R_3$ is a 6-membered nitrogen-containing ring represented by the formulae

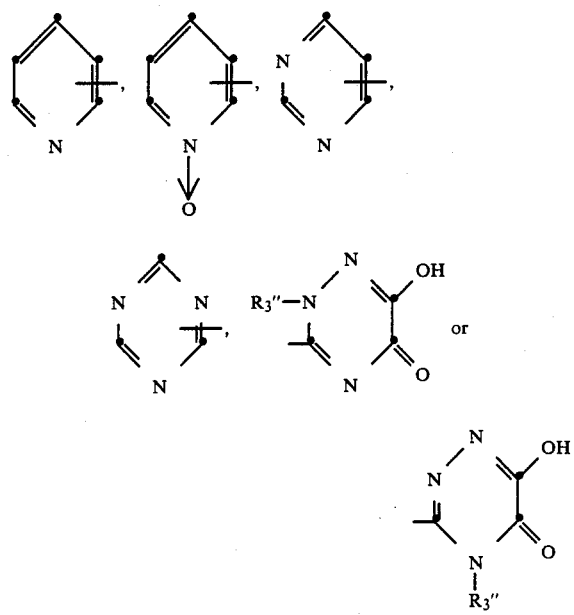

wherein $R_3''$ is hydrogen or $C_1-C_4$ alkyl; or a thio group $R_3^oS-$ wherein $R_3^o$ is phenyl, substituted phenyl as defined above or $R_3$ as defined above; or a quaternary heterocyclic group $R_4{}^o{}^\oplus X^\ominus$ wherein $R_4{}^o{}^\oplus$ is a nitrogen containing heterocyclic represented by the formulae

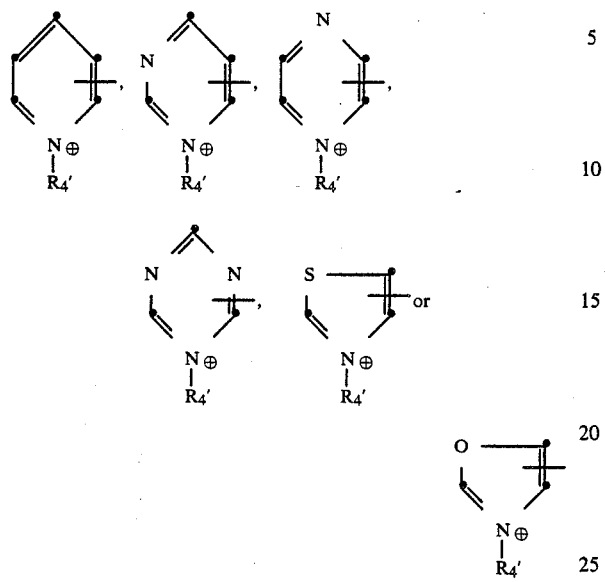

wherein $R_4'$ is $C_1$-$C_4$ alkyl, benzyl, or —CH$_2$COCH$_3$, and $X^\ominus$ is a halide, sulfate, or nitrate anion; or $R_4{}^o{}^\oplus$—S—$X^\ominus$ wherein $R_4{}^o{}^\oplus$ and $X^\ominus$ are as defined above; or $C_1$-$C_6$ alkoxy substituted by a heterocyclic group $R_3$ as defined above;

or A is an amino group represented by the formula

—N(R')(R'')

wherein R' and R'' are independently hydrogen, phenyl, substituted phenyl as defined above, $C_1$-$C_4$ alkyl, $C_1$-$C_4$ alkyl substituted by one or two of the same or different groups selected from among halo, hydroxy, $C_1$-$C_4$ alkanoyloxy, $C_1$-$C_4$ alkylsulfonyloxy, amino, or $C_1$-$C_4$ alkanoylamino; or R' and R'' can be taken together with the nitrogen atom to which they are bonded to form a 5-7 membered ring represented by the formula

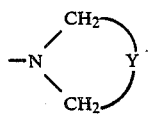

wherein Y is $-(CH_2)_p$ or —CH$_2$—Y'—CH$_2$— wherein p is 2-4 and Y' is O, S, or NR''' wherein R''' is hydrogen or $C_1$-$C_4$ alkyl; or R' is hydrogen and R'' is $C_1$-$C_4$ alkyl substituted by a heterocyclic $R_3$, or a heterocyclic amino group $R_3$NH—, or a thio group $R_3{}^oS$—, or a quaternary heterocyclic group $R_4{}^o{}^\oplus X^\ominus$, wherein $R_3$, $R_3{}^o$, $R_4{}^o{}^\oplus$ and $X^\ominus$ have the same meanings as defined above;

or A is a heterocyclic amino group $R_3$NH— wherein $R_3$ is as defined above, phenyl, or substituted phenyl as defined above;

or A is $C_1$-$C_4$ alkyl, or $C_1$-$C_4$ alkyl monosubstituted by hydroxy, $C_1$-$C_4$ alkanoyloxy, $C_1$-$C_4$ alkoxy, $C_1$-$C_4$ alkylthio, halogen, carboxy, cyano, amino, $C_1$-$C_4$ alkylamino, di-($C_1$-$C_4$ alkyl)amino, $C_1$-$C_4$ alkanoylamino, $C_1$-$C_4$ alkylsulfonylamino, $C_1$-$C_4$ alkylsulfonyloxy, phenyl, substituted phenyl as defined above, phenoxy, substituted phenoxy as defined above, anilino, substituted anilino as defined above, a heterocyclic group $R_3$, a heterocyclic amino group $R_3$NH, a thio group $R_3{}^oS$—, or a quaternary heterocyclic group $R_4{}^o{}^\oplus X^\ominus$ or $R_4{}^o{}^\oplus$—S—$X^\ominus$, wherein $R_3$, $R_3{}^o$, $R_4{}^o{}^\oplus$, and $X^\ominus$ are as defined above;

or A is phenyl, thienyl, furyl, pyridyl, pyrimidyl, imidazolyl, pyrazolyl, tetrazolyl, oxazolyl, thiazolyl, thiadiazolyl or oxadiazolyl, and said phenyl or heterocycle substituted by one or two of the same or different substituents selected from $C_1$-$C_4$ alkyl, $C_1$-$C_4$ alkoxy, halogen, amino, or hydroxy;

or A is a group of the formula —COR$_6$ wherein R$_6$ is hydrogen, hydroxy, $C_1$-$C_4$ alkoxy, phenoxy, substituted phenoxy as defined above, tri-($C_1$-$C_4$ alkyl)silyloxy, amino, $C_1$-$C_4$ alkylamino, di-($C_1$-$C_4$ alkyl)amino, phenyl, substituted phenyl as defined above, or $C_1$-$C_4$ alkyl;

or A is the group —CH$_2$—$^\oplus R_4$ wherein $^\oplus R_4$ is pyridinium, or a substituted pyridinium group substituted by one or two of the same or different groups selected from among $C_1$-$C_4$ alkyl, $C_1$-$C_4$ alkoxy, $C_1$-$C_4$ alkylthio, hydroxy, halogen, trifluoromethyl, cyano, carboxy, carbamoyl, amino, or $C_1$-$C_4$ alkoxycarbonyl; or the pyridinium ring is substituted on adjacent carbon atoms with a divalent alkylene group represented by the formula —CH$_2$—$_{p'}$ wherein p' is 3-5, or the divalent alkylene group is interrupted by an O, S, or one or two N atoms and in addition can contain one or two double bonds and can be substituted in either ring by one or two of the same or different substituents selected from the groups defined above when $^\oplus R_4$ is a substituted pyridine; or $^\oplus R_4$ is a thiazolium ring or a substituted thiazolium ring substituted by one or two of the same or different groups, amino, $C_1$-$C_4$ alkyl, $C_1$-$C_4$ alkylthio, $C_1$-$C_4$ alkoxy, $C_1$-$C_4$ alkyl substituted by hydroxy, $C_1$-$C_4$ alkanoyloxy, $C_1$-$C_4$ alkylsulfonyloxy, halogen, $C_1$-$C_4$ alkoxy, $C_1$-$C_4$ alkylthio, or amino, or the thiazolium ring is substituted on the adjacent carbon atoms with a divalent alkylene group represented by the formula —CH$_2$—$_{p'}$ wherein p' is 3-5; and when R$_2$ is hydrogen, the pharmaceutically acceptable non-toxic salts and biologically labile esters thereof.

2. The compound of claim 1 wherein A is hydroxy, halo, azido, $C_1$-$C_6$ alkoxy, $C_2$-$C_6$ alkenyloxy, $C_2$-$C_6$ alkinyloxy, or substituted $C_1$-$C_6$ alkoxy.

3. The compound of claim 2 wherein A is $C_1$-$C_4$ alkoxy, $C_2$-$C_6$ alkenyloxy, $C_2$-$C_6$ alkinyloxy, or substituted $C_1$-$C_4$ alkoxy.

4. The compound of claim 1 wherein A is an amino group of the formula

—N(R')(R'').

5. The compound of claim 1 wherein A is $C_1$-$C_4$ alkyl or substituted $C_1$-$C_4$ alkyl.

6. The compound of claim 1 wherein A is a group of the formula

7. The compound of claim 1 wherein A is a group of the formula $-CH_2 \oplus R_4$.

8. The compound of claim 1 wherein R is

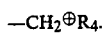

9. The compound of claim 1 wherein R is $R^1-CH_2-$.

10. The compound of claim 9 wherein A is hydroxy, halo, azido, $C_1-C_6$ alkoxy, $C_2-C_6$ alkenyloxy, $C_2-C_6$ alkinyloxy, or substituted $C_1-C_6$ alkoxy.

11. The compound of claim 10 of the formula

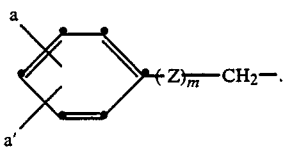

and the pharmaceutically acceptable non-toxic salts thereof.

12. The compound of claim 1 wherein R is a substituted methyl group of the formula

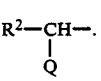

13. The compound of claim 12 wherein Q is amino, sulfamino, or a substituted amino group.

14. The compound of claim 13 wherein Q is a substituted amino group.

15. The compound of claim 14 wherein $R_2$ is phenyl, Q is 4-ethyl-2,3-dioxypiperazin-1-yl carbonylamino, $R_2$ is hydrogen and A is ethoxy.

16. The compound of claim 13 wherein Q is amino.

17. The compound of claim 16 wherein A is hydroxy, halo, azido, $C_1-C_6$ alkoxy, $C_2-C_6$ alkenyloxy, $C_2-C_6$ alkinyloxy, or substituted $C_1-C_6$ alkoxy.

18. The compound of claim 17 wherein R is

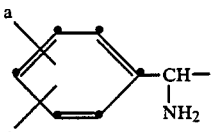

and A is $C_1-C_4$ alkoxy or benzyloxy.

19. The compound of claim 18 of the formula

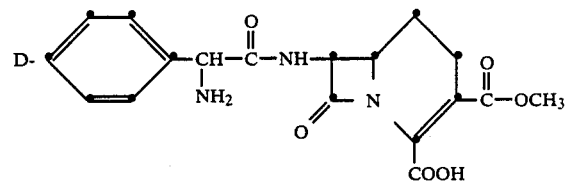

and the pharmaceutically acceptable non-toxic salts thereof.

20. The compound of claim 18 of the formula

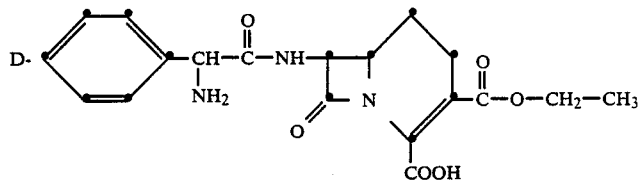

and the pharmaceutically acceptable non-toxic salts thereof.

21. The compound of claim 17 wherein $R^2$ is $R^1$.

22. The compound of claim 21 of the formula

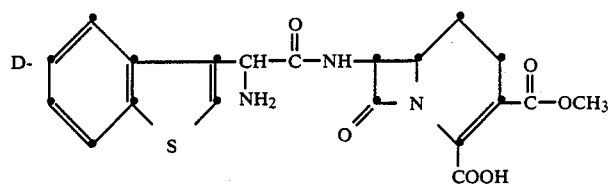

and the pharmaceutically acceptable non-toxic salts thereof.

23. The compound of claim 17 wherein $R_2$ is a biologically labile ester group.

24. The compound of claim 23 wherein $R_2$ is acetoxymethyl, 1-acetoxyethyl, pivaloyloxymethyl, or the 5-methyl-2-oxo-1,3-dioxolen-4-methyl-4-yl group.

25. The compound of claim 24 which is pivaloyloxymethyl 7β-(D-phenylglycylamino)-3-ethoxycarbonyl-1-carba(1-dethia)-3-cephem-4-carboxylate.

26. The compound of claim 12 wherein A is $C_1-C_4$ alkyl or substituted $C_1-C_4$ alkyl.

27. The compound of claim 26 wherein Q is amino, sulfoamino, or a substituted amino group.

28. The compound of claim 25 of the formula

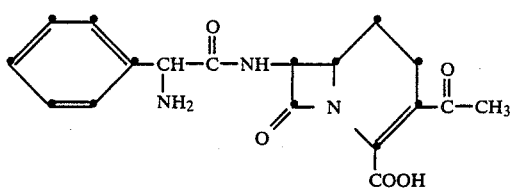

and the pharmaceutically acceptable non-toxic salts thereof.

29. The compound of claim 27 wherein $R_2$ is a biologically labile ester.

30. The compound of claim 27 wherein $R_2$ is acetoxymethyl, 1-acetoxyethyl, pivaloyloxymethyl, or 5-methyl-2-oxo-1,3-dioxolene-4-methyl-4'-yl group.

31. The compound of claim 1 wherein R is a oximino substituted group of the formula

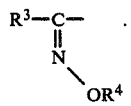

32. The compound of claim 31 wherein $R^3$ is $R^1$ and A is hydroxy, halo, azido, $C_1$–$C_6$ alkoxy, $C_2$–$C_6$ alkenyloxy, $C_2$–$C_6$ alkinyloxy, benzyloxy, substituted benzyloxy, substituted $C_1$–$C_6$ alkoxy, $C_1$–$C_4$ alkyl, or substituted $C_1$–$C_4$ alkyl.

33. The compound of claim 32 wherein $R^3$ is 2-aminothiazol-4-yl, 2-aminooxazol-4-yl, 5-amino-1,2,4-thiadiazol-3-yl, or 5-amino-1,2,4-oxodiazol-3-yl.

34. The compound of claim 33 wherein $R_2$ is a biologically labile ester group of the formula

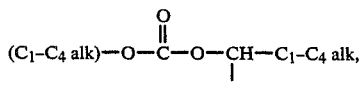

A is ethyl, $R_3$ is 2-aminothiazol-4-yl, and $R_4$ is methyl.

35. The compound of claim 33 of the formula

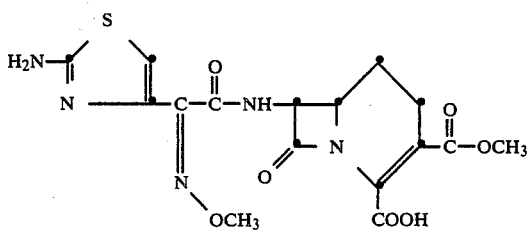

in the syn form and the pharmaceutically acceptable non-toxic salts thereof.

36. The compound of claim 33 of the formula

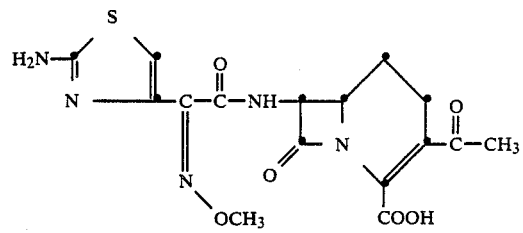

in the syn form and the pharmaceutically acceptable non-toxic salts thereof.

37. The compound of claim 32 wherein $R_2$ is a biologically labile ester selected from among acetoxymethyl, 1-acetoxyethyl, pivaloyloxymethyl, and the 5-methyl-2-oxo-1,5-dioxolen-4-methyl-4'-yl group.

38. The compound of 31 wherein A is a group of the formula —C(O)$R_6$.

39. The compound of claim 38 which is

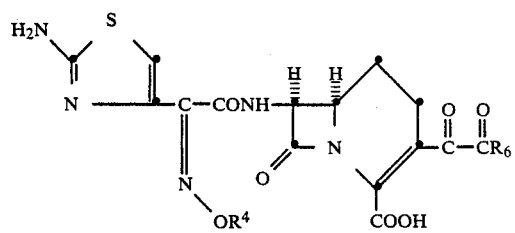

and the pharmaceutically acceptable non-toxic salt thereof.

40. The comppound of claim 39 wherein $R_6$ is $C_1$–$C_4$ alkoxy, amino, or methylamino, and $R^4$ is $C_1$–$C_4$ alkyl or carboxy-substituted alkyl.

41. The compound of claim 38 wherein $R_2$ is a biologically labile ester group selected from among acetoxymethyl, 1-acetoxyethyl, pivaloyloxymethyl, and the 5-methyl-2-oxo-1,3-dioxolen-4-methyl-4'-yl group.

42. The compound of claim 33 of the formula

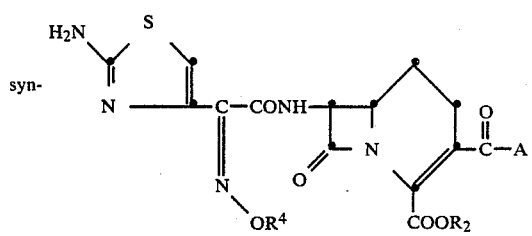

wherein $R_4$ is $C_1$–$C_4$ alkyl, $C_2$–$C_4$ alkenyl, or $C_1$–$C_4$ alkyl substituted by carboxy, amino, halogen, phenyl or substituted phenyl; A is hydroxy, $C_1$–$C_6$ alkoxy, benzyloxy or substituted benzyloxy; and $R_2$ is hydrogen or a biologically labile ester group.

43. The compound of claim 42 wherein $R_4$ is $C_1$–$C_4$ alkyl and A is $C_1$–$C_6$ alkoxy or benzyloxy.

44. The compound of claim 43 wherein $R_4$ is methyl, A is ethoxy and $R_2$ is hydrogen or a biologically labile ester group selected from among 1-acetoxyethyl, 1-pivaloyloxyethyl, 5-methyl-2-oxo-1,3-dioxolene-4-methyl-4'-ylcyclocarbonate, —CH(iC$_3$H$_7$)—OCO—CH$_2$CH(CH$_3$)$_2$, and —CH(CH$_3$)—OCOO—CH(CH$_3$)—CH$_2$—CH$_2$—CH$_3$, —CH(CH$_3$)—OC(O)—O—CH(CH$_3$)$_2$, —CH(CH- $_3$)—OC(O)O—(CH$_2$)$_3$-morpholino and acid addition salts thereof.

45. The compound of claim 42 wherein R$_4$ is C$_1$-C$_4$ alkyl substituted by phenyl, substituted phenyl, amino, carboxy, or halogen and A is benzyloxy or C$_1$-C$_4$ alkoxy.

46. The compound of claim 45 wherein R$_4$ is benzyl or 4-chlorobenzyl and A is benzyloxy.

47. The compound of claim 45 wherein R$_4$ is carboxymethyl and A is C$_1$-C$_4$ alkoxy.

48. The compound of claim 45 wherein R$_4$ is 2-aminoethyl and A is C$_1$-C$_4$ alkoxy.

49. The compound of claim 45 wherein R$_4$ is 2-chloroethyl and A is C$_1$-C$_4$ alkoxy.

50. The compound of claim 42 wherein R$_4$ is C$_2$-C$_4$ alkenyl and A is C$_1$-C$_6$ alkoxy.

51. A pharmaceutical formulation comprising an antibiotically effective amount of a compound of claim 1 wherein R$_2$ is hydrogen, or a pharmaceutically acceptable non-toxic salt or biologically labile ester thereof and a pharmaceutical carrier.

52. The formulation of claim 51 where in the 1-carbacephalosporin R is a substituted methyl group of the formula

and Q is amino, sulfoamino, or substituted amino.

53. The formulation of claim 52 wherein R$^2$ is phenyl, Q is amino, and A is C$_1$-C$_4$ alkoxy, substituted C$_1$-C$_4$ alkoxy, C$_1$-C$_4$ alkyl, substituted C$_1$-C$_4$ alkyl or the group —C(O)R$_6$.

54. The formulation of claim 51 wherein the 1-carbacephalosporin R is an oximino substituted group of the formula

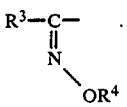

55. The formulation of claim 54 wherein A is C$_1$-C$_4$ alkoxy, substituted C$_1$-C$_4$ alkoxy, C$_1$-C$_4$ alkyl, substituted C$_1$-C$_4$ alkyl, or the group —C(O)R$_6$.

56. A method for treating bacterial infections in man and animals which comprises administering an antibacterially effective amount of an antibiotic compound of claim 1 wherein R$_2$ is hydrogen or a pharmaceutically acceptable non-toxic salt or biologically labile ester thereof.

* * * * *